United States Patent
Caroff et al.

(10) Patent No.: US 10,259,807 B2
(45) Date of Patent: *Apr. 16, 2019

(54) 1-(PIPERAZIN-1-YL)-2-([1,2,4]TRIAZOL-1-YL)-ETHANONE DERIVATIVES

(71) Applicant: Idorsia Pharmaceuticals Ltd., Allschwil (CH)

(72) Inventors: Eva Caroff, Allschwil (CH); Emmanuel Meyer, Allschwil (CH)

(73) Assignee: IDORSIA PHARMACEUTICALS LTD., Allschwil (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/906,882

(22) PCT Filed: Jul. 21, 2014

(86) PCT No.: PCT/EP2014/065639
§ 371 (c)(1),
(2) Date: Jan. 21, 2016

(87) PCT Pub. No.: WO2015/011099
PCT Pub. Date: Jan. 29, 2015

(65) Prior Publication Data
US 2016/0176862 A1    Jun. 23, 2016

(30) Foreign Application Priority Data

Jul. 22, 2013  (WO) .................. PCT/IB2013/056001

(51) Int. Cl.
*C07D 417/14*    (2006.01)

(52) U.S. Cl.
CPC .................. *C07D 417/14* (2013.01)

(58) Field of Classification Search
CPC ................................................... C07D 417/14
See application file for complete search history.

(56) References Cited

U.S. PATENT DOCUMENTS

| | | |
|---|---|---|
| 7,589,199 B2 | 9/2009 | Pennell et al. |
| 7,645,755 B2 | 1/2010 | Illig et al. |
| 7,842,693 B2 | 11/2010 | Pennell et al. |
| 8,324,216 B2 | 12/2012 | Pennell et al. |
| 8,450,317 B2 | 5/2013 | Kowalski et al. |
| 8,889,677 B2 | 11/2014 | Grauert |
| 9,266,876 B2 | 2/2016 | Caroff et al. |
| 9,732,075 B2 | 8/2017 | Boss et al. |
| 9,850,256 B2 | 12/2017 | Cren et al. |
| 10,047,080 B2 * | 8/2018 | Caroff .................. C07D 417/14 |
| 2004/0082571 A1 | 4/2004 | Pennell et al. |
| 2004/0162282 A1 | 8/2004 | Pennell et al. |
| 2005/0256130 A1 | 11/2005 | Pennell |
| 2006/0106218 A1 | 5/2006 | Pennell et al. |
| 2006/0276465 A1 | 12/2006 | Kawahara et al. |
| 2008/0139572 A1 | 6/2008 | Wang et al. |
| 2010/0094006 A1 | 4/2010 | Nam et al. |
| 2010/0240618 A1 | 9/2010 | Pennell et al. |
| 2011/0136823 A1 | 6/2011 | Deprez et al. |
| 2013/0072497 A1 | 3/2013 | Lorsbach et al. |
| 2014/0371204 A1 | 12/2014 | Caroff et al. |
| 2016/0176862 A1 | 6/2016 | Caroff et al. |
| 2017/0107214 A1 | 4/2017 | Caroff et al. |

(Continued)

FOREIGN PATENT DOCUMENTS

| | | |
|---|---|---|
| EP | 1 698 620 A1 | 9/2006 |
| WO | WO 02/059108 A1 | 8/2002 |

(Continued)

OTHER PUBLICATIONS

International Search Report of PCT/EP2014/065639 dated Sep. 3, 2014.
Groom et al., "CXCR3 in T cell function," Exp Cell Res 317, 2011, pp. 620-631.
Groom et al., "CXCR3 ligands: redundant, collaborative and antagonistic functions," Immunol Cell Biol 2011, pp. 1-9.
Handbook of Pharmaceutical Salts. Properties, Selection and Use., P. Heinrich Stahl, Camille G. Wermuth (Eds.), Wiley-VCH, 2008, 24 pages.
Hancock et al., "Requirement of the Chemokine Receptor CXCR3 for Acute Allograft Rejection," J Exp Med 2000, I92, pp. 1515-1519.
Jenh et al., "A selective and potent CXCR3 antagonist SCH 546738 attenuates the development of autoimmune diseases and delays gratt rejection," BMC Immunology 2012, 13:2, pp. 1-14.
Lacotte et al., "CXCR3, Inflammation, and Autoimmune Diseases," Ann N Y Aced Sci 1173: 2009, pp. 310-317.

(Continued)

*Primary Examiner* — Sreenivasan Padmanabhan
*Assistant Examiner* — Jody L Karol
(74) *Attorney, Agent, or Firm* — Arent Fox LLP

(57) ABSTRACT

The invention relates to compounds of Formula (I)

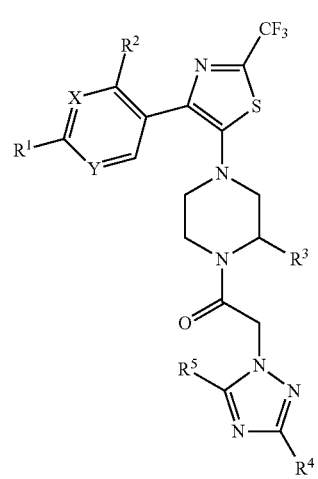

Formula (I)

wherein X, Y, $R^1$, $R^2$, $R^3$, $R^4$ and $R^5$ are as described in the description; to pharmaceutically acceptable salts thereof, and to the use of such compounds as medicaments, especially as modulators of the CXCR3 receptor.

16 Claims, No Drawings

(56) References Cited

U.S. PATENT DOCUMENTS

| | | |
|---|---|---|
| 2017/0305897 A1 | 10/2017 | Boss et al. |
| 2018/0009799 A1 | 1/2018 | Caroff et al. |
| 2018/0009800 A1 | 1/2018 | Caroff et al. |

FOREIGN PATENT DOCUMENTS

| | | |
|---|---|---|
| WO | WO 2002/059107 A1 | 8/2002 |
| WO | WO 02/070511 A1 | 9/2002 |
| WO | WO 2005/003127 A1 | 1/2005 |
| WO | WO 2005/035534 A1 | 4/2005 |
| WO | WO 2005/040136 A1 | 5/2005 |
| WO | WO 2005/042516 A2 | 5/2005 |
| WO | WO 2005/044797 A1 | 5/2005 |
| WO | WO 2005/051304 A2 | 6/2005 |
| WO | WO 2006/047277 A2 | 5/2006 |
| WO | WO 2006/088836 A2 | 8/2006 |
| WO | WO 2006/088837 A2 | 8/2006 |
| WO | WO 2006/088840 A1 | 8/2006 |
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2007/002293 A2 | 1/2007 |
| WO | WO 2007/002742 A1 | 1/2007 |
| WO | WO 2007/014290 A2 | 2/2007 |
| WO | WO 2007/047202 A1 | 4/2007 |
| WO | WO 2007/048088 A2 | 4/2007 |
| WO | WO 2007/070433 A2 | 6/2007 |
| WO | WO 2013/114332 A1 | 6/2007 |
| WO | WO 2007/076318 A2 | 7/2007 |
| WO | WO 2007/100610 A2 | 9/2007 |
| WO | WO 2007/109238 A1 | 9/2007 |
| WO | WO 2007/124369 A2 | 11/2007 |
| WO | WO 2007/127635 A2 | 11/2007 |
| WO | WO 2008/003861 A1 | 1/2008 |
| WO | WO 2008/008453 A1 | 1/2008 |
| WO | WO 2008/013622 A2 | 1/2008 |
| WO | WO 2008/013925 A2 | 1/2008 |
| WO | WO 2008/079279 A1 | 7/2008 |
| WO | WO 2008/091580 A2 | 7/2008 |
| WO | WO 2008/091594 A2 | 7/2008 |
| WO | WO 2008/147822 A1 | 12/2008 |
| WO | WO 2009/020534 A2 | 2/2009 |
| WO | WO 2009/055514 A2 | 4/2009 |
| WO | WO 2009/079490 A1 | 6/2009 |
| WO | WO 2009/094407 A2 | 7/2009 |
| WO | WO 2009/094445 A2 | 7/2009 |
| WO | WO 2009/105435 A1 | 8/2009 |
| WO | WO 2009/132785 A1 | 11/2009 |
| WO | WO 2010/037479 A1 | 4/2010 |
| WO | WO 2010/065579 A2 | 6/2010 |
| WO | WO 2010/066353 A1 | 6/2010 |
| WO | WO 2010/126811 A1 | 11/2010 |
| WO | WO 2010/126851 A1 | 11/2010 |
| WO | WO 2010/149275 A1 | 12/2010 |
| WO | WO 2011/018401 A1 | 2/2011 |
| WO | WO 2011/018415 A2 | 2/2011 |
| WO | WO 2011/051243 A1 | 5/2011 |
| WO | WO 2011/051244 A1 | 5/2011 |
| WO | WO 2011/076699 A1 | 6/2011 |
| WO | WO 2011/084985 A1 | 7/2011 |
| WO | WO 2011/134969 A1 | 11/2011 |
| WO | WO 2011/144586 A1 | 11/2011 |
| WO | WO 2011/146182 A1 | 11/2011 |
| WO | WO 2011/147765 A1 | 12/2011 |
| WO | WO 2012/020060 A1 | 2/2012 |
| WO | WO 2012/025557 A1 | 3/2012 |
| WO | WO 2012/055837 A1 | 5/2012 |
| WO | WO 2012/069633 A1 | 5/2012 |
| WO | WO 2012/082580 A1 | 6/2012 |
| WO | WO 2012/104273 A1 | 8/2012 |
| WO | WO 2012/107475 A1 | 8/2012 |
| WO | WO 2012/107477 A1 | 8/2012 |
| WO | WO 2012/171337 A1 | 12/2012 |
| WO | WO 2013/037768 A1 | 3/2013 |
| WO | WO 2013/056911 A1 | 4/2013 |
| WO | WO 2013/056915 A1 | 4/2013 |
| WO | WO 2013/083741 A1 | 6/2013 |
| WO | WO 2013/107761 A1 | 7/2013 |
| WO | WO 2013/110134 A1 | 8/2013 |
| WO | WO 2013/114332 A2 | 8/2013 |
| WO | WO 2013/127784 A1 | 9/2013 |
| WO | WO 2013/127808 A1 | 9/2013 |
| WO | WO 2014/062938 A1 | 4/2014 |
| WO | WO 2014/075873 A1 | 5/2014 |
| WO | WO 2014/075874 A1 | 5/2014 |
| WO | WO 2014/092100 A1 | 6/2014 |
| WO | WO 2014/206896 A1 | 12/2014 |
| WO | WO 2015/011099 A1 | 1/2015 |
| WO | WO 2013/026683 A1 | 2/2015 |
| WO | WO 2015/145322 A1 | 10/2015 |
| WO | WO 2016/113344 A1 | 7/2016 |
| WO | WO 2016/113346 A1 | 7/2016 |

OTHER PUBLICATIONS

Lammers et al., "Gliadin induces an Increase in Intestinal Permeability and Zonulin Release by Binding to the Chemokine Receptor CXCR3," Gastroenterology 2008, 135, pp. 194 204.

Mach et al., "Differential expression of three T lymphocyte-activating CXC chemokines by human atheroma-associated cells," J Clin Invest 1999, 104, pp. 1041-1050.

Mcguinness et al., "Novel CXCR3 Antagonists with a Piperazinyl-Poperidine Core," Bioorg. Med. Chem. Lett. 2009 (doi: 10.1016/j.bmcl.2009.07.020), 7 pages.

Menke et al., "Distinct Roles of CSF-1 Isoforms in Lupus Nephritis," J Am Soc Nephrol 22: 2011, pp. 1821-1833.

Mohan et al., "Blockade of Chemokine Receptor CXCR3 Inhibits T Cell Recruitment to Inflamed Joints and Decreases the Severity of Adjuvant Arthritis," T. B. J Immunol 2007, 179, pp. 8463-8469.

Nie et al., "Attenuation of acute lung inflammation induced by cigarette smoke in CXCR3 knockout mice," Respir Res 2008, 9, 82, pp. 1-10.

Pharmaceutical Salts and Co crystals, Johan Wouters and Luc Quere (Eds.), RSC Publishing, 2012.

Pradelli et al., "Antagonism of chemokine receptor CXCR3 inhibits osteosarcoma metastasis to lungs," Int J Cancer 2009, 125, pp. 2586-2594.

Prokopowicz et al., Optimization of a biaryl series of CXCR3 antagonists, 244th ACS National Meeting, Philadelphia, US, Aug. 19-23, 2012.

Protective Groups in Organic Synthesis, T.W. Greene, P.G.M. Wuts, Wiley-Interscience, 1999.

Reinhart et al., "Identification of anti-inflammatory targets for Huntington's disease using a brain slice-based screening assay," Neurobiol Dis 2011, 43, pp. 248-256.

Remington, The Science and Practice of Pharmacy, 21st Edition (2005), Part 5, "Pharmaceutical Manufacturing" [published by Lippincott Williams & Wilkins].

Saetta et al., "Increased Expression of the Chemokine Receptor CXCR3 and Its Ligand CXCL10 in Peripheral Airways of Smokers with Chronic Obstructive Pulmonary Disease," Am J Respir Crit Care Med 2002, 165, pp. 1404-1409.

Sakthivel et al., "CXCL10 blockade protects mice from cyclophosphamide-induced cystitis," J Immune Based Ther Vaccines 2008, 6, 6, 38 pages.

Singh et al.,"CXCL10-Producing Mucosal CD4+ T Cells, NK Cells, and NKT Cells Are Associated with Chronic Colitis in IL-10-/- Mice, Which Can Be Abrogated by Anti-CXCL10 Antibody Inhibition," J Interferon Cytokine Res 2008, 28, pp. 31-43.

Tacke et al., "Serum chemokine receptor CXCR3 ligands are associated with progression, organ dysfunction and complications of chronic liver diseases," Liver Int 2011, 31, pp. 840-849.

Trentin et al., "The chemokine receptor CXCR3 is expressed on malignant B cells and mediates chemotaxis," J Clin Invest 1999, 104, pp. 115-121.

Van Weering et al., "CXCL10/CXCR3 Signaling in Glia Cells Differentially Affects NMDA-Induced Cell Death in CA and DG Neurons of the Mouse Hippocampus," Hippocampus 2011, 21, 220, pp. 1-13.

(56) References Cited

OTHER PUBLICATIONS

Veillard et al., "Differential Influence of Chemokine Receptors CCR2 and CXCR3 in Development of Atherosclerosis in Viro," Circulation 2005, 112, pp. 870-879.

Wang et al., "Camphor sulfonamide derivatives as novel, potent and selective CXCR3 antaqonists," Bioorg. Med. Chem. Lett. 2009, pp. 114-118.

Watson et al., "Development of CXCR3 antagonists. Part 2: identification of 2-amino(1piperidinyl)azoles as potent CXCR3 antagonists," Bioorg. Med. Chem. Lett. 2007, pp. 6606-6810.

Wijtmans et al., "Towards Small-Molecule CXCR3 Ligands with Clinical Potential," ChemMedChem 2008, pp. 861-872.

Zhang et al., "Pyridinylquinazolines Selectively Inhibit Human Methionine Aminopeptidase-1 in Cells," J. Med. Chem. 2013, pp. 3996-4016.

Office Action issued in U.S. Appl. No. 15/128,846 dated Sep. 14, 2017 (7 pages).

Office Action issued in U.S. Appl. No. 15/544,223 dated Jan. 4, 2018 (8 pages).

International Search Report issued in International Application No. PCT/EP2016/050645 dated Mar. 15, 2016. (2 pages).

Billottet et al., "CXCR3, a double-edged sword in tumor progression and angiogenesis," Biochimica et Biophysica Acta, 2013, pp. 287-295, vol. 1836.

Campanella et al., "Chemokine receptor CXCR3 and its ligands CXCL9 and CXCL10 are required for the development of murine cerebral malaria," PNAS, Mar. 25, 2008, pp. 4814-4819, vol. 105, No. 12.

Denoyer et al, "CXCR3 Antagonism of SDF-1 (5-67) Restores Trabecular Function and Prevents Retinal Neurodegeneration in a Rat Model of Ocular Hypertension," PLoS One, Jun. 2012, vol. 7, issue 6, doi:10.1371/journal.pone.0037873.

Fulton, "The Chemokine Receptors CXCR4 and CXCR3 in Cancer," Current Oncology Reports, 2009, pp. 125-131, vol. 11.

Ha et al., "Endoplasmic reticulum stress-regulated CXCR3 pathway mediates inflammation and neuronal injury in acute glaucoma," Cell Death and Disease, 2015, vol. 6. doi:10.1038/cddis.2015.281.

Jiang et al., "Regulation of pulmonary fibrosis by chemokine receptor CXCR3," The Journal of Clinical Investigation, Jul. 2004, pp. 291-299, vol. 114, No. 2.

Krauthausen et al., "CXCR3 promotes plaque formation and behavioral deficits in an Alzheimer's disease model," The Journal of Clinical Investigation, Jan. 2015, pp. 365-378, vol. 125, No. 1.

Notice of Allowance issued in U.S. Appl. No. 15/543,457 dated Apr. 3, 2018. (34 pages).

Stroke et al., "Identification of CXCR3 receptor agonists in combinatorial small-molecule libraries," Biochemical and Biophysical Research Communications, 2006, pp. 221-228, vol. 349.

\* cited by examiner

1-(PIPERAZIN-1-YL)-2-([1,2,4]TRIAZOL-1-YL)-ETHANONE DERIVATIVES

CROSS-REFERENCE TO RELATED APPLICATIONS

This application is a National Stage entry of International Application No. PCT/EP2014/065639, filed Jul. 21, 2014, which claims priority to International Application No. PCT/IB2013/056001, filed Jul. 22, 2013. The disclosures of the prior applications are hereby incorporated in their entirety by reference.

The present invention relates to novel 1-(piperazin-1-yl)-2-([1,2,4]triazol-1-yl)-ethanone derivatives of Formula (I), and their use as pharmaceuticals. The invention also concerns related aspects including processes for the preparation of the compounds, pharmaceutical compositions containing one or more compounds of Formula (I), and especially their use as CXCR3 receptor modulators.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

The chemokine receptor CXCR3 is a G-protein coupled receptor binding to the inflammatory chemokines CXCL9 (initially called MIG, monokine induced by interferon-γ [INF-γ]), CXCL10 (IP-10, INF-γ-inducible protein 10), and CXCL11 (I-TAC, INF-γ-inducible T cell α chemo-attractant). CXCR3 is mainly expressed on activated T helper type 1 (Th1) lymphocytes, but is also present on natural killer cells, macrophages, dendritic cells and a subset of B lymphocytes. The three CXCR3 ligands are expressed mainly under inflammatory conditions, expression in healthy tissue is very low. Cells that can express CXCR3 ligands, for instance after exposure to inflammatory cytokines such as interferon-γ or TNF-α, include diverse stromal cells such as endothelial cells, fibroblasts, epithelial cells, keratinocytes but also includes hematopoietic cells such as macrophages and monocytes. The interaction of CXCR3 and its ligands (henceforth referred to as the CXCR3 axis) is involved in guiding receptor bearing cells to specific locations in the body, particularly to sites of inflammation, immune injury and immune dysfunction and is also associated with tissue damage, the induction of apoptosis, cell growth, and angiostasis. CXCR3 and its ligands are upregulated and highly expressed in diverse pathological situations including autoimmune disorders, inflammation, infection, transplant rejection, fibrosis, neurodegeneration and cancer.

A role of the CXCR3 axis in autoimmune disorders is corroborated by several preclinical and clinical observations. Autoimmune disorders in which histological analysis of inflammatory lesions or serum levels of patients revealed elevated levels of CXCR3 ligands or increased numbers of CXCR3 positive cells include rheumatoid arthritis (RA), systemic lupus erythematosus (SLE), lupus nephritis, multiple sclerosis (MS), inflammatory bowel disease (IBD; comprising Crohn's disease and ulcerative colitis), and type I diabetes mellitus (Groom, J. R. & Luster, A. D. Immunol Cell Biol 2011, 89, 207; Groom, J. R. & Luster, A. D. Exp Cell Res 2011, 317, 620; Lacotte, S., Brun, S., Muller, S. & Dumortier, H. Ann N Y Acad Sci 2009, 1173, 310). As expression of CXCR3 ligands is very low in healthy tissue, the above cited correlative evidence strongly suggest a role for CXCR3 in human autoimmune diseases.

Preclinical disease models performed with CXCR3 deficient mice, mice deficient for one of the CXCR3 ligands or the use of antibodies blocking the function of either CXCR3 or one of its ligands further corroborate a role for the CXCR3 axis in immune pathology. For instance, it has been shown that mice deficient for either CXCR3 or the CXCR3 ligand CXCL9 show reduced pathology in a model for lupus nephritis (Menke, J. et al. J Am Soc Nephrol 2008, 19, 1177). In an animal model for another form of kidney inflammation, interstitial cystitis, administration of an antibody blocking CXCL10 function was shown to reduce pathology in cyclophosphamide-induced cystitis (Sakthivel, S. K. et al. J Immune Based Ther Vaccines 2008, 6, 6). Similarly, blocking CXCL10 with an antibody reduced pathology in a rat model of rheumatoid arthritis (Mohan, K. & Issekutz, T. B. J Immunol 2007, 179, 8463). Similarly, in a murine model of inflammatory bowel disease, a blocking antibody against CXCL10 could prevent pathology in a therapeutic setting (Singh, U. P. et al. J Interferon Cytokine Res 2008, 28, 31). Further, experiments performed with tissue from CXCR3 deficient mice suggests a role for CXCR3 in celiac disease, another autoimmune type disorder (Lammers, K. M. et al. Gastroenterology 2008, 135, 194).

Inflammatory diseases that are associated with an elevated expression of the CXCR3 axis include chronic obstructive pulmonary disorder (COPD), asthma, sarcoidosis, atherosclerosis and myocarditis (Groom, J. R. & Luster, A. D. Immunol Cell Biol 2011, 89, 207; Groom, J. R. & Luster, A. D. Exp Cell Res 2011, 317, 620).

One study has shown that CXCR3 positive cells are increased in the lungs of smokers with COPD compared to healthy subjects and immunoreactivity for the CXCR3-ligand CXCL10 was present in the bronchiolar epithelium of smokers with COPD but not in the bronchiolar epithelium of smoking and nonsmoking control subjects (Saetta, M. et al. Am J Respir Crit Care Med 2002, 165, 1404). These findings suggest that the CXCR3 axis may be involved in the immune cell recruitment that occurs in peripheral airways of smokers with COPD. In agreement with these observations, a preclinical study of COPD revealed an attenuation of acute lung inflammation induced by cigarette smoke in CXCR3 deficient mice (Nie, L. et al. Respir Res 2008, 9, 82).

In one investigation of atherosclerosis, CXCR3 expression was found on all T cells within human atherosclerotic lesions. CXCR3 ligands CXCL9, CXCL10 and CXCL11 were all found in endothelial and smooth muscle cells associated with those lesions, suggesting that they are involved in the recruitment and retention of CXCR3 positive cells, particularly activated T lymphocytes, observed within vascular wall lesions during atherogenesis (Mach, F. et al. J Clin Invest 1999, 104, 1041).

Preclinical studies further support a role of CXCR3 in the development of atherosclerosis. CXCR3 genetic deletion in mice lacking ApoE results in a significantly reduced atherosclerotic lesion development within abdominal aortas (Veillard, N. R. et al. Circulation 2005, 112, 870).

A pivotal role for the CXCR3 axis has also been suggested in rejection reactions after organ transplantation and bone marrow transplantation related toxicity (Groom, J. R. & Luster, A. D. Exp Cell Res 2011, 317, 620). Preclinically, CXCR3 deficient mice show a significant resistance to allograft rejection (Hancock, W. W. et al. J Exp Med 2000, 192, 1515).

CXCR3 ligand plasma concentrations also positively correlate with diverse liver pathologies, including liver cirrhosis and fibrosis in humans (Tacke, F., et al. Liver Int 2011, 31, 840).

In the field of oncology, blocking the CXCR3 axis has been proposed to help limit the metastatic spread of cancer cells. For instance, administration of the small molecule CXCR3 receptor antagonist AMG487 could limit the metastasis of tumor cells to the lungs (Pradelli, E. et al. Int J Cancer 2009, 125, 2586). Functional evidence for a role of CXCR3 in regulating B-cell chronic lymphocytic leukemia (CLL) was reported by Trentin and coworkers (Trentin, L. et al. J Clin Invest 1999, 104, 115).

In the central nervous system, blocking the CXCR3 axis may have beneficial effects and prevent neurodegeneration. Increased expression of CXCL10 in the CNS has been demonstrated in ischemia, Alzheimer's disease, multiple sclerosis (MS), and human immunodeficiency virus (HIV)-encephalitis. For example, ex vivo experiments have shown that tissue derived from either CXCR3 or CXCL10 deficient mice, neuronal cell death was diminished after neurotoxic NMDA-treatment when compared to tissue derived from wild type mice (van Weering, H. R. et al. Hippocampus 2011, 21, 220). In a study looking to indentify drug-like molecules that provide neuroprotection against HTT fragment-induced neurodegeneration in a model for Huntington's disease, two CXCR3 receptor antagonists were identified (Reinhart, P. H. et al. Neurobiol Dis 2011, 43, 248.)

Different 1-(piperazin-1-yl)-2-heteroaryl-ethanone derivatives have been disclosed in WO 2010/126811. A more detailed structure-activity-relationship with respect to important drug-related properties of such compounds has been discussed on a poster presentation (A. Prokopowicz et al., *Optimization of a biatyl series of CXCR3 antagonists*, 244th ACS National Meeting, Philadelphia, US, Aug. 19-23, 2012). 4-(Benzoimidazol-2-yl)-thiazole derivatives have been disclosed in WO 2013/114332.

It has now been found that particular 2-([1,2,4]triazol-1-yl)-1-[4-(2-trifluoromethyl-thiazol-5-yl)-piperazin-1-yl]-ethanone derivatives have surprisingly high plasma concentrations after oral administration and are potent CXCR3 modulators which may be useful for the treatment of diseases that are mediated or sustained through the CXCR3 axis, including autoimmune disorders (e.g. rheumatoid arthritis, multiple sclerosis, inflammatory bowel disease, systemic lupus erythematosus, lupus nephritis, interstitial cystitis, celiac disease), inflammatory disorders (e.g. asthma, COPD, atherosclerosis, myocarditis, sarcoidosis), transplantation rejection, fibrosis (e.g. liver cirrhosis), neurodegeneration and conditions involving neuronal death (e.g. Alzheimer's disease, Huntington's disease), and cancer.

1) In a first embodiment, the present invention relates to compounds of Formula (I)

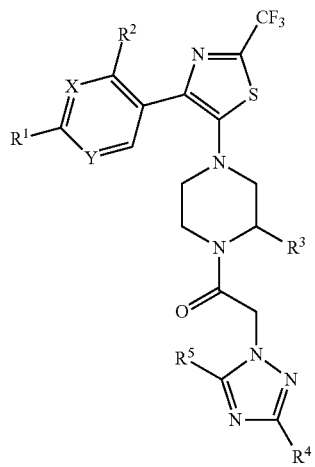

Formula (I)

wherein
X represents N or CH;
Y represents N or $CR^6$;
$R^1$ represents $(C_{1-4})$alkyl; $(C_{3-6})$cycloalkyl; $(C_{1-4})$alkoxy; $(C_{3-6})$cycloalkoxy; $(C_{1-3})$fluoroalkyl; $(C_{1-3})$fluoroalkoxy; halogen; cyano; $(C_{1-2})$alkoxy-$(C_{2-3})$alkoxy; $(C_{1-3})$alkyl which is mono-substituted with $-NR^7R^8$; $(C_{2-3})$alkoxy which is mono-substituted with $-NR^7R^8$; heterocyclyl, wherein the heterocyclyl is a 4- to 6-membered mono-cyclic saturated ring containing one or two heteroatoms independently selected from nitrogen and oxygen and wherein said heterocyclyl is unsubstituted or mono-substituted with $(C_{1-2})$alkyl; or heterocyclyloxy, wherein the heterocyclyl is a 4- to 6-membered mono-cyclic saturated ring containing one oxygen atom;
$R^2$ represents hydrogen, $(C_{1-4})$alkoxy or fluoro;
$R^3$ represents hydrogen or $(C_{1-4})$alkyl;
$R^4$ represents $(C_{1-4})$alkyl, $(C_{1-4})$alkyl which is mono-substituted with hydroxy, or $(C_{1-2})$alkyl which is mono-substituted with $-NR^7R^8$;
$R^5$ represents $(C_{1-4})$alkyl or $(C_{1-4})$alkyl which is mono-substituted with hydroxy;
$R^6$ represents hydrogen, $(C_{1-4})$alkyl or fluoro; or $R^1$ and $R^6$ form, together with the carbon atoms to which they are attached, a 5- or 6-membered heterocyclic ring, wherein the moiety needed to complete said heterocyclic ring is selected from $-OCH_2CH_2-*$, $-OCH_2O-*$, $-OCH_2CH_2CH_2-*$ and $-OCH_2CH_2O-*$, wherein the asterisks indicate the bond which is linked to the $R^6$ bearing carbon atom;
$R^7$ represents $(C_{1-2})$alkyl; and
$R^8$ represents $(C_{1-2})$alkyl;
and to the salts (in particular pharmaceutically acceptable salts) of such compounds.

Definitions provided herein are intended to apply uniformly to the compounds of Formulae (I), ($I_P$), (II), (III), (IV) and (V) as defined in any one of embodiments 1) to 45), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) as defined in any one of embodiments 1) to 45), may contain one or more stereogenic or asymmetric centers, such as one or more asymmetric carbon atoms. The compounds of Formula (I) may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers, is understood in the context of the present invention to mean especially that the respective enantiomer is present in a ratio (mutatis mutandis:purity) of at least 70:30, and notably of at least 90:10 (mutatis mutandis:purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

The term "halogen" means fluorine, chlorine, or bromine, preferably fluorine or chlorine.

The term "alkyl", used alone or in combination, refers to a straight or branched saturated hydrocarbon chain containing one to four carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of $(C_{1-4})$alkyl groups are methyl, ethyl, n-propyl, iso-propyl, n-butyl, iso-butyl, sec.-butyl and tert.-butyl. Examples of $(C_{1-3})$alkyl groups are methyl, ethyl, n-propyl and iso-propyl. Examples of $(C_{1-2})$alkyl groups are methyl and ethyl. In case $R^1$ represents "$(C_{x-y})$alkyl" the term means preferably methyl, ethyl and n-propyl, and more preferably ethyl and n-propyl. In case $R^1$ represents "$(C_{x-y})$alkyl which is mono-substituted with $-NR^7R^8$" the term "$(C_{x-y})$alkyl" means preferably ethyl. In case $R^3$ represents "$(C_{x-y})$alkyl" the term means preferably methyl and ethyl, and more preferably methyl. In case $R^4$ represents "$(C_{x-y})$alkyl" the term means preferably methyl and ethyl, and more preferably methyl. In case $R^4$ represents "$(C_{x-y})$alkyl which is mono-substituted with hydroxy" the term "$(C_{x-y})$alkyl" means preferably methyl or iso-propyl and more preferably methyl. In case $R^4$ represents "$(C_{x-y})$alkyl which is mono-substituted with $-NR^7R^8$" the term "$(C_{x-y})$alkyl" means preferably methyl. In case $R^5$ represents "$(C_{x-y})$alkyl" the term means preferably methyl and ethyl, and more preferably methyl. In case $R^5$ represents "$(C_{x-y})$alkyl which is mono-substituted with hydroxy" the term "$(C_{x-y})$alkyl" means preferably methyl. In case $R^6$ represents "$(C_{x-y})$alkyl" the term means preferably methyl. In case $R^7$ represents "$(C_{x-y})$alkyl" the term means preferably methyl. In case $R^8$ represents "$(C_{x-y})$alkyl" the term means preferably methyl. In case a "$(C_{x-y})$alkyl" group is a substituent to a "heterocyclyl group" representing "$R^1$", the term "$(C_x-C_y)$alkyl" means preferably methyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, iso-propoxy, n-butoxy, iso-butoxy, sec.-butoxy and tert.-butoxy. Examples of $(C_{1-3})$alkoxy groups are methoxy, ethoxy, n-propoxy and iso-propoxy. Examples of $(C_{2-3})$alkoxy groups are ethoxy, n-propoxy and iso-propoxy. Examples of $(C_{1-2})$alkoxy groups are methoxy and ethoxy. In case $R^1$ represents "$(C_{x-y})$alkoxy" the term means preferably methoxy, ethoxy and iso-propoxy and more preferably ethoxy. In case $R^2$ represents "$(C_{x-y})$alkoxy" the term means preferably ethoxy. In case $R^1$ represents "$(C_{x-y})$alkoxy which is mono-substituted with $-NR^7R^8$" the term "$(C_{x-y})$alkoxy" means preferably ethoxy; it is preferred that the oxygen-atom of the $(C_{x-y})$alkoxy group and the substituent $-NR^7R^8$ are attached to different carbon-atoms of the $(C_{x-y})$alkoxy group.

The term "$(C_{xa-ya})$alkoxy-$(C_{x-y})$alkoxy" (x, xa, y and ya each being an integer) refers to an alkoxy group as defined before containing x to y carbon atoms wherein one hydrogen atom has been replaced with $(C_{xa-ya})$alkoxy as defined before containing xa to ya carbon atoms. For example a "$(C_{1-2})$alkoxy-$(C_{2-3})$alkoxy group" refers to an $(C_{2-3})$alkoxy group as defined before containing two or three carbon atoms wherein one hydrogen atom has been replaced with $(C_{1-2})$alkoxy as defined before containing one or two carbon atoms. It is preferred that the oxygen-atom of the $(C_{x-y})$alkoxy group and the oxygen-atom of the $(C_{xa-ya})$alkoxy group are attached to different carbon-atoms of the $(C_{x-y})$alkoxy group. Representative examples of $(C_{1-2})$alkoxy-$(C_{2-3})$alkoxy groups include 2-methoxy-ethoxy, 1-methoxy-prop-2-oxy, 2-methoxy-prop-1-oxy, 3-methoxy-prop-1-oxy, 2-ethoxy-ethoxy, 1-ethoxy-prop-2-oxy, 2-ethoxy-prop-1-oxy and 3-ethoxy-prop-1-oxy. In case $R^1$ represents "$(C_{1-2})$alkoxy-$(C_{2-3})$alkoxy" the term means preferably 2-methoxy-ethoxy and 2-ethoxy-ethoxy and more preferably 2-methoxy-ethoxy.

The term "$(C_{1-3})$fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of $(C_{1-3})$fluoroalkyl groups include difluoromethyl, trifluoromethyl, 2-fluoroethyl, 2,2-difluoroethyl, and 2,2,2-trifluoroethyl. Another representative example of $(C_{1-3})$fluoroalkyl is 1,1-difluoroethyl. Preferred are $(C_1)$fluoroalkyl groups such as trifluoromethyl or difluoromethyl. In case $R^1$ represents "$(C_{x-y})$fluoroalkyl" the term means preferably trifluoromethyl and 1,1-difluoroethyl and more preferably trifluoromethyl.

The term "$(C_{1-3})$fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of $(C_{1-3})$fluoroalkoxy groups include trifluoromethoxy, difluoromethoxy and 2,2,2-trifluoroethoxy. In case $R^1$ represents "$(C_{x-y})$fluoroalkoxy" the term means preferably 2,2,2-trifluoroethoxy.

The term "cycloalkyl", used alone or in combination, refers to a saturated carbocyclic ring containing three to six carbon atoms. The term "$(C_{x-y})$cycloalkyl" (x and y each being an integer), refers to a cycloalkyl group as defined before containing x to y carbon atoms. For example a ($C_{3-6}$)cycloalkyl group contains from three to six carbon atoms. Examples of cycloalkyl groups are cyclopropyl, cyclobutyl, cyclopentyl, and cyclohexyl. In case $R^1$ represents "($C_{x-y}$)cycloalkyl" the term means preferably cyclopropyl.

The term "cycloalkoxy", used alone or in combination, refers to a cycloalkyl-O— group wherein the cycloalkyl group is as defined before. The term "($C_{x-y}$)cycloalkoxy" (x and y each being an integer) refers to a cycloalkoxy group as defined before containing x to y carbon atoms. For example a ($C_{3-6}$)cycloalkoxy group means a group of the formula ($C_{3-6}$)cycloalkyl-O— in which the term "($C_{3-6}$) cycloalkyl" has the previously given significance. Examples of ($C_{3-6}$)cycloalkoxy groups are cyclopropyloxy, cyclobutyloxy, cyclopentyloxy, and cyclohexyloxy. In case $R^1$ represents "($C_{x-y}$)cycloalkoxy" the term means preferably cyclobutyloxy.

The term "heterocyclyl", wherein the "heterocyclyl is a 4- to 6-membered mono-cyclic saturated ring containing one or two heteroatoms independently selected from nitrogen and oxygen", as used for substituents $R^1$, means for example azetidinyl, pyrrolidinyl, piperidinyl, piperazinyl, morpholinyl, tetrahydrofuranyl and tetrahydropyranyl groups, and preferably pyrrolidinyl and piperazinyl groups; wherein said heterocyclyl is unsubstituted or mono-substituted with ($C_{1-2}$)alkyl. Particular examples are pyrrolidin-1-yl, and 4-methyl-piperazin-1-yl.

The term "heterocyclyloxy", used alone or in combination, refers to a heterocyclyl-O— group; the term "heterocyclyloxy", wherein the "heterocyclyl is a 4- to 6-membered mono-cyclic saturated ring containing one oxygen atom", as used for substituents $R^1$, means for example oxetanyloxy, tetrahydrofuranyloxy and tetrahydropyranyloxy groups, and preferably an oxetan-3-yloxy group.

1P) A further embodiment of the invention relates to compounds of Formula (I) according to embodiment 1) which are also compounds of Formula ($I_P$)

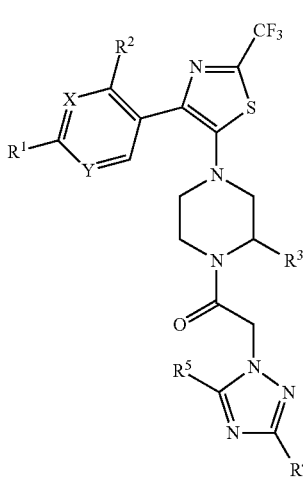

Formula ($I_P$)

wherein
X represents N or CH;
Y represents N or $CR^6$;
$R^1$ represents ($C_{1-4}$)alkyl; ($C_{3-6}$)cycloalkyl; ($C_{1-4}$)alkoxy; ($C_{3-6}$)cycloalkoxy; ($C_{1-3}$)fluoroalkyl; ($C_{1-3}$)fluoroalkoxy; halogen; cyano; ($C_{1-2}$)alkoxy-($C_{2-3}$)alkoxy; ($C_{1-3}$)alkyl which is mono-substituted with —$NR^7R^8$; ($C_{2-3}$)alkoxy which is mono-substituted with —$NR^7R^8$; heterocyclyl, wherein the heterocyclyl is a 4- to 6-membered mono-cyclic saturated ring containing one or two heteroatoms independently selected from nitrogen and oxygen and wherein said heterocyclyl is unsubstituted or mono-substituted with ($C_{1-2}$)alkyl; or heterocyclyloxy, wherein the heterocyclyl is a 4- to 6-membered mono-cyclic saturated ring containing one oxygen atom;
$R^2$ represents hydrogen, ($C_{1-4}$)alkoxy or fluoro;
$R^3$ represents hydrogen or methyl;
$R^4$ represents ($C_{1-4}$)alkyl, or ($C_{1-2}$)alkyl which is mono-substituted with —$NR^7R^8$;
$R^5$ represents ($C_{1-4}$)alkyl;
$R^6$ represents hydrogen, ($C_{1-4}$)alkyl or fluoro; or $R^1$ and $R^6$ form, together with the carbon atoms to which they are attached, a 5- or 6-membered heterocyclic ring, wherein the moiety needed to complete said heterocyclic ring is selected from —$OCH_2CH_2$—*, —$OCH_2O$—*, —$OCH_2CH_2CH_2$—* and —$OCH_2CH_2O$—*, wherein the asterisks indicate the bond which is linked to the $R^6$ bearing carbon atom;
$R^7$ represents ($C_{1-2}$)alkyl; and
$R^8$ represents ($C_{1-2}$)alkyl;
and to the salts (in particular pharmaceutically acceptable salts) of such compounds.

2) A further embodiment of the invention relates to compounds of formula (I) according to any one of embodiments 1) or 1P), wherein
X represents N or CH;
Y represents N or $CR^6$;
$R^1$ represents ($C_{1-3}$)alkyl; cyclopropyl; ($C_{1-3}$)alkoxy; cyclobutyloxy; trifluoromethyl; trifluoromethoxy; 2,2,2-trifluoroethoxy; chloro; cyano; 2-methoxy-ethoxy; pyrrolidin-1-yl; 4-methyl-piperazin-1-yl; or oxetan-3-yloxy;
$R^2$ represents hydrogen or ethoxy;
$R^3$ represents hydrogen or methyl;
$R^4$ represents methyl or ethyl;
$R^5$ represents methyl or ethyl; and
$R^6$ represents hydrogen or fluoro; or $R^1$ and $R^6$ form, together with the carbon atoms to which they are attached, a 5- or 6-membered heterocyclic ring, wherein the moiety needed to complete said heterocyclic ring is selected from —$OCH_2CH_2$—* and —$OCH_2CH_2CH_2$—*, wherein the asterisks indicate the bond which is linked to the $R^6$ bearing carbon atom;
and to the salts (in particular pharmaceutically acceptable salts) of such compounds.

3) A further embodiment of the invention relates to compounds of formula (I) according to any one of embodiments 1), 1P) or 2), wherein
$R^1$ represents ethyl; n-propyl; cyclopropyl; ethoxy; isopropoxy; cyclobutyloxy; trifluoromethyl; trifluoromethoxy; or 2,2,2-trifluoroethoxy;
and to the salts (in particular pharmaceutically acceptable salts) of such compounds.

4) A further embodiment of the invention relates to compounds of formula (I) according to any one of embodiments 1) or 1P) to 3), wherein
$R^2$ represents hydrogen;
and to the salts (in particular pharmaceutically acceptable salts) of such compounds.

5) A further embodiment of the invention relates to compounds of formula (I) according to any one of embodiments 1) or 1P) to 4), wherein
$R^4$ and $R^5$ represent methyl;
and to the salts (in particular pharmaceutically acceptable salts) of such compounds.

6) A further embodiment of the invention relates to compounds of formula (I) according to any one of embodiments 1) or 1P) to 5), wherein $R^6$ represents hydrogen;

and to the salts (in particular pharmaceutically acceptable salts) of such compounds.

7) A further embodiment of the invention relates to compounds of formula (I) according to any one of embodiments 1), 1P) or 3) to 5), wherein $R^1$ and $R^6$ form, together with the carbon atoms to which they are attached, a 5- or 6-membered heterocyclic ring, wherein the moiety needed to complete said heterocyclic ring is selected from —OCH$_2$CH$_2$—*, —OCH$_2$O—*, —OCH$_2$CH$_2$CH$_2$—* and —OCH$_2$CH$_2$O—*, wherein the asterisks indicate the bond which is linked to the $R^6$ bearing carbon atom;

and to the salts (in particular pharmaceutically acceptable salts) of such compounds.

8) A further embodiment of the invention relates to compounds of Formula (I) according to any one of embodiments 1) or 1P) which are also compounds of Formula (II)

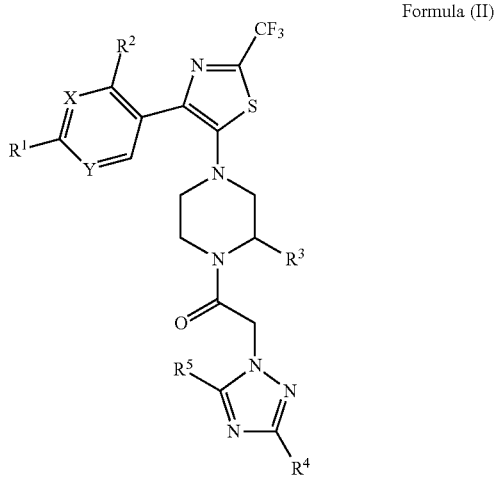

Formula (II)

wherein

X represents N or CH;

$R^1$ represents (C$_{1-4}$)alkyl; (C$_{3-6}$)cycloalkyl; (C$_{1-4}$)alkoxy; (C$_{3-6}$)cycloalkoxy; (C$_{1-3}$)fluoroalkyl; (C$_{1-3}$)fluoroalkoxy; (C$_{1-2}$)alkoxy-(C$_{2-3}$)alkoxy; (C$_{1-3}$)alkyl which is mono-substituted with —NR$^7$R$^8$; (C$_{2-3}$)alkoxy which is mono-substituted with —NR$^7$R$^8$; heterocyclyl, wherein the heterocyclyl is a 4- to 6-membered mono-cyclic saturated ring containing one or two heteroatoms independently selected from nitrogen and oxygen and wherein said heterocyclyl is unsubstituted or mono-substituted with (C$_{1-2}$)alkyl; or heterocyclyloxy, wherein the heterocyclyl is a 4- to 6-membered mono-cyclic saturated ring containing one oxygen atom;

$R^2$ represents hydrogen or (C$_{1-4}$)alkoxy;

$R^3$ represents hydrogen or methyl;

$R^4$ represents (C$_{1-4}$)alkyl, or (C$_{1-2}$)alkyl which is mono-substituted with —NR$^7$R$^8$;

$R^5$ represents (C$_{1-4}$)alkyl;

$R^7$ represents (C$_{1-2}$)alkyl; and $R^8$ represents (C$_{1-2}$)alkyl;

and to the salts (in particular pharmaceutically acceptable salts) of such compounds.

9) A further embodiment of the invention relates to compounds of Formula (II) according to embodiment 8), wherein X represents N or CH;

$R^1$ represents (C$_{1-4}$)alkyl; (C$_{3-6}$)cycloalkyl; (C$_{1-4}$)alkoxy; (C$_{3-6}$)cycloalkoxy; (C$_{1-2}$)fluoroalkyl; or (C$_{1-2}$)fluoroalkoxy;

$R^2$ represents hydrogen or ethoxy;

$R^3$ represents hydrogen or methyl;

$R^4$ represents methyl or ethyl; and $R^5$ represents methyl or ethyl;

and to the salts (in particular pharmaceutically acceptable salts) of such compounds.

10) A further embodiment of the invention relates to compounds of Formula (II) according to any one of embodiments 8) or 9), wherein X represents N;

and to the salts (in particular pharmaceutically acceptable salts) of such compounds.

11) A further embodiment of the invention relates to compounds of Formula (II) according to any one of embodiments 8) to 10), wherein $R^1$ represents ethyl; n-propyl; cyclopropyl; ethoxy; iso-propoxy; cyclobutyloxy; trifluoromethyl; or 2,2,2-trifluoroethoxy;

and to the salts (in particular pharmaceutically acceptable salts) of such compounds.

12) A further embodiment of the invention relates to compounds of Formula (II) according to any one of embodiments 8) to 11), wherein $R^3$ represents methyl;

and to the salts (in particular pharmaceutically acceptable salts) of such compounds.

13) A further embodiment of the invention relates to compounds of Formula (I) according to any one of embodiments 1) or 1P) which are also compounds of Formula (III)

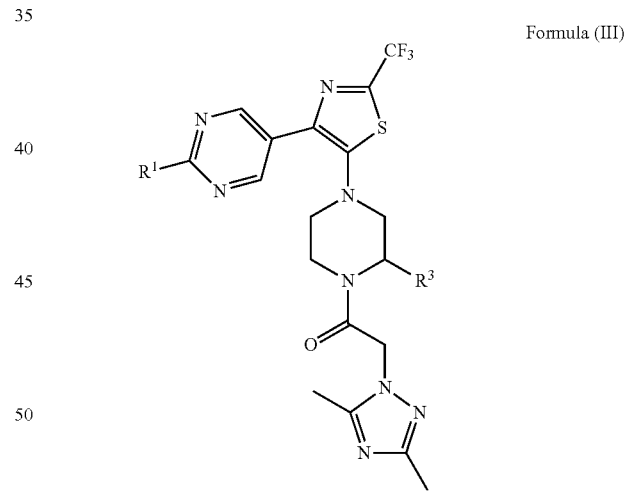

Formula (III)

wherein $R^1$ represents (C$_{1-4}$)alkyl; (C$_{3-6}$)cycloalkyl; (C$_{1-4}$)alkoxy; (C$_{3-6}$)cycloalkoxy; (C$_{1-2}$)fluoroalkyl; or (C$_{1-2}$)fluoroalkoxy; and $R^3$ represents hydrogen or methyl;

and to the salts (in particular pharmaceutically acceptable salts) of such compounds.

14) A further embodiment of the invention relates to compounds of Formula (III) according to embodiment 13), wherein $R^1$ represents ethyl; n-propyl; cyclopropyl; ethoxy; iso-propoxy; cyclobutyloxy; trifluoromethyl; or 2,2,2-trifluoroethoxy;

and to the salts (in particular pharmaceutically acceptable salts) of such compounds.

15) A further embodiment of the invention relates to compounds of Formula (III) according to embodiment 13), wherein $R^1$ represents $(C_{1-4})$alkoxy; or $(C_{1-2})$fluoroalkyl; and to the salts (in particular pharmaceutically acceptable salts) of such compounds.

16) A further embodiment of the invention relates to compounds of Formula (III) according to embodiment 13), wherein $R^1$ represents ethoxy; or trifluoromethyl;
and to the salts (in particular pharmaceutically acceptable salts) of such compounds.

17) A further embodiment of the invention relates to compounds of Formula (III) according to embodiment 13), wherein $R^1$ represents $(C_{1-4})$alkyl;
and to the salts (in particular pharmaceutically acceptable salts) of such compounds.

18) A further embodiment of the invention relates to compounds of Formula (III) according to embodiment 13), wherein $R^1$ represents $(C_{3-6})$cycloalkyl;
and to the salts (in particular pharmaceutically acceptable salts) of such compounds.

19) A further embodiment of the invention relates to compounds of Formula (III) according to embodiment 13), wherein $R^1$ represents $(C_{1-4})$alkoxy;
and to the salts (in particular pharmaceutically acceptable salts) of such compounds.

20) A further embodiment of the invention relates to compounds of Formula (III) according to embodiment 13), wherein $R^1$ represents $(C_{3-6})$cycloalkoxy;
and to the salts (in particular pharmaceutically acceptable salts) of such compounds.

21) A further embodiment of the invention relates to compounds of Formula (III) according to embodiment 13), wherein $R^1$ represents $(C_{1-2})$fluoroalkyl;
and to the salts (in particular pharmaceutically acceptable salts) of such compounds.

22) A further embodiment of the invention relates to compounds of Formula (III) according to embodiment 13), wherein $R^1$ represents $(C_{1-2})$fluoroalkoxy;
and to the salts (in particular pharmaceutically acceptable salts) of such compounds.

23) A further embodiment of the invention relates to compounds of Formula (III) according to any one of embodiments 13) to 22), wherein $R^3$ represents hydrogen;
and to the salts (in particular pharmaceutically acceptable salts) of such compounds.

24) A further embodiment of the invention relates to compounds of Formula (III) according to any one of embodiments 13) to 22), wherein $R^3$ represents methyl;
and to the salts (in particular pharmaceutically acceptable salts) of such compounds.

25) A further embodiment of the invention relates to compounds of Formula (I) according to any one of embodiments 1) or 1P) which are also compounds of Formula (IV)

Formula (IV)

wherein
$R^1$ represents $(C_{1-4})$alkyl; $(C_{1-4})$alkoxy; $(C_{1-3})$fluoroalkoxy; halogen; or cyano;
$R^2$ represents hydrogen or fluoro;
$R^3$ represents hydrogen or methyl; and
$R^6$ represents hydrogen, $(C_{1-4})$alkyl or fluoro; or $R^1$ and $R^6$ form, together with the carbon atoms to which they are attached, a 5- or 6-membered heterocyclic ring, wherein the moiety needed to complete said heterocyclic ring is selected from —OCH$_2$CH$_2$—*, —OCH$_2$O—*, —OCH$_2$CH$_2$CH$_2$—* and —OCH$_2$CH$_2$O—*, wherein the asterisks indicate the bond which is linked to the $R^6$ bearing carbon atom;
and to the salts (in particular pharmaceutically acceptable salts) of such compounds.

26) A further embodiment of the invention relates to compounds of Formula (IV) according to embodiment 25), wherein $R^2$ and $R^6$ represent hydrogen;
and to the salts (in particular pharmaceutically acceptable salts) of such compounds.

27) A further embodiment of the invention relates to compounds of Formula (IV) according to embodiment 25), wherein $R^2$ represents hydrogen; and
$R^1$ and $R^6$ form, together with the carbon atoms to which they are attached, a 5- or 6-membered heterocyclic ring, wherein the moiety needed to complete said heterocyclic ring is selected from —OCH$_2$CH$_2$—*, —OCH$_2$O—*, —OCH$_2$CH$_2$CH$_2$—* and —OCH$_2$CH$_2$O—*, wherein the asterisks indicate the bond which is linked to the $R^6$ bearing carbon atom;
and to the salts (in particular pharmaceutically acceptable salts) of such compounds.

28) A further embodiment of the invention relates to compounds of Formula (IV) according to any one of embodiments 25) to 27), wherein $R^3$ represents methyl;
and to the salts (in particular pharmaceutically acceptable salts) of such compounds.

29) A further embodiment of the invention relates to compounds of formula (I) according to any one of embodiments 1) or 1P) to 22) or 24) to 28), wherein, in case $R^3$ represents methyl, the carbon atom attached to $R^3$ is (R)-configurated;

and to the salts (in particular pharmaceutically acceptable salts) of such compounds.

30) A further embodiment of the invention relates to compounds of formula (I) according to any one of embodiments 1) or 1P) to 22) or 24) to 28), wherein, in case $R^3$ represents methyl, the carbon atom attached to $R^3$ is (S)-configurated;

and to the salts (in particular pharmaceutically acceptable salts) of such compounds.

31) Examples of compounds of formula (I) as defined in embodiment 1) are selected from the group consisting of:

2-(3,5-Dimethyl-[1,2,4]triazol-1-yl)-1-{(R)-4-[4-(4-methoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(4-iso-propoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-2-methyl-4-[4-(4-trifluoromethoxy-phenyl)-2-trifluoromethyl-thiazol-5-yl]-piperazin-1-yl}-ethanone;

2-(3,5-Dimethyl-[1,2,4]triazol-1-yl)-1-((R)-2-methyl-4-{4-[4-(2,2,2-trifluoro-ethoxy)-phenyl]-2-trifluoromethyl-thiazol-5-yl}-piperazin-1-yl)-ethanone;

4-(5-{(R)-4-[2-(3,5-Dimethyl-[1,2,4]triazol-1-yl)-acetyl]-3-methyl-piperazin-1-yl}-2-trifluoromethyl-thiazol-4-yl)-benzonitrile;

2-(3,5-Dimethyl-[1,2,4]triazol-1-yl)-1-{(R)-4-[4-(4-fluoro-phenyl)-2-trifluoromethyl-thiazol-5-yl]-2-methyl-piperazin-1-yl}-ethanone;

1-{(R)-4-[4-(4-Chloro-phenyl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-[(R)-2-methyl-4-(4-p-tolyl-2-trifluoromethyl-thiazol-5-yl)-piperazin-1-yl]-ethanone;

2-(3,5-Dimethyl-[1,2,4]triazol-1-yl)-1-{(R)-4-[4-(4-ethyl-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(3-fluoro-4-methoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(2-fluoro-4-methoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(4-methoxy-3-methyl-phenyl)-2-trifluoromethyl-thiazol-5-yl]-2-methyl-piperazin-1-yl}-ethanone;

1-[(R)-4-(4-Benzo[1,3]dioxol-5-yl-2-trifluoromethyl-thiazol-5-yl)-2-methyl-piperazin-1-yl]-2-(3,5-dimethyl-[1,2,4]triazol-1-yl)-ethanone;

1-{(R)-4-[4-(2,3-Dihydro-benzo[1,4]dioxin-6-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-4-[4-(6-ethoxy-pyridin-3-yl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(6-methoxy-pyridin-3-yl)-2-trifluoromethyl-thiazol-5-yl]-2-methyl-piperazin-1-yl}-ethanone;

2-(3-Dimethylaminomethyl-5-methyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone;

1-{(R)-4-[4-(2-Ethoxy-pyrimidin-5-yl)-2-trifluoromethyl-thiazol-5-yl]-2-methyl-piperazin-1-yl}-2-(3-ethyl-5-methyl-[1,2,4]triazol-1-yl)-ethanone;

1-{(R)-4-[4-(2-Ethoxy-pyrimidin-5-yl)-2-trifluoromethyl-thiazol-5-yl]-2-methyl-piperazin-1-yl}-2-(5-ethyl-3-methyl-[1,2,4]triazol-1-yl)-ethanone;

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone;

1-[(R)-4-(4-Chroman-6-yl-2-trifluoromethyl-thiazol-5-yl)-2-methyl-piperazin-1-yl]-2-(3,5-dimethyl-[1,2,4]triazol-1-yl)-ethanone;

2-(3,5-Dimethyl-[1,2,4]triazol-1-yl)-1-{(R)-2-methyl-4-[4-(2-propyl-pyrimidin-5-yl)-2-trifluoromethyl-thiazol-5-yl]-piperazin-1-yl}-ethanone;

2-(3,5-Dimethyl-[1,2,4]triazol-1-yl)-1-{(R)-2-methyl-4-[4-(2-methyl-pyrimidin-5-yl)-2-trifluoromethyl-thiazol-5-A-piperazin-1-yl}-ethanone;

2-(3,5-Dimethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(3,5-Di methyl-[1,2,4]triazol-1-yl)-1-((R)-4-{4-[2-(2-methoxy-ethoxy)-pyrimidin-5-yl]-2-trifluoromethyl-thiazol-5-yl}-2-methyl-piperazin-1-yl)-ethanone;

1-((R)-4-{4-[2-(2-Dimethylamino-ethoxy)-pyrimidin-5-yl]-2-trifluoromethyl-thiazol-5-yl}-2-methyl-piperazin-1-yl)-2-(3,5-dimethyl-[1,2,4]triazol-1-yl)-ethanone;

2-(3,5-Dimethyl-[1,2,4]triazol-1-yl)-1-{(R)-4-[4-(2-iso-propoxy-pyrimidin-5-yl)-2-trifluoromethyl-thiazol-5-yl]-2-methyl-piperazin-1-yl}-ethanone;

2-(3,5-Dimethyl-[1,2,4]triazol-1-yl)-1-((R)-2-methyl-4-{4-[2-(2,2,2-trifluoro-ethoxy)-pyrimidin-5-yl]-2-trifluoromethyl-thiazol-5-yl}-piperazin-1-yl)-ethanone;

1-{(R)-4-[4-(2,4-Diethoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-((R)-2-methyl-4-{4-[2-(oxetan-3-yloxy)-pyrimidin-5-yl]-2-trifluoromethyl-thiazol-5-yl}-piperazin-1-yl)-ethanone;

2-(3,5-Dimethyl-[1,2,4]triazol-1-yl)-1-{(R)-4-[4-(4-ethoxy-phenyl)-2-trifluoromethyl-thiazol-5-yl]-2-methyl-piperazin-1-yl}ethanone;

2-(3,5-Dimethyl-[1,2,4]triazol-1-yl)-1-{(R)-4-[4-(2-methoxy-pyrimidin-5-yl)-2-trifluoromethyl-thiazol-5-yl]-2-methyl-piperazin-1-yl}ethanone;

1-{(R)-4-[4-(2-Cyclopropyl-pyrimidin-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(S)-4-[4-(2-ethoxy-pyrimidin-5-yl)-2-trifluoromethyl-thiazol-5-yl]-2-methyl-piperazin-1-yl}ethanone;

2-(3,5-Dimethyl-[1,2,4]triazol-1-yl)-1-{4-[4-(2-ethoxy-pyrimidin-5-yl)-2-trifluoromethyl-thiazol-5-yl]piperazin-1-yl}ethanone;

2-(3,5-Dimethyl-[1,2,4]triazol-1-yl)-1-{(R)-2-methyl-4-[4-(2-pyrrolidin-1-yl-pyrimidin-5-yl)-2-trifluoromethyl-thiazol-5-yl]-piperazin-1-yl}ethanone;

2-(3,5-Dimethyl-[1,2,4]triazol-1-yl)-1-((R)-2-methyl-4-{4-[2-(4-methyl-piperazin-1-yl)-pyrimidin-5-yl]-2-trifluoromethyl-thiazol-5-yl}piperazin-1-yl)-ethanone;

1-{(R)-4-[4-(2-Cyclobutoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone;

1-{(R)-4-[4-(3,4-Dihydro-2H-pyrano[2,3-b]pyridin-6-yl)-2-trifluoromethyl-thiazol-5-yl]-2-methyl-piperazin-1-yl}-2-(3,5-dimethyl-[1,2,4]triazol-1-yl)-ethanone;

1-{(R)-4-[4-(2,3-Dihydro-benzofuran-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-2,2-dideuterium-ethanone;

1-((R)-4-{4-[2-(2-Dimethylamino-ethyl)-pyrimidin-5-yl]-2-trifluoromethyl-thiazol-5-yl}-2-methyl-piperazin-1-yl)-2-(3,5-dimethyl-[1,2,4]triazol-1-yl)-ethanone; and 2-(3,5-Dimethyl-[1,2,4]triazol-1-yl)-1-{(R)-4-[4-(2-ethyl-pyrimidin-5-yl)-2-trifluoromethyl-thiazol-5-yl]-2-methyl-piperazin-1-yl}ethanone;

or salts (in particular pharmaceutically acceptable salts) of such compounds.

32) Preferred examples of compounds of formula (I) as defined in embodiment 1) are selected from the group consisting of:

1-{(R)-4-[4-(2-Ethoxy-pyrimidin-5-yl)-2-trifluoromethyl-thiazol-5-yl]-2-methyl-piperazin-1-yl}-2-(3-ethyl-5-methyl-[1,2,4]triazol-1-yl)-ethanone;

1-{(R)-4-[4-(2-Ethoxy-pyrimidin-5-yl)-2-trifluoromethyl-thiazol-5-yl]-2-methyl-piperazin-1-yl}-2-(5-ethyl-3-methyl-[1,2,4]triazol-1-yl)-ethanone;

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}ethanone;

2-(3,5-Dimethyl-[1,2,4]triazol-1-yl)-1-{(R)-2-methyl-4-[4-(2-propyl-pyrimidin-5-yl)-2-trifluoromethyl-thiazol-5-yl]-piperazin-1-yl}ethanone;

2-(3,5-Dimethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(3,5-Dimethyl-[1,2,4]triazol-1-yl)-1-{(R)-4-[4-(2-iso-propoxy-pyrimidin-5-yl)-2-trifluoromethyl-thiazol-5-yl]-2-methyl-piperazin-1-yl}-ethanone;

2-(3,5-Dimethyl-[1,2,4]triazol-1-yl)-1-((R)-2-methyl-4-{4-[2-(2,2,2-trifluoro-ethoxy)-pyrimidin-5-yl]-2-trifluoromethyl-thiazol-5-yl}-piperazin-1-yl)-ethanone;

1-{(R)-4-[4-(2-Cyclopropyl-pyrimidin-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(S)-4-[4-(2-ethoxy-pyrimidin-5-yl)-2-trifluoromethyl-thiazol-5-yl]-2-methyl-piperazin-1-yl}-ethanone;

2-(3,5-Dimethyl-[1,2,4]triazol-1-yl)-1-{4-[4-(2-ethoxy-pyrimidin-5-yl)-2-trifluoromethyl-thiazol-5-yl]-piperazin-1-yl}-ethanone;

1-{(R)-4-[4-(2-Cyclobutoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone; and 2-(3,5-Dimethyl-[1,2,4]triazol-1-yl)-1-{(R)-4-[4-(2-ethyl-pyrimidin-5-yl)-2-trifluoromethyl-thiazol-5-yl]-2-methyl-piperazin-1-yl}-ethanone;

or salts (in particular pharmaceutically acceptable salts) of such compounds.

33) A further embodiment of the invention relates to compounds of Formula (I) according to embodiment 1) which are also compounds of Formula (V)

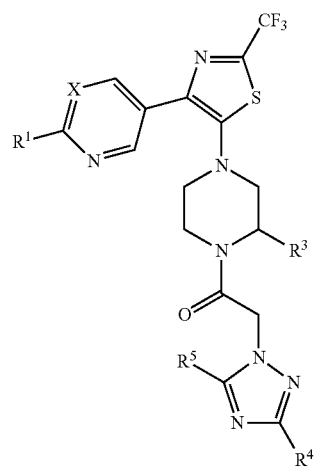

Formula (V)

wherein
X represents N or CH;
$R^1$ represents $(C_{1-4})$alkyl, $(C_{3-6})$cycloalkyl, $(C_{1-4})$alkoxy, $(C_{3-6})$cycloalkoxy, $(C_{1-3})$fluoroalkyl, or $(C_{1-3})$fluoroalkoxy;
$R^3$ represents hydrogen, or $(C_{1-4})$alkyl;
$R^4$ represents $(C_{1-4})$alkyl, or $(C_{1-4})$alkyl which is mono-substituted with hydroxy;
$R^5$ represents $(C_{1-4})$alkyl, or $(C_{1-4})$alkyl which is mono-substituted with hydroxy;
and to the salts (in particular pharmaceutically acceptable salts) of such compounds.

34) A further embodiment of the invention relates to compounds of Formula (V) according to embodiment 33), wherein
X represents N;
and to the salts (in particular pharmaceutically acceptable salts) of such compounds.

35) A further embodiment of the invention relates to compounds of Formula (V) according to any one of embodiments 33) or 34), wherein
$R^1$ represents ethyl, n-propyl, cyclopropyl, ethoxy, iso-propoxy, cyclobutyloxy, trifluoromethyl, 1,1-difluoroethyl, or 2,2,2-trifluoroethoxy;
and to the salts (in particular pharmaceutically acceptable salts) of such compounds.

36) A further embodiment of the invention relates to compounds of Formula (V) according to any one of embodiments 33) or 34), wherein
$R^1$ represents ethoxy, trifluoromethyl, or 1,1-difluoroethyl;
and to the salts (in particular pharmaceutically acceptable salts) of such compounds.

37) A further embodiment of the invention relates to compounds of Formula (V) according to any one of embodiments 33) or 34), wherein
$R^1$ represents trifluoromethyl;
and to the salts (in particular pharmaceutically acceptable salts) of such compounds.

38) A further embodiment of the invention relates to compounds of Formula (V) according to any one of embodiments 33) to 37), wherein
$R^3$ represents hydrogen, methyl, or ethyl;
and to the salts (in particular pharmaceutically acceptable salts) of such compounds.

39) A further embodiment of the invention relates to compounds of Formula (V) according to any one of embodiments 33) to 37), wherein R³ represents methyl, or ethyl;
and to the salts (in particular pharmaceutically acceptable salts) of such compounds.

40) A further embodiment of the invention relates to compounds of Formula (V) according to any one of embodiments 33) to 39), wherein
R⁴ represents methyl, ethyl, hydroxy-methyl, or 2-hydroxy-prop-2yl;
and to the salts (in particular pharmaceutically acceptable salts) of such compounds.

41) A further embodiment of the invention relates to compounds of Formula (V) according to any one of embodiments 33) to 39), wherein
R⁴ represents methyl, or hydroxy-methyl;
and to the salts (in particular pharmaceutically acceptable salts) of such compounds.

42) A further embodiment of the invention relates to compounds of Formula (V) according to any one of embodiments 33) to 41), wherein
R⁵ represents methyl, ethyl, or hydroxy-methyl;
and to the salts (in particular pharmaceutically acceptable salts) of such compounds.

43) A further embodiment of the invention relates to compounds of Formula (V) according to any one of embodiments 33) to 41), wherein
R⁵ represents methyl, or hydroxy-methyl;
and to the salts (in particular pharmaceutically acceptable salts) of such compounds.

44) Further examples of compounds of formula (I) as defined in embodiment 1) are selected from the group consisting of:
2-(3-Hydroxymethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(5-Hydroxymethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(3-Ethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(5-Ethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-[3-(1-Hydroxy-1-methyl-ethyl)-5-methyl-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone;
2-(3,5-Dimethyl-[1,2,4]triazol-1-yl)-1-{(R)-2-methyl-4-[2-trifluoromethyl-4-(6-trifluoromethyl-pyridin-3-yl)-thiazol-5-yl]-piperazin-1-yl}-ethanone;
2-(3,5-Dimethyl-[1,2,4]triazol-1-yl)-1-{(S)-2-methyl-4-[2-trifluoromethyl-4-(2-trifluoromethyl-pyrimidin-5-yl)-thiazol-5-yl]-piperazin-1-yl}-ethanone;
2-(3,5-Dimethyl-[1,2,4]triazol-1-yl)-1-{(R)-2-ethyl-4-[2-trifluoromethyl-4-(2-trifluoromethyl-pyrimidin-5-yl)-thiazol-5-yl]-piperazin-1-yl}-ethanone; and
1-((R)-4-{4-[2-(1,1-Difluoro-ethyl)-pyrimidin-5-yl]-2-trifluoromethyl-thiazol-5-yl}-2-methyl-piperazin-1-yl)-2-(3,5-dimethyl-[1,2,4]triazol-1-yl)-ethanone;
or salts (in particular pharmaceutically acceptable salts) of such compounds.

45) The invention, thus, relates to compounds of the Formula (I) as defined in embodiment 1), compounds of the Formula (I$_P$) as defined in embodiment 1P), compounds of the Formula (II) as defined in embodiment 8), compounds of the Formula (III) as defined in embodiment 13), compounds of the formula (IV) as defined in embodiment 25), compounds of the formula (V) as defined in embodiment 33); and to such compounds further limited by the characteristics of any one of embodiments 2) to 7), 9) to 12), 14) to 24), 26) to 32), and 34) to 44), all under consideration of their respective dependencies; to pharmaceutically acceptable salts thereof; and to the use of such compounds as medicaments especially in the treatment of disorders relating to a dysfunction of the CXCR3 receptor or dysfunction of ligands signalling through CXCR3, such as especially autoimmune disorders, inflammatory diseases, infectious diseases, transplant rejection, fibrosis, neurodegenerative disorders and cancer. Especially the following embodiments relating to the compounds of formulae (I), (I$_P$), (II), (III), (IV), and (V) are thus possible and intended and herewith specifically disclosed in individualized form:

1, 1P+1, 2+1P+1, 3+1P+1, 3+2+1P+1, 4+1P+1, 4+2+1P+1, 4+3+1P+1, 4+3+2+1P+1, 5+1P+1, 5+2+1P+1, 5+3+1P+1, 5+3+2+1P+1, 5+4+1P+1, 5 4+2+1P+1, 5+4+3+1P+1, 5+4+3+2+1P+1, 6+1P+1, 6+2+1P+1, 6+3+1P+1, 6+3+2+1E+1, 6+4+1E+1, 6+4+2+1P+1, 6+4+3+1P+1, 6+4+3+2+1P+1, 6+5+1P+1, 6+5+2+1P+1, 6+5+3+1P+1, 6+5+3+2+1P+1, 6+5+4+1P+1, 6+5+4+2+1P+1, 6+5+4+3+1P+1, 6+5+4+3+2+1P+1, 7+1P+1, 7+3+1P+1, 7+3+2+1P+1, 7+4+1P+1, 7+4+2+1P+1, 7+4+3+1P+1, 7+4+3+2+1P+1, 7+5+1P+1, 7+5+2+1P+1, 7+5+3+1P+1, 7+5+3+2+1P+1, 7+5+4+1P+1, 7+5+4+2+1P+7+5+4+3+1P+1, 7+5+4+3+2+1P+1, 8+1P+1, 9+8+1P+1, 10+8+1P+1, 10+9+8+1P+1, 11+8+1P+1, 11+9+8+1P+1, 11+10+8+1P+1, 11+10+9+8+1P+1, 12+8+1P+1, 12+9+8+1P+1, 12+10+8+1P+1, 12+10+9+8+1P+1, 12+11+8+1P+1, 12+11+9+8+1P+1, 12+11+10+8+1P+1, 12+11+10+9+8+1P+1, 13+1P+1, 14+13+1P+1, 15+13+1P+1, 16+13+1P+1, 17+13+1P+1, 18+13+1P+1, 19+13+1P+1, 20+13+1P+1, 21+13+1P+1, 22+13+1P+1, 23+13+1P+1, 23+14+13+1P+1, 23+15+13+1P+1, 23+16+13+1P+1, 23+17+13+1P+1, 23+18+13+1P+1, 23+19+13+1P+1, 23+20+13+1P+1, 23+21+13+1P+1, 23+22+13+1P+1, 24+13+1P+1, 24+14+13+1P+1, 24+15+13+1P+1, 24+16+13+1P+1, 24+17+13+1P+1, 24+18+13+1P+1, 24+19+13+1P+1, 24+20+13+1P+1, 24+21+13+1P+1, 24+22+13+1P+1, 25+1P+1, 26+25+1P+1, 27+25+1P+1, 28+25+1P+1, 28+26+25+1P+1, 28+27+25+1P+1, 29+1P+1, 29+2+1P+1, 29+3+1P+1, 29+3+2+1P+1, 29+4+1E+1, 29+4+2+1P+1, 29+4+3+1P+1, 29+4+3+2+1P+1, 29+5+1P+1, 29+5+2+1P+1, 29+5+3+1P+1, 29+5+3+2+1P+1, 29+5+4+1P+1, 29+5+4+2+1P+1, 29+5+4+3+1P+1, 29+5+4+3+2+1P+1, 29+6+1P+1, 29+6+2+1P+1, 29+6+3+1P+1, 29+6+3+2+1P+1, 29+6+4+1P+1, 29+6+4+2+1P+1, 29+6+4+3+1P+1, 29+6+4+3+2+1P+1, 29+6+5+1P+1, 29+6+5+2+1P+1, 29+6+5+3+1P+1, 29+6+5+3+2+1P+1, 29+6+5+4+1P+1, 29+6+5+4+2+1E+1, 29+6+5+4+3+1P+1, 29+6+5+4+3+2+1P+1, 29+7+1P+1, 29+7+3+1P+1, 29+7+3+2+1P+1, 29+7+4+1P+1, 29+7+4+2+1P+1, 29+7+4+3+1P+1, 29+7+4+3+2+1P+1, 29+7+5+1F+1, 29+7+5+2+1P+1, 29+7+5+3+1P+1, 29+7+5+3+2+1P+1, 29+7+5+4+1P+29+7+5+4+2+1P+1, 29+7+5+4+3+1P+1, 29+7+5+4+3+2+1P+1, 29+8+1P+1, 29+9+8+1P+1, 29+10+8+1P+1, 29+10+9+8+1P+1, 29+11+8+1P+1, 29+11+9+8+1P+1, 29+11+10+8+1P+1, 29+11+10+9+8+1P+1, 29+12+8+1P+1, 29+12+9+8+1P+1, 29+12+10+8+1P+1, 29+12+10+9+8+1P+1, 29+12+11+8+1P+1, 29+12+11+9+8+1P+1, 29+12+11+10+8+1P+1, 29+12+11+10+9+8+1P+1, 29+13+1P+1, 29+14+13+1P+1, 29+15+13+1P+1, 29+16+13+1P+1, 29+17+13+1P+1, 29+18+13+1P+1, 29+19+13+1P+1, 29+20+13+1P+1, 29+21+13+1P+1, 29+22+13+1P+1, 29+24+13+1P+1, 29+24+14+13+1P+1, 29+24+15+13+1P+1, 29+24+16+13+1P+1, 29+24+17+13+1P+1, 29+24+18+13+1P+1, 29+24+19+13+1P+1, 29+24+20+13+1P+1, 29+24+21+13+1P+1, 29+24+22+13+1P+1,

29+25+1P+1, 29+26+25+1P+1, 20+27+25+1P+1, 29+28+25+1P+1, 29+28+26+25+1P+1, 29+28+27+25+1P+1, 30+1P+1, 30+2+1P+1, 30+3+1P+1, 30+3+2+1P+1, 30+4+1P+1, 30+4+2+1P+1, 30+4+3+1P+1, 30+4+3+2+1P+1, 30+5+1P+1, 30+5+2+1P+1, 30+5+3+1P+1, 30+5+3+2+1P+1, 30+5+4+1P+1, 30+5+4+2+1P+1, 30+5+4+3+1P+1, 30+5+4+3+2+1P+1, 30+6+1P+1, 30+6+2+1P+1, 30+6+3+1P+1, 30+6+3+2+1P+1, 30+6+4+1P+1, 30+6+4+2+1P+1, 30+6+4+3+1P+1, 30+6+4+3+2+1P+1, 30+8+5+1P+1, 30+6+5+2+1P+1, 30+6+5+3+1P+1, 30+6+5+3+2+1P+1, 30+6+5+4+1P+1, 30+6+5+4+2+1P+1, 30+6+5+4+3+1P+1, 30+6+5+4+3+2+1P+1, 30+7+1P+1, 30+7+3+1P+1, 30+7+3+2+1P+1, 30+7+4+1P+1, 30+7+4+2+1P+1, 30+7+4+3+1P+1, 30+7+4+3+2+1P+1, 30+7+5+1P+1, 30+7+5+2+1P+1, 30+7+5+3+1P+1, 30+7+5+3+2+1P+1, 30+7+5+4+1P+1, 30+7+5+4+2+1P+1, 30+7+5+4+3+1P+1, 30+7+5+4+3+2+1P+1, 30+8+1P+1, 30+9+8+1P+1, 30+10+8+1P+1, 30+10+9+8+1P+1, 30+11+8+1P+1, 30+11+9+8+1P+1, 30+11+10+8+1P+1, 30+11+10+9+8+1P+1, 30+12+8+1P+1, 30+12+9+8+1P+1, 30+12+10+8+1P+1, 30+12+10+9+8+1P+1, 30+12+11+8+1P+1, 30+12+11+9+8+1P+1, 30+12+11+10+8+1P+1, 30+12+11+10+9+8+1P+1, 30+13+1P+1, 30+14+13+1P+1, 30+15+13+1P+1, 30+16+13+1P+1, 30+17+13+1P+1, 30+18+13+1P+1, 30+19+13+1P+1, 30+20+13+1P+1, 30+21+13+1P+1, 30+22+13+1P+1, 30+24+13+1P+1, 30+24+14+13+1P+1, 30+24+15+13+1P+1, 30+24+16+13+1P+1, 30+24+17+13+1P+1, 30+24+18+13+1P+1, 30+24+19+13+1P+1, 30+24+20+13+1P+1, 30+24+21+13+1P+1, 30+24+22+13+1P+1, 30+25+1P+1, 30+26+25+1P+1, 30+27+25+1P+1, 30+28+25+1P+1, 30+28+26+25+1P+1, 30+28+27+25+1P+1, 31+1P+1, 32+1P+1, 33+1, 34+33+1, 35+33+1, 35+34+33+1, 36+33+1, 36+34+33+1, 37+33+1, 37+34+33+1, 38+33+1, 38+34+33+1, 38+35+33+1, 38+35+34+33+1, 38+36+33+1, 38+36+34+33+1, 38+37+33+1, 38+37+34+33+1, 39+33+1, 39+34+33+1, 39+35+33+1, 39+35+34+33+1, 39+36+33+1, 39+36+34+33+1, 39+37+33+1, 39+37+34+33+1, 40+33+1, 40+34+33+1, 40+35+33+1, 40+35+34+33+1, 40+36+33+1, 40+36+34+33+1, 40+37+33+1, 40+37+34+33+1, 40+38+33+1, 40+38+34+33+1, 40+38+35+33+1, 40+38+35+34+33+1, 40+38+36+33+1, 40+38+36+34+33+1, 40+38+37+33+1, 40+38+37+34+33+1, 40+39+33+1, 40+39+34+33+1, 40+39+35+33+1, 40+39+35+34+33+1, 40+39+36+33+1, 40+39+36+34+33+1, 40+39+37+33+1, 40+39+37+34+33+1, 41+33+1, 41+34+33+1, 41+35+33+1, 41+35+34+33+1, 41+36+33+1, 41+36+34+33+1, 41+37+33+1, 41+37+34+33+1, 41+38+33+1, 41+38+34+33+1, 41+33+35+33+1, 41+38+35+34+33+1, 41+38+36+33+1, 41+38+36+34+33+1, 41+38+37+33+1, 41+38+37+34+33+1, 41+39+33+1, 41+39+34+33+1, 41+39+35+33+1, 41+39+35+34+33+1, 41+39+36+33+1, 41+39+36+34+33+1, 41+39+37+33+1, 41+39+37+34+33+1, 42+33+1, 42+34+33+1, 42+35+33+1, 42+35+34+33+1, 42+36+33+1, 42+36+34+33+1, 42+37+33+1, 42+37+34+33+1, 42+38+33+1, 42+38+34+33+1, 42+38+35+33+1, 42+38+35+34+33+1, 42+38+36+33+1, 42+38+36+34+33+1, 42+38+37+33+1, 42+38+37+34+33+1, 42+39+33+1, 42+39+34+33+1, 42+38+35+33+1, 42+38+35+34+33+1, 42+39+36+33+1, 42+39+36+34+33+1, 42+39+37+33+1, 42+39+37+34+33+1, 42+40+33+1, 42+40+34+33+1, 42+40+35+33+1, 42+40+35+34+33+1, 42+40+36+33+1, 42+40+36+34+33+1, 42+40+37+33+1, 42+40+37+34+33+1, 42+40+38+33+1, 42+40+33+34+33+1, 42+40+38+35+33+1, 42+40+38+35+34+33+1, 42+40+38+36+33+1, 42+40+38+36+34+33+1, 42+40+38+37+33+1, 42+40+38+37+34+33+1, 42+40+39+33+1, 42+40+39+34+33+1, 42+40+39+35+33+1, 42+40+39+35+34+33+1, 42+40+39+36+33+1, 42+40+39+36+34+33+1, 42+40+39+37+33+1, 42+40+39+37+34+33+1, 42+41+33+1, 42+41+34+33+1, 42+41+35+33+1, 42+41+35+34+33+1, 42+41+36+33+1, 42+41+36+34+33+1, 42+41+37+33+1, 42+41+37+34+33+1, 42+41+38+33+1, 42+41+38+34+33+1, 42+41+38+35+33+1, 42+41+38+35+34+33+1, 42+41+38+36+33+1, 42+41+38+36+34+33+1, 42+41+38+37+33+1, 42+41+38+37+34+33+1, 42+41+39+33+1, 42+41+39+34+33+1, 42+41+39+35+33+1, 42+41+39+35+34+33+1, 42+41+39+36+33+1, 42+41+39+36+34+33+1, 42+41+39+37+33+1, 42+41+39+37+34+33+1, 43+33+1, 43+34+33+1, 43+35+33+1, 43+35+34+33+1, 43+36+33+1, 43+36+34+33+1, 43+37+33+1, 43+37+34+33+1, 43+38+33+1, 43+38+34+33+1, 43+38+35+33+1, 43+38+35+34+33+1, 43+38+36+33+1, 43+38+36+34+33+1, 43+38+37+33+1, 43+38+37+34+33+1, 43+39+33+1, 43+39+34+33+1, 43+39+35+33+1, 43+39+35+34+33+1, 43+39+36+33+1, 43+39+36+34+33+1, 43+39+37+33+1, 43+39+37+34+33+1, 43+40+33+1, 43+40+34+33+1, 43+40+35+33+1, 43+40+35+34+33+1, 43+40+36+33+1, 43+40+36+34+33+1, 43+40+37+33+1, 43+40+37+34+33+1, 43+40+38+33+1, 43+40+38+34+33+1, 43+40+38+35+33+1, 43+40+38+35+34+33+1, 43+40+38+36+33+1, 43+40+38+36+34+33+1, 43+40+38+37+33+1, 43+40+38+37+34+33+1, 43+40+39+33+1, 43+40+39+34+33+1, 43+40+39+35+33+1, 43+40+39+35+34+33+1, 43+40+39+36+33+1, 43+40+39+36+34+33+1, 43+40+39+37+33+1, 43+40+39+37+34+33+1, 43+41+33+1, 43+41+34+33+1, 43+41+35+33+1, 43+41+35+34+33+1, 43+41+36+33+1, 43+41+36+34+33+1, 43+41+37+33+1, 43+41+37+34+33+1, 43+41+38+33+1, 43+41+38+34+33+1, 43+41+38+35+33+1, 43+41+38+35+34+33+1, 43+41+38+36+33+1, 43+41+38+36+34+33+1, 43+41+38+37+33+1, 43+41+38+37+34+33+1, 43+41+39+33+1, 43+41+39+34+33+1, 43+41+39+35+33+1, 43+41+39+35+34+33+1, 43+41+39+36+33+1, 43+41+39+36+34+33+1, 43+41+39+37+33+1, 43+41+39+37+34+33+1, and 44+1; in the list above the numbers refer to the embodiments according to their numbering provided hereinabove whereas "+" indicates the dependency from another embodiment. The different individualized embodiments are separated by commas. In other words, "20+13+1P+1" for example refers to embodiment 20) depending on embodiment 13), depending on embodiment 1P), depending on embodiment 1), i.e. embodiment "20+13+1P+1" corresponds to the compounds of embodiment 1) further limited by the features of the embodiments 1P), 13) and 20).

Where the plural form is used for compounds, salts, pharmaceutical compositions, diseases or the like, this is intended to mean also a single compound, salt, disease or the like.

Any reference to a compound of Formula (I) as defined in any one of embodiments 1) to 45) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The present invention also includes isotopically labelled, especially $^2$H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

The compounds of formula (I) as defined in any one of embodiments 1) to 45) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of Formula (I) as defined in any one of embodiments 1) to 45).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

Another aspect of the invention concerns a method for the prevention or the treatment of a disease or disorder as mentioned above in a patient comprising the administration to said patient of a pharmaceutically active amount of a compound of Formula (I) as defined in any one of embodiments 1) to 45) or a pharmaceutically acceptable salt thereof.

The compounds according to Formula (I) as defined in any one of embodiments 1) to 45) are useful for the prevention or treatment of disorders relating to a dysfunction of the CXCR3 receptor or dysfunction of ligands signalling through CXCR3.

Such disorders relating to a dysfunction of the CXCR3 receptor or its ligands are diseases or disorders where a modulator of a human CXCR3 receptor is required. The above mentioned disorders may in particular be defined as comprising autoimmune disorders, inflammatory diseases, infectious diseases, transplant rejection, fibrosis, neurodegenerative disorders and cancer.

Autoimmune disorders may be defined as comprising rheumatoid arthritis (RA); multiple sclerosis (MS); inflammatory bowel disease (IBD; comprising Crohn's disease and ulcerative colitis); systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. In a sub-embodiment, autoimmune disorders include rheumatoid arthritis (RA); multiple sclerosis (MS); inflammatory bowel disease comprising Crohn's disease and ulcerative colitis; systemic lupus erythematosus (SLE); lupus nephritis; interstitial cystitis; celiac disease; and type I diabetes.

Inflammatory diseases may be defined as comprising asthma; COPD; atherosclerosis; myocarditis; dry eye disease (comprising Sjögren's dry eye syndrome); inflammatory myopathies; sarcoidosis; pulmonary arterial hypertension, especially associated with sarcoidosis; and obesity.

Infectious diseases may be defined as comprising diseases mediated by various infectious agents and complications resulting threrefrom; such as malaria, cerebral malaria, leprosy, tuberculosis, influenza, *toxoplasma gondii,* dengue, hepatitis B and C, herpes simplex, leishmania, *chlamydia trachomatis,* lyme disease, west nile virus.

Transplant rejection may be defined as comprising rejection of transplanted organs such as kidney, liver, heart, lung, pancreas, cornea, and skin; graft-versus-host diseases brought about by stem cell transplantation; and chronic allograft vasculopathy.

Fibrosis may be defined as comprising liver cirrhosis (comprising primary biliary cirrhosis (PBC) and autoimmune hepatitis), idiopathic pulmonary fibrosis, renal fibrosis, endomyocardial fibrosis, systemic sclerosis, and arthrofibrosis.

Neurodegenerative disorders may be defined as comprising neurodegeneration and conditions involving neuronal death such as multiple sclerosis (including relapsing remitting multiple sclerosis and progressive multiple sclerosis), Alzheimer's disease, Parkinson's disease, Huntington's chorea, HIV associated dementia, prion mediated neurodegeneration, epilepsy, stroke, cerebral ischemia, cerebral palsy, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, mild cognitive decline, cognitive decline, spinal muscular atrophy, and cerebral malaria. In another embodiment, neurodegenerative disorders may be defined as comprising in addition narcolepsy.

Cancer may be defined as comprising all sorts of cancers such as large intestine cancer, rectal cancer, breast cancer, lung cancer, non-small cell lung cancer, prostate cancer, esophagal cancer, stomach cancer, liver cancer, bile duct cancer, spleen cancer, kidney cancer, urinary bladder cancer, uterine cancer, ovarian cancer, cervical cancer, testicular cancer, thyroid cancer, pancreas cancer, brain tumor, blood tumor, basophil adenoma, prolactinoma, hyperprolactinemia, adenomas, endometrial cancer, colon cancer; chronic lymphocytic leukemia (CLL); and especially the metastatic spread of those cancers.

Especially, compounds of Formula (I) according to any one of embodiments 1) to 45), or pharmaceutically acceptable salts thereof, are suitable for the prevention or treatment of diseases selected from one, several or all of the following groups of diseases and disorders:

1) Autoimmune disorders selected from rheumatoid arthritis (RA); multiple sclerosis (MS); inflammatory bowel disease (IBD; comprising Crohn's disease and ulcerative colitis); systemic lupus erythematosus (SLE); psoriasis; lupus nephritis; and type I diabetes;
2) Inflammatory diseases selected from COPD; dry eye syndrome (comprising Sjögren's dry eye syndrome); myopathies (comprising inflammatory myopathies); and sarcoidosis;
3) Transplant rejection selected from graft-versus-host diseases;
4) Fibrosis selected from liver cirrhosis (comprising primary biliary cirrhosis (PBC) and autoimmune hepatitis); and
5) Neurodegenerative disorders selected from Guillain-Barré syndrome.

Preparation of Compounds of Formula (I)

A further aspect of the invention is a process for the preparation of compounds of Formula (I). Compounds according to Formula (I) of the present invention can be prepared from commercially available or well known starting materials according to the methods described in the experimental part; by analogous methods; or according to the general sequence of reactions outlined below, wherein X, Y, $R^1$, $R^2$, $R^3$, $R^4$, $R^5$, $R^6$, $R^7$ and $R^8$ are as defined for Formula (I). Other abbreviations used herein are explicitly defined, or are as defined in the experimental section. In some instances the generic groups $R^1$, $R^2$, $R^3$, $R^4$, $R^5$, $R^6$, $R^7$ and $R^8$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:

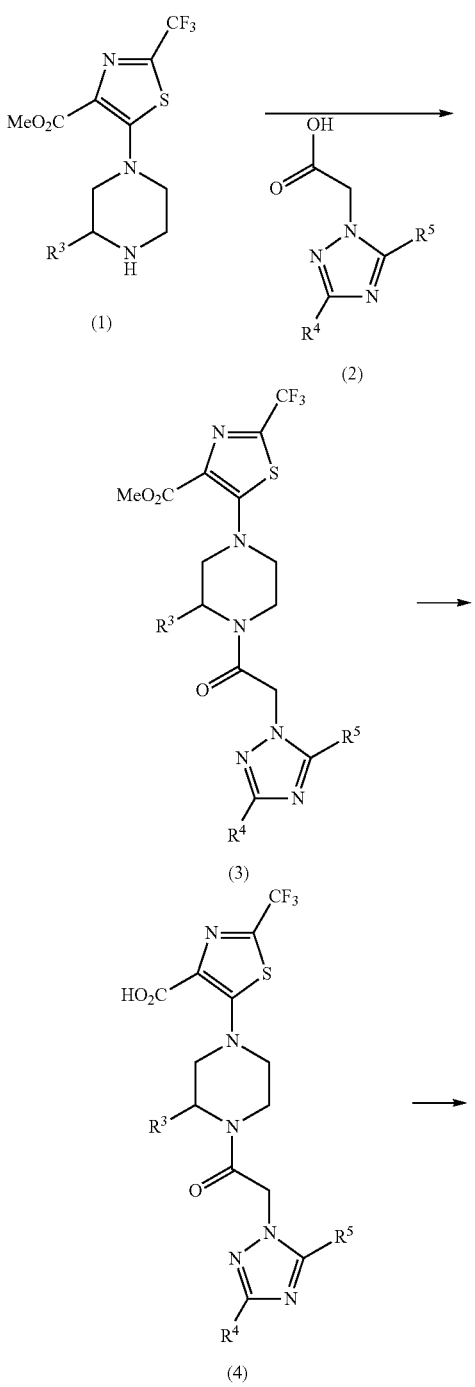

Scheme 2

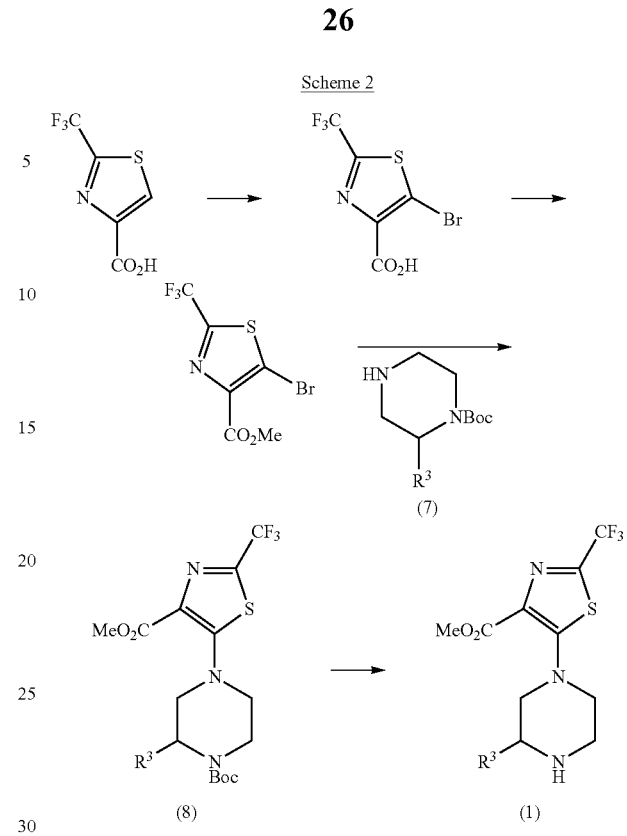

Compounds of structure (1) can be synthesized following the reaction sequence outlined in Scheme 2. 2-(Trifluoromethyl)thiazole-4-carboxylic acid is treated with n-butyl lithium and bromine in THF at a temperature around −78° C. The resulting brominated compound can be esterified using sulphuric acid in MeOH and heating at a temperature around 70° C. Nucleophilic aromatic substitution using commercially available piperazine derivatives (7), in presence of a suitable base such as DIPEA, in a suitable solvent such as MeCN, and at a temperature around 80° C. provides compound of structure (8). The Boc protecting group of the intermediate (8) can be subsequently cleaved under standard acidic conditions, preferably using HCl in a suitable solvent such as EA, dioxane, Et$_2$O, EtOH or a mixture thereof, or using TFA in DCM, and at a temperature about RT to give the compound of structure (1).

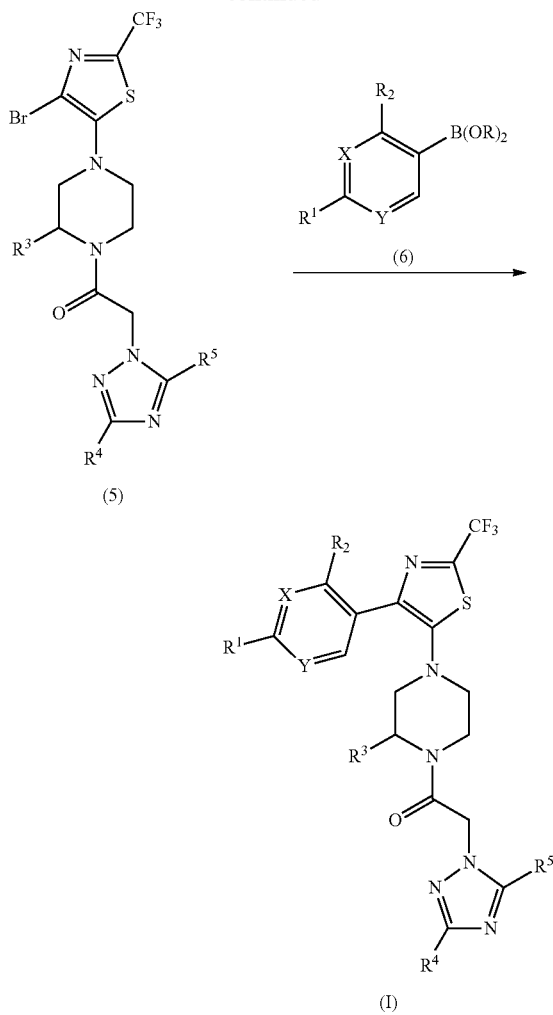

Compounds of Formula (I) can be synthesized starting (Scheme 1) from a compound of structure (1) by, in a first step, amide coupling with a carboxylic acid derivative (2) using standard peptide coupling methods such as HATU in presence of a suitable base such as DIPEA and in a suitable solvent such as DCM, preferably at a temperature about RT. The obtained compound of structure (3) is saponified in basic medium using standard conditions (e.g. aq. NaOH in MeOH) and the carboxylic group in the compound of structure (4) is converted to the corresponding brominated thiazole (5) using (diacetoxyiodo)benzene and LiBr in THF at RT. Alternatively, NBS and lithium acetate in THF at RT may be employed. Suzuki coupling is performed using a coupling partner of structure (6), wherein R represents hydrogen or alkyl, using standard conditions for a Suzuki reaction, in presence of a suitable base such as aq. Na$_2$CO$_3$, K$_2$CO$_3$ or K$_3$PO$_4$, in presence of a suitable palladium catalyst such as Pd$_2$(dba)$_3$ with tricyclohexylphosphine as ligand, Pd(PPh$_3$)$_4$ or Pd(PPh$_3$)$_2$Cl$_2$, in a suitable solvent such as MeCN or dioxane, and preferably heating between 80° C. and 100° C.

Scheme 3

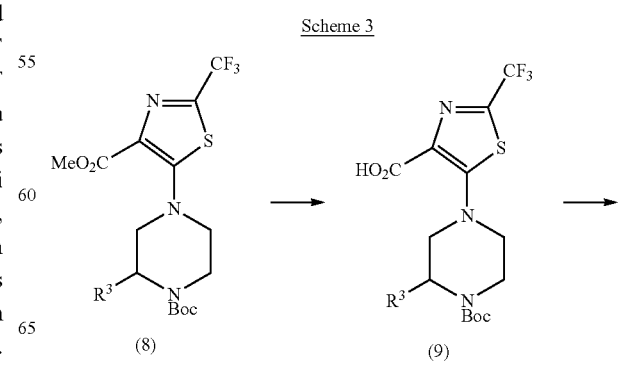

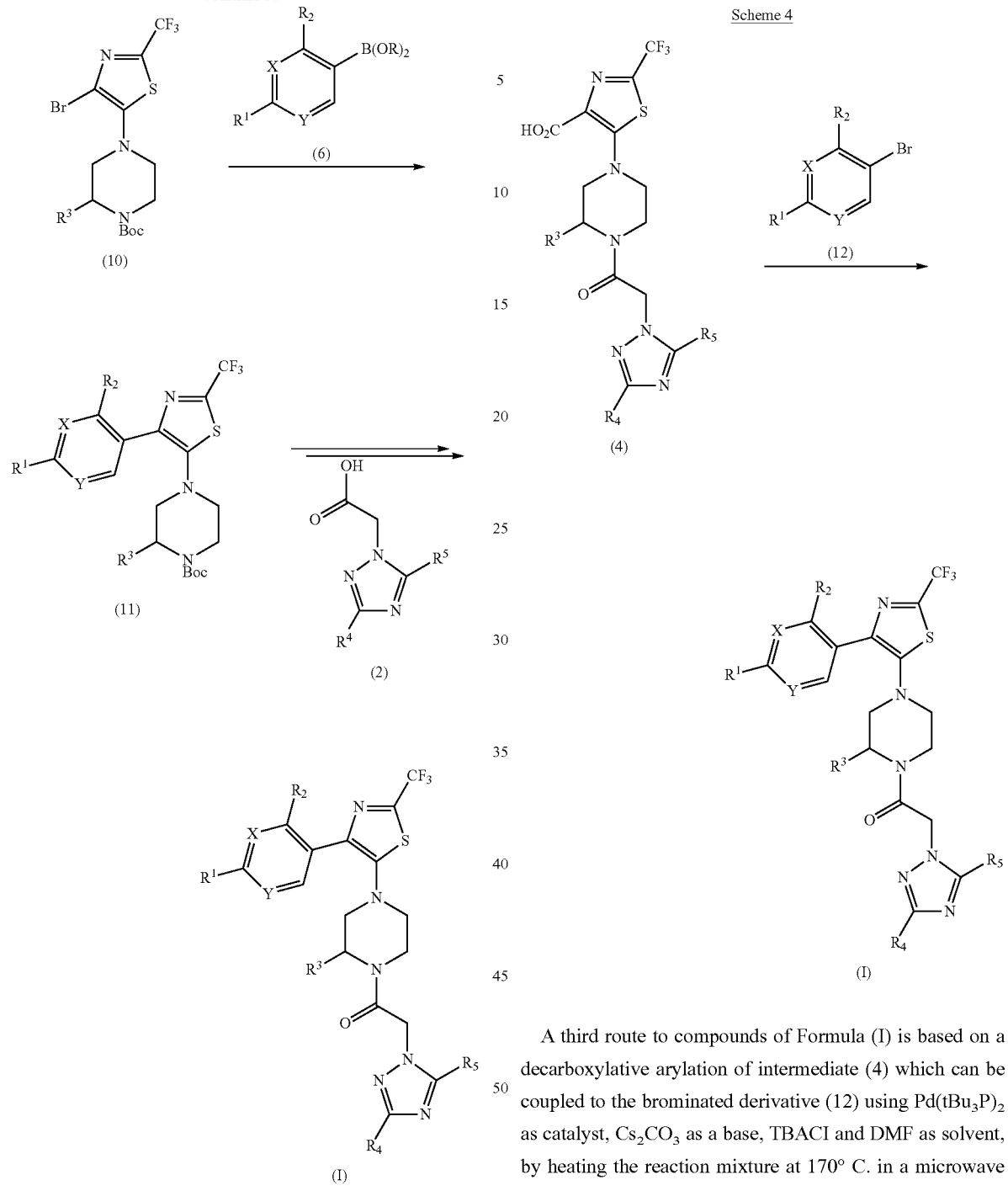

An alternative route to compounds of Formula (I) can be designed starting from intermediate (8), which is saponified under standard conditions (e.g. aq. NaOH in MeOH) to give compounds of structure (9) (Scheme 3). Conversion to the brominated thiazole (10) followed by Suzuki reaction to a compound of structure (11), Boc deprotection and final amide coupling provides the desired compounds of Formula (I) in synthetic steps already described in Scheme 1.

A third route to compounds of Formula (I) is based on a decarboxylative arylation of intermediate (4) which can be coupled to the brominated derivative (12) using Pd(tBu$_3$P)$_2$ as catalyst, Cs$_2$CO$_3$ as a base, TBACl and DMF as solvent, by heating the reaction mixture at 170° C. in a microwave oven (Scheme 4).

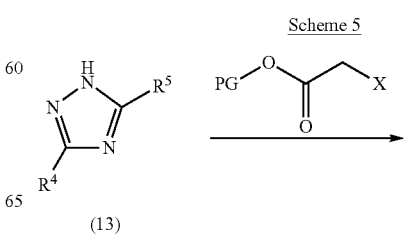

Scheme 5

The compounds of structure (2) are either commercially available, or can be synthesized following the route shown in Scheme 5. A compound of structure (13) can be alkylated using an acetic acid derivative of formula X—CH$_2$—COO (PG), wherein X is a leaving group such as bromine and PG is a protecting group suitable for an acid function (e.g. benzyl), in presence of a base such as Cs$_2$CO$_3$, in a suitable solvent such as MeCN, and at a temperature around RT. In case R$^4$ or R$^5$ represents (C$_{1-4}$)alkyl which is mono-substituted with hydroxy, the hydroxy group may be protected with a suitable protecting group such as TBS prior to alkylation with the acetic acid derivative of formula X—CH$_2$—COO(PG), which protecting group may be removed in the last step of the synthesis of compounds of formula (I) under conditions such as TBAF in THF at a temperature around RT.

Deprotection of the intermediate (14), such as benzyl deprotection under H$_2$, using Pd/C as catalyst and EtOH as solvent at a temperature around RT, leads to the compound of structure (2). Other suitable acid function protecting groups and protection and deprotection methods are well known to one skilled in the art (see notably "Protective groups in organic synthesis", Greene T. W. and Wuts P. G. M., Wiley-Interscience, 1999).

The compounds of structure (6),(12) and (13) are either commercially available or can be prepared in analogy to methods described in the experimental part. For instance, compounds of structure (6) may be prepared from compounds of structure (12) using triisopropyl borate and n-BuLi in THF and toluene at a temperature around −78° C.

Experimental Section:
Abbrevations (as used herein and in the description above):
aq. aqueous
Boc tert.-butyloxycarbonyl
BSA Bovine serum albumine
Bu butyl
CC column chromatography on silica gel
CHO Chinese hamster ovary
CV column volume
d doublet
dba dibenzylideneacetone
DCM dichloromethane
DEA diethylamine
DIPEA N-ethyldiisopropylamine
DMAP 4-Dimethylaminopyridine
DMF dimethylformamide
DMSO dimethylsulfoxide
Dppf 1,1'-bis(diphenylphosphanyl) ferrocene
EA ethyl acetate
EDTA ethylenediaminetetraacetic acid
EGTA ethylene glycol tetraacetic acid
Eq equivalent
Et ethyl
FBS fetal bovine serum
FLIPR Fluorescent imaging plate reader
Fluo-4-AM 2-{[2-(2-{5-[bis(carboxymethyl)amino]-2-methylphenoxy}ethoxy)-4-(2,7-difluoro-6-hydroxy-3-oxo-3H-xanthen-9-yl)phenyl]carboxymethyl)amino}acetic acid
G418 (2R,3S,4R,5R,6S)-5-amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol
h hour(s)
HATU 2-(7-Aza-1H-benzotriazole-1-yl)-1,1,3,3-tetramethyluronium hexafluorophosphate
HBSS Hank's balanced salt solution
HEPES 4-(2-hydroxyethyl)-piperazine-1-ethanesulfonic acid
Hep heptanes
HV High vacuum
HPLC high performance liquid chromatography
LC liquid chromatography
M molarity [mol L$^{-1}$]
Me methyl
MS mass spectroscopy
min minute(s)
N normality
NBS N-Bromosuccinimide
org. organic
Pd/C palladium on carbon
PG protecting group
Ph phenyl
rpm rotations per minute
RT room temperature
S singulet
sat. Saturated
sc subcutaneous
sec second(s)
TBACl Tetrabutylammonium chloride
TBAF Tetra-n-butylammonium fluoride
TBS tert-Butyldimethylsilyl
TFA trifluoroacetic acid
THF tetrahydrofuran
TLC Thin layer chromatography
t$_R$ retention time
UPLC Ultra performance liquid chromatography
I. Chemistry The following examples illustrate the preparation of biologically active compounds of the invention but do not at all limit the scope thereof.

General: All temperatures are stated in degrees Celsius (° C.). Unless otherwise indicated, the reactions take place at RT under an argon atmosphere and are run in a flame dried round-bottomed flask equipped with a magnetic stir bar.

Characterization Methods Used:

The LC-MS retention times have been obtained using the following elution conditions:

A) LC-MS (A):

Acquity UPLC BEH C18 1.7 μm 2.1×50 mm ID column from Waters, thermostated in the Acquity UPLC Column Manager (60° C.) was used. The two elution solvents were as follows: solvent A=water+0.05% formic acid; solvent B=MeCN+0.045% formic acid. The eluent flow rate was 1.0 mL/min and the characteristics of the eluting mixture proportion in function of the time t from start of the elution are summarized in the table below (a linear gradient being used between two consecutive time points):

|  | t (min) | | | | |
|---|---|---|---|---|---|
|  | 0 | 1.4 | 1.8 | 1.9 | 2.0 |
| Solvent A (%) | 98 | 5 | 2 | 2 | 98 |
| Solvent B (%) | 2 | 95 | 98 | 98 | 2 |

B) LC-MS (B):

Zorbax SB-Aq, 3.5 μm, 4.6×50 mm column thermostated at 40° C. The two elution solvents were as follows: solvent A=water+0.04% TFA; solvent B=MeCN. The eluent flow rate was 4.5 mL/min and the characteristics of the eluting mixture proportion in function of the time t from start of the elution are summarized in the table below (a linear gradient being used between two consecutive time points):

|  | t (min) | | | |
|---|---|---|---|---|
|  | 0 | 1.0 | 1.45 | 1.55 |
| Solvent A (%) | 95 | 5 | 5 | 95 |
| Solvent B (%) | 5 | 95 | 95 | 5 |

C) LC-MS (C):

Acquity UPLC HSS T3 C18 1.8 μm 2.1×50 mm ID column from Waters, thermostated in the Acquity UPLC Column Manager (60° C.) was used. The two elution solvents were as follows: solvent A=water+0.05% formic acid; solvent B=MeCN+0.045% formic acid. The eluent flow rate was 1 mL/min and the characteristics of the eluting mixture proportion in function of the time t from start of the elution are summarized in the table below (a linear gradient being used between two consecutive time points):

|  | t (min) | | | | |
|---|---|---|---|---|---|
|  | 0 | 1.4 | 1.8 | 1.9 | 2.0 |
| Solvent A (%) | 98 | 5 | 2 | 2 | 98 |
| Solvent B (%) | 2 | 95 | 98 | 98 | 2 |

D) LC-MS (D):

Acquity UPLC HSS T3 C18 1.8 μm 2.1×50 mm ID column from Waters, thermostated in the Acquity UPLC Column Manager (60° C.) was used. The two elution solvents were as follows: solvent A=water+0.05% TFA; solvent B=MeCN+0.045% TFA. The eluent flow rate was 1 mL/min and the characteristics of the eluting mixture proportion in function of the time t from start of the elution are summarized in the table below (a linear gradient being used between two consecutive time points):

|  | t (min) | | | | |
|---|---|---|---|---|---|
|  | 0 | 1.4 | 1.8 | 1.9 | 2.0 |
| Solvent A (%) | 98 | 5 | 2 | 2 | 98 |
| Solvent B (%) | 2 | 95 | 98 | 98 | 2 |

E) LC-MS (E):

Acquity UPLC CSH C18 1.7 μm 2.1×50 mm ID column from Waters, thermostated in the Acquity UPLC Column Manager (60° C.) was used. The two elution solvents were as follows: solvent A=water+0.05% formic acid; solvent B=MeCN+0.045% formic acid. The eluent flow rate was 1 mL/min and the characteristics of the eluting mixture proportion in function of the time t from start of the elution are summarized in the table below (a linear gradient being used between two consecutive time points):

|  | t (min) | | | | |
|---|---|---|---|---|---|
|  | 0 | 1.4 | 1.8 | 1.9 | 2.0 |
| Solvent A (%) | 98 | 5 | 2 | 2 | 98 |
| Solvent B (%) | 2 | 95 | 98 | 98 | 2 |

Preparative LC-MS Methods Used:

The purifications by preparative LC-MS have been performed using the conditions described hereafter.

I) Preparative LC-MS (I):

A X-Bridge column (Waters C18, 10 μm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
|---|---|---|---|---|---|---|
|  | 0 | 0.01 | 4.0 | 6.0 | 6.2 | 6.6 |
| Solvent A (%) | 80 | 80 | 5 | 5 | 80 | 80 |
| Solvent B (%) | 20 | 20 | 95 | 95 | 20 | 20 |

II) Preparative LC-MS (II):

A X-Bridge column (Waters C18, 10 μm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
|---|---|---|---|---|---|---|
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

III) Preparative LC-MS (III):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
|---|---|---|---|---|---|---|
|  | 0 | 0.01 | 4.0 | 6.0 | 6.2 | 6.6 |
| Solvent A (%) | 80 | 80 | 5 | 5 | 80 | 80 |
| Solvent B (%) | 20 | 20 | 95 | 95 | 20 | 20 |

IV) Preparative LC-MS (IV):

An Atlantis column (Waters T3, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 80 | 80 | 5 | 5 | 80 | 80 |
| Solvent B (%) | 20 | 20 | 95 | 95 | 20 | 20 |

V) Preparative LC-MS (V):

An Atlantis column (Waters T3, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

VI) Preparative LC-MS (VI):

A X-Bridge column (Waters C18, 5 μm OBD, 19×50 mm) was used. The two elution solvents were as follows: solvent A=water+0.1% $NH_4OH$ (25%); solvent B=MeCN+0.1% $NH_4OH$ (25%). The eluent flow rate was 40 mL/min and the characteristics of the eluting mixture proportion in function of the time t from start of the elution are summarized in the tables below (a linear gradient being used between two consecutive time points):

Gradient 1:

|  | t (min) | | | | | | |
| --- | --- | --- | --- | --- | --- | --- | --- |
|  | 0 | 0.2 | 0.3 | 4.4 | 4.5 | 5.6 | 5.7 |
| Solvent A (%) | 75 | 75 | 65 | 35 | 5 | 5 | 95 |
| Solvent B (%) | 25 | 25 | 35 | 65 | 95 | 95 | 5 |

Gradient 2:

|  | t (min) | | | | | | |
| --- | --- | --- | --- | --- | --- | --- | --- |
|  | 0 | 0.2 | 0.3 | 4.4 | 4.5 | 5.6 | 5.7 |
| Solvent A (%) | 60 | 60 | 50 | 20 | 5 | 5 | 95 |
| Solvent B (%) | 40 | 40 | 50 | 80 | 95 | 95 | 5 |

VII) Preparative LC-MS (VII):

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 70 | 70 | 5 | 5 | 70 | 70 |
| Solvent B (%) | 30 | 30 | 95 | 95 | 30 | 30 |

VIII) Preparative LC-MS (VIII):

A Gemini column (Phenomenex NX 10 μm, 30×100 mm) was used. The two elution solvents were as follows: solvent A=water+0.5% $NH_4OH$; solvent B=acetonitrile. The eluent flow rate was 100 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.6 | 7.8 | 9.2 | 9.5 | 10 |
| Solvent A (%) | 90 | 90 | 5 | 5 | 90 | 90 |
| Solvent B (%) | 10 | 10 | 95 | 95 | 10 | 10 |

Preparative Chiral HPLC Methods Used:

The purifications by preparative chiral HPLC have been performed using the conditions described hereafter.

I) Preparative chiral HPLC (I):

A ChiralCel OD-H column (5 μm, 20×250 mm) was used. The elution solvent was Hep/EtOH/DEA 70/30/0.1, run for 15 min and at a flow rate of 16 mL/min.

II) Preparative chiral HPLC (II):

A ChiralPak IB column (5 μm, 20×250 mm) was used. The elution solvent was Hep/EtOH/DEA 70/30/0.1, run for 11 min and at a flow rate of 19 mL/min.

EXAMPLE 1

2-(3,5-Dimethyl-[1,2,4]triazol-1-yl)-1-{(R)-4-[4-(4-methoxy-phenyl)-2-trifluoromethyl-thiazol-5-yl]-2-methyl-piperazin-1-yl}-ethanone 1.1.
5-Bromo-2-trifluoromethyl-thiazole-4-carboxylic acid To a solution of 2-(trifluoromethyl)thiazole-4-carboxylic acid (3.2 g) in anhydrous THF (60 mL) under argon cooled down to −78° C. was added n-BuLi (1.6M in hexane, 21.3 mL) dropwise over 15 min so that the internal temperature did not rise above −60° C. A solution of $Br_2$ (0.92 mL) in cyclohexane (8 mL) was then added dropwise to keep the internal temperature below −60° C. The resulting mixture was stirred at −78° C. for 2 h and carefully quenched by addition of water (50 mL). Citric acid (10%) was added until pH=2 and the mixture was extracted with EA. The org. layers were washed with brine, dried ($MgSO_4$), filtered off and evaporated to dryness to afford 4.15 g of brown solid, used without further purification. LC-MS (B): $t_R$=0.67 min. F-NMR ($CD_3OD$): −63.57 ppm (s).

1.2.
5-Bromo-2-trifluoromethyl-thiazole-4-carboxylic acid methyl ester

To a solution of intermediate 1.1 (12 g), MeOH (130 mL) was added $H_2SO_4$ (6.5 mL) and the mixture stirred at 70° C.

for 3 h. After cooling down, the reaction mixture was quenched with sat. aq. Na₂CO₃ and the solvent partially evaporated off. The residue was diluted with DCM and washed with aq. sat. Na₂CO₃ (1×), water (1×) and brine (1×), and the aq. phases were extracted with DCM (2×). The combined org. layers were dried over MgSO₄, filtrated off, evaporated and dried under HV to afford 12 g of brown resin. LC-MS (B): $t_R$=0.83 min. F-NMR (CD₃OD): −63.59 ppm (s).

1.3. (R)-4-(4-Methoxycarbonyl-2-trifluoromethyl-thiazol-5-yl)-2-methyl-piperazine-1-carboxylic acid tert-butyl ester To a solution of intermediate 1.2 (10 g) in MeCN (250 mL) were added (R)-1-N-Boc-2-methylpiperazine (7.19 g) and DIPEA (8.85 mL) at RT. The reaction mixture was stirred at 80° C. for 43 h. After cooling down, the reaction mixture was diluted with EA and washed with water and brine. The aq. layers were extracted with EA. The combined org. layers were dried over MgSO₄, filtrated off and evaporated to dryness. The crude was purified by CC (Biotage, SNAP 340 g, solvent A: Hep; solvent B: EA; gradient in % B: 10 over 5CV, 10 to 30 over 5CV, 30 over 5CV) to afford 9.14 g of yellow resin. LC-MS (B): $t_R$=0.97 min; [M+H]⁺: 410.0.

1.4. 5-((R)-3-Methyl-piperazin-1-yl)-2-trifluoromethyl-thiazole-4-carboxylic acid methyl ester, hydrochloride salt A solution of intermediate 1.3 (4.5 g) in 4M HCl in dioxane (30 mL) was stirred at RT for 2 h. The solvent was removed under reduced pressure to afford 3.66 g of beige solid. LC-MS (B): $t_R$=0.54 min; [M+H]⁺: 310.0.

1.5. (R)-methyl 5-(4-(2-(3,5-dimethyl-1H-1,2,4-triazol-1-yl)acetyl)-3-methylpiperazin-1-yl)-2-(trifluoromethyl)thiazole-4-carboxylate To a suspension of (3,5-dimethyl-[1,2,4]triazol-1-yl)-acetic acid (2.25 g) and intermediate 1.4 (3.4 g) in DCM (100 mL) were added HATU (6.06 g) and DIPEA (5.62 g) and the reaction mixture was stirred at RT for 2 h. The mixture was diluted with DCM, washed with aq. sat. NaHCO₃ (2×) and the aq. layers extracted with DCM (3×). The combined org. layers were dried over Na₂SO₄ and concentrated to dryness. The crude was purified by CC (Biotage, SNAP 340 g cartridge, solvent A: DCM; solvent B: DCM/MeOH 8:2; gradient in % B: 0 over 1CV, 0 to 15 over 3CV, 15 for 5CV, 15 to 30 over 5CV) to afford 5.02 g as white foam. LC-MS (B): $t_R$=0.68 min; [M+H]⁺: 446.8.

1.6. (R)-5-(4-(2-(3, 5-dimethyl-1H-1,2,4-triazol-1-yl)acetyl)-3-methylpiperazin-1-yl)-2-(trifluoromethyl)thiazole-4-carboxylic acid To as solution of intermediate 1.5 (2.5 g) in MeOH (25 mL) was added aq. NaOH (1M, 25 mL) and the reaction mixture stirred for 2 h at RT. The mixture was concentrated to dryness, and citric acid (10%) was added until pH=2-3. The mixture was extracted with DCM (3×) and the combined org. layers were dried over Na₂SO₄, filtrated off and evaporated to afford 1.73 g as white solid. LC-MS (B): $t_R$=0.60 min; [M+H]⁺: 432.8.

1.7. (R)-1-(4-(4-bromo-2-(trifluoromethyl)thiazol-5-yl)-2-methylpiperazin-1-yl)-2-(3,5-dimethyl-1H-1,2,4-triazol-1-yl)ethanone To a solution of intermediate 1.6 (1 g) in THF (20 mL) were added LiBr (203 mg) and (diacetoxyiodo)benzene (760 mg) at RT. The resulting suspension was stirred at RT for 15 h30. The reaction mixture was diluted with H₂O and extracted with DCM (3×). The combined org. layers were dried over MgSO₄, filtrated off and evaporated to dryness. The crude was purified by CC (Biotage, SNAP 100 g cartridge, solvent A: DCM; solvent B: DCM/MeOH 8:2; gradient in % B: 0 for 1CV, 0 to 10 over 3CV, 10 over 5CV, 10 to 2 over 3CV, 20 over 5CV, 20 to 30% over 3CV) to afford 0.96 g as white foam. LC-MS (B): $t_R$=0.76 min; [M+H]⁺: 466.8.

1.8. 2-(3,5-Dimethyl-[1,2,4]triazol-1-yl)-1-{(R)-4-[4-(4-methoxy-phenyl)-2-trifluoromethyl-thiazol-5-yl]-2-methyl-piperazin-1-yl}-ethanone To a vial containing 4-methoxyphenylboronic acid (20 mg), Pd₂(dba)₃ (4.0 mg) and tricyclohexylphosphine (3.0 mg) were added a degased solution of intermediate 1.7 (41 mg) in dioxane (0.6 mL) and a degased 1M aq. K₃PO₄ solution (0.15 mL). The reaction mixture was stirred at 90° C. for 2 h under argon. MeOH was added and the reaction mixture filtered through a neutral alumina cartridge previously conditioned with MeOH. Purification by Prep LC-MS (VI, gradient 1) afforded 28 mg of the desired compound. LC-MS (A): $t_R$=1.08 min; [M+H]⁺: 495.4.

Example 2 to Example 16 were synthesized using the appropriate boronic acid derivative and following the procedure described in Example 1, step 1.8. LC-MS data of Example 2 to Example 16 are listed in the table below. The LC-MS conditions used were LC-MS (A). All examples were purified by Prep LC-MS (VI, gradient 1) except examples 2, 7 and 9 which were purified by Prep LC-MS (VI, gradient 2).

| Example N° | Name | $t_R$ | [M + H]⁺ |
|---|---|---|---|
| 2 | 2-(3,5-Dimethyl-[1,2,4]triazol-1-yl)-1-{(R)-4-[4-(4-isopropoxy-phenyl)-2-trifluoromethyl-thiazol-5-yl]-2-methyl-piperazin-1-yl}-ethanone | 1.2 | 523.4 |
| 3 | 2-(3,5-Dimethyl-[1,2,4]triazol-1-yl)-1-{(R)-2-methyl-4-[4-(4-trifluoromethoxy-phenyl)-2-trifluoromethyl-thiazol-5-yl]-piperazin-1-yl}-ethanone | 1.23 | 549.4 |
| 4 | 2-(3,5-Dimethyl-[1,2,4]triazol-1-yl)-1-((R)-2-methyl-4-{4-[4-(2,2,2-trifluoro-ethoxy)-phenyl]-2-trifluoromethyl-thiazol-5-yl}-piperazin-1-yl)-ethanone | 1.17 | 563.4 |

-continued

| Example N° | Name | $t_R$ | $[M + H]^+$ |
|---|---|---|---|
| 5 | 4-(5-{(R)-4-[2-(3,5-Dimethyl-[1,2,4]triazol-1-yl)-acetyl]-3-methyl-piperazin-1-yl}-2-trifluoromethyl-thiazol-4-yl)-benzonitrile | 1.05 | 490.4 |
| 6 | 2-(3,5-Dimethyl-[1,2,4]triazol-1-yl)-1-{(R)-4-[4-(4-fluoro-phenyl)-2-trifluoromethyl-thiazol-5-yl]-2-methyl-piperazin-1-yl}-ethanone | 1.11 | 483.4 |
| 7 | 1-{(R)-4-[4-(4-Chloro-phenyl)-2-trifluoromethyl-thiazol-5-yl]-2-methyl-piperazin-1-yl}-2-(3,5-dimethyl-[1,2,4]triazol-1-yl)-ethanone | 1.18 | 499.4 |
| 8 | 2-(3,5-Dimethyl-[1,2,4]triazol-1-yl)-1-[(R)-2-methyl-4-(4-p-tolyl-2-trifluoromethyl-thiazol-5-yl)-piperazin-1-yl]-ethanone | 1.15 | 479.4 |
| 9 | 2-(3,5-Dimethyl-[1,2,4]triazol-1-yl)-1-{(R)-4-[4-(4-ethyl-phenyl)-2-trifluoromethyl-thiazol-5-yl]-2-methyl-piperazin-1-yl}-ethanone | 1.21 | 493.4 |
| 10 | 2-(3,5-Dimethyl-[1,2,4]triazol-1-yl)-1-{(R)-4-[4-(3-fluoro-4-methoxy-phenyl)-2-trifluoromethyl-thiazol-5-yl]-2-methyl-piperazin-1-yl}-ethanone | 1.09 | 513.4 |
| 11 | 2-(3,5-Dimethyl-[1,2,4]triazol-1-yl)-1-{(R)-4-[4-(2-fluoro-4-methoxy-phenyl)-2-trifluoromethyl-thiazol-5-yl]-2-methyl-piperazin-1-yl}-ethanone | 1.05 | 513.4 |
| 12 | 2-(3,5-Dimethyl-[1,2,4]triazol-1-yl)-1-{(R)-4-[4-(4-methoxy-3-methyl-phenyl)-2-trifluoromethyl-thiazol-5-yl]-2-methyl-piperazin-1-yl}-ethanone | 1.16 | 509.4 |
| 13 | 1-[(R)-4-(4-Benzo[1,3]dioxol-5-yl-2-trifluoromethyl-thiazol-5-yl)-2-methyl-piperazin-1-yl]-2-(3,5-dimethyl-[1,2,4]triazol-1-yl)-ethanone | 1.06 | 509.4 |
| 14 | 1-{(R)-4-[4-(2,3-Dihydro-benzo[1,4]dioxin-6-yl)-2-trifluoromethyl-thiazol-5-yl]-2-methyl-piperazin-1-yl}-2-(3,5-dimethyl-[1,2,4]triazol-1-yl)-ethanone | 1.06 | 523.4 |
| 15 | 2-(3,5-Dimethyl-[1,2,4]triazol-1-yl)-1-{(R)-4-[4-(6-ethoxy-pyridin-3-yl)-2-trifluoromethyl-thiazol-5-yl]-2-methyl-piperazin-1-yl}-ethanone | 1.09 | 510.4 |
| 16 | 2-(3,5-Dimethyl-[1,2,4]triazol-1-yl)-1-{(R)-4-[4-(6-methoxy-pyridin-3-yl)-2-trifluoromethyl-thiazol-5-yl]-2-methyl-piperazin-1-yl}-ethanone | 1.02 | 496.4 |

EXAMPLE 17

2-(3-Dimethylaminomethyl-5-methyl-[1,2,4]triazol-1-yl)-1{(R)-4-[4-(2-ethoxy-pyrimidin-5-yl)-2-trifluoromethyl-thiazol-5-yl]-2-methyl-piperazin-1-yl}-ethanone 17.1. Methyl-(5-methyl-1H-[1,2,4]triazol-3-ylmethyl)-carbamic acid tert-butyl ester To a suspension of ethyl acetimidate hydrochloride (492 mg) in MeCN (10 mL) was added Amberlyst A21 (1.12 g). The suspension was stirred at RT for 15 min, filtered off and tert-butyl(2-hydrazino-2-oxoethyl)methylcarbamate (0.761 mL) was added to the filtrate. The reaction mixture was stirred at 50° C. for 92 h and at 100° C. for 8 h and was then evaporated to dryness. The residue was purified by CC (EA/MeOH 1/0, then 9/1) to afford 520 mg as yellow oil. LC-MS (B): $t_R$=0.54 min; [M+H]$^+$: 227.1.

17.2. Benzyl 2-(3-(((tert-butoxycarbonyl)(methyl)amino)methyl)-5-methyl-1H-1,2,4-triazol-1-yl)acetate To a solution of intermediate 17.1 (470 mg) in MeCN (20 mL) was added Cs$_2$CO$_3$ (677 mg) followed by benzyl bromoacetate (0.343 mL). The reaction mixture was stirred at RT overnight and evaporated to dryness. The residue was taken up in DCM and washed with water. The aq. layers were extracted with DCM, the combined org. layers were dried over Na$_2$SO$_4$, filtered off and evaporated to dryness. The residue was purified by CC (Hep/EA 1/1 then DCM/MeOH 9/1) to afford 290 mg as yellow oil. LC-MS (B): $t_R$=0.83 min; [M+H]$^+$: 375.1. $^1$H-NMR (CD$_3$OD): 7.39-7.35 (m, 5H); 5.24 (s, 2H); 5.09 (s, 2H); 4.43 (m, 2H); 2.89 (m, 3H); 2.41 (s, 3H); 1.44 (d, 9H). Roesy signal seen between CH$_2$ at 5.09 ppm and CH$_3$ at 2.41 ppm.

17.3. (5-methyl-3-methylaminomethyl-[1,2,4]triazol-1-yl)-acetic acid benzyl ester The Boc protecting group of intermediate 17.2 was cleaved using a method analogous to that of Example 1 step 1.4, intermediate 17.2 replacing intermediate 1.3. LC-MS (B): $t_R$=0.53 min; [M+H]$^+$: 275.1.

17.4. (3-Dimethylaminomethyl-5-methyl-[1,2,4]triazol-1-yl)-acetic acid benzyl ester A solution of intermediate 17.3 (250 mg) and formaldehyde (36.5% in water, 27.4 mg) in DCM (8 mL) was stirred at RT overnight. NaBH(OAc)$_3$ (272 mg) was added and the reaction mixture was stirred at RT for 1 h, diluted with DCM and washed with water. The aq. phase was extracted with DCM and evaporated to dryness to afford 150 mg as colourless oil. LC-MS (B): $t_R$=0.54 min; [M+H]$^+$: 289.1.

17.5. (3-Dimethylaminomethyl-5-methyl-[1,2,4]triazol-1-yl)-acetic acid

A flask containing intermediate 17.4 (150 mg), Pd/C (28 mg) in EtOH (10 mL) was evacuated and backfilled with argon (3×), afterwards evacuated and backfilled with H$_2$ (3×) and the reaction mixture stirred at RT for 2 h. The reaction mixture was filtered over a celite plug and the filtrate evaporated to dryness to afford 77 mg as white solid. LC-MS (B): $t_R$=0.15 min; [M+H]$^+$: 199.2.

17.6. (R)-4-(4-Carboxy-2-trifluoromethyl-thiazol-5-yl)-2-methyl-piperazine-1-carboxylic acid tert-butyl ester To a solution of intermediate 1.3 (4.25) in EtOH (40 mL) was added 1M NaOH (40 mL) at RT and the reaction mixture stirred for 1 h20. The solvent was evaporated off and the residue acidified to pH 2 by the addition of aq. citric acid (10%). The aq. layer was extracted with DCM (3×) and the combined org. layers were dried over Na$_2$SO$_4$ and concentrated to dryness to afford 4.1 g as orange solid. LC-MS (B): $t_R$=0.88 min; [M+H]$^+$: 395.9.

17.7. (R)-4-(4-Bromo-2-trifluoromethyl-thiazol-5-yl)-2-methyl-piperazine-1-carboxylic acid tert-butyl ester This compound was prepared using a method analogous to that of Example 1 step 1.7, intermediate 17.6 replacing intermediate 1.6. LC-MS (B): $t_R$=1.04 min; [M+H]$^+$: 429.2.

17.8. (R)-4-[4-(2-Ethoxy-pyrimidin-5-yl)-2-trifluoromethyl-thiazol-5-yl]-2-methyl-piperazine-1-carboxylic acid tert-butyl ester A mixture of intermediate 17.7 (1.63 g), 2-ethoxypyrimidine-5-boronic acid (778 mg), Pd(PPh$_3$)$_2$Cl$_2$ (152 mg), 1M Na$_2$CO$_3$ (12 mL) in MeCN (12 mL) was vigorously stirred at 80° C. under argon overnight. The reaction mixture was allowed to cool down to RT, diluted with H$_2$O and extracted with DCM (3×). The combined org. layers were dried over MgSO$_4$, filtrated off and evaporated to dryness. The crude was purified by CC (Biotage, SNAP 50 g cartridge, solvent A: Hep; solvent B: EA; gradient in % B: 10 for 5CV, 10 to 30 over 5CV, 30 for 3CV) to afford 1.35 g as pale yellow resin. LC-MS (B): $t_R$=1.04 min; [M+H]$^+$: 473.9.

17.9. 2-Ethoxy-5-[5-((R)-3-methyl-piperazin-1-yl)-2-trifluoromethyl-thiazol-4-yl]-pyrimidine To solution of intermediate 17.8 (1.32 g) in DCM (45 mL) was added TFA (4.28 mL) at RT. The resulting mixture was stirred at RT overnight. The reaction mixture was treated with 1M NaOH to pH=14 and extracted with DCM (3×). The combined org. layers were dried over MgSO$_4$, filtrated off, evaporated and dried at HV to afford 1.01 g as beige solid. LC-MS (B): $t_R$=0.64 min; [M+H]$^+$: 374.0.

17.10. 2-(3-Dimethylaminomethyl-5-methyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone A mixture of intermediate 17.5 (26 mg), intermediate 17.9 (50 mg), HATU (66 mg), and DIPEA (34 μL) in DCM (1.5 mL) was stirred for 1 h40 at RT. The reaction mixture was evaporated to dryness and the crude purified by Prep LC-MS (I) to afford 38 mg as white solid. LC-MS (D): $t_R$=1.23 min; [M+H]$^+$: 554.5.

EXAMPLE 18 AND EXAMPLE 19

1-{(R)-4-[4-(2-Ethoxy-pyrimidin-5-yl)-2-trifluoromethyl-thiazol-5-yl]-2-methyl-piperazin-1-yl}-2-(3-ethyl-5-methyl-[1,2,4]triazol-1-yl)-ethanone and 1-{(R)-4-[4-(2-Ethoxy-pyrimidin-5-yl)-2-trifluoromethyl-thiazol-5-yl]-2-methyl-piperazin-1-yl}-2-(5-ethyl-3-methyl-[1,2,4]triazol-1-yl)-ethanone Acid precursors for Example 18 and 19:

Step 18.1. To ethylacetimidate hydrochloride (500 mg) in MeCN (6 mL) was added Amberlyst A21 (1.14 g) and the suspension stirred at RT for 15 min. Then the mixture was filtrated and the resin washed with MeCN (1 mL). Propanoic acid hydrazide (353 mg) was added to the filtrate and the resulting white suspension stirred at 50° C. under argon for 4 d and at 80° C. overnight. The reaction mixture was evaporated. Purification by CC (Biotage, SNAP 10 g cartridge, solvent A: DCM; solvent B: MeOH; gradient in % B: 10 for 6CV, 10 to 20 over 3CV, 20 for 6CV) followed by a second CC (Biotage, SNAP 10 g cartridge, solvent A: DCM; solvent B: DCM/MeOH 8:2; gradient in % B: 25 for 7CV, 25 to 50 over 3CV, 50 for 5CV) afforded 3-ethyl-5-methyl-1H-[1,2,4]triazole (125 mg as yellow oil). LC-MS (B): $t_R$=0.21 min; [M+H]$^+$: 112.4.

Step 18.2: A method analogous to that of Example 17 step 17.2 was followed, 3-ethyl-5-methyl-1H-[1,2,4]triazole from step 18.1 replacing intermediate 17.1. A mixture of regioisomers was obtained: (3-Ethyl-5-methyl-[1,2,4]triazol-1-yl)-acetic acid benzyl ester and (5-ethyl-3-methyl-[1,2,4]triazol-1-yl)-acetic acid benzyl ester.

Step 18.3: A method analogous to that of Example 17 step 17.5 was followed, intermediates from step 18.2 replacing intermediate 17.4. A mixture of regioisomers (45:55) was obtained: (3-Ethyl-5-methyl-[1,2,4]triazol-1-yl)-acetic acid and (5-ethyl-3-methyl-[1,2,4]triazol-1-yl)-acetic acid.

To a suspension of the acid precursor mixture described in step 18.3 (85 mg) in DCM (6 mL) were added intermediate 17.9 (199 mg), DIPEA (1294) and HATU (249 mg) and the reaction mixture was stirred at RT for 1 h30. The mixture was evaporated and purified by Prep LC-MS (IV) followed by preparative chiral HPLC (I). Both fractions were taken up in DCM and washed with water (2×) and the aq. layers extracted with DCM (1×). The combined org. layers were dried over MgSO$_4$, filtrated off, evaporated and dried at HV.

First eluting fraction (Example 18): 1-{(R)-4-[4-(2-Ethoxy-pyrimidin-5-yl)-2-trifluoromethyl-thiazol-5-yl]-2-methyl-piperazin-1-yl}-2-(3-ethyl-5-methyl-[1,2,4]triazol-1-yl)-ethanone: 102 mg yellow resin. LC-MS (A): $t_R$=1.02 min; [M+H]$^+$: 525.4.

Second eluting fraction (Example 19): 1-{(R)-4-[4-(2-Ethoxy-pyrimidin-5-yl)-2-trifluoromethyl-thiazol-5-yl]-2-methyl-piperazin-1-yl}-2-(5-ethyl-3-methyl-[1,2,4]triazol-1-yl)-ethanone. 75 mg yellow resin. LC-MS (A): $t_R$=1.02 min; [M+H]$^+$: 525.4.

EXAMPLE 20

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone A mixture of intermediate 1.6 (30 mg), 5-bromo-2-ethoxypyrimidine (14 mg), TBACl (19 mg), Cs$_2$CO$_3$ (34 mg), [Pd(tBu$_3$P)$_2$] (1.8 mg) and DMF (1.5 mL) was stirred at 170° C. for 20 min under argon in the microwave. The crude mixture was purified by Prep LC-MS (I) followed by Prep LC-MS (IV) to afford 18 mg as white solid. LC-MS (A): $t_R$=0.98 min; [M+H]$^+$: 511.4.

Example 21 to Example 33 were synthesized following the procedure described in Example 20, the appropriate bromoaryl precursor replacing 5-bromo-2-ethoxypyrimidine: LC-MS data and purification methods are listed for these examples in the table below.

Bromoaryl Precursor for Example 25: 5-Bromo-2-(2-Methoxy-Ethoxy)-Pyrimidine

NaH (60% in oil, 122 mg) was added to a solution of 2-methoxy-ethanol (0.3 mL) in THF (25 mL) under argon at 0° C. and the reaction mixture stirred for 45 min at 0° C. Then, 5-bromo-2-chloropyrimidine (500 mg) was added and the reaction mixture allowed reaching RT. After 3.5 h, the reaction was quenched by the addition of aq. sat. NH$_4$Cl and THF was evaporated off. The aq. layer was extracted with DCM (2×) and the combined org. layers were dried over Na$_2$SO$_4$ and concentrated to dryness. Purification by CC (Hep/EA 7:3) afforded 5-bromo-2-(2-methoxy-ethoxy)-pyrimidine (0.37 g as yellow oil). LC-MS (B): $t_R$=0.64 min; [M+H]$^+$: 233.0.

Bromoaryl Precursor for Example 26: [2-(5-Bromo-Pyrimidin-2-Yloxy)-Ethyl]-Dimethylamine NaH (60% in oil, 122 mg) was added to a solution of dimethylethanolamine (0.38 mL) in THF (25 mL) under argon at 0° C. and the reaction mixture stirred for 45 min at 0° C. Then, 5-bromo-2-chloropyrimidine (500 mg) was added and the reaction mixture allowed reaching RT. After 1.5 h at RT, the reaction was quenched by the addition of aq. sat. NH$_4$Cl and THF was evaporated off. The aq. layer was extracted with DCM (2×) and the combined org. layers were dried over Na$_2$SO$_4$ and concentrated to dryness. Purification by CC (Hep/EA 7:3, then DCM/MeOH 9:1+1% Et$_3$N) afforded [2-(5-bromo-pyrimidin-2-yloxy)-ethyl]-dimethylamine (0.43 g as yellow oil). LC-MS (B): $t_R$=0.39 min; [M+H]$^+$: 246.1.

| Example N° | Name | Purification | $t_R$ | [M + H]$^+$ | LC-MS Method |
|---|---|---|---|---|---|
| 21 | 1-[(R)-4-(4-Chroman-6-yl-2-trifluoromethyl-thiazol-5-yl)-2-methyl-piperazin-1-yl]-2-(3,5-dimethyl-[1,2,4]triazol-1-yl)-ethanone | Prep LC-MS (IV, VII) | 1.13 | 521.4 | A |
| 22 | 2-(3,5-Dimethyl-[1,2,4]triazol-1-yl)-1-{(R)-2-methyl-4-[4-(2-propyl-pyrimidin-5-yl)-2-trifluoromethyl-thiazol-5-yl]-piperazin-1-yl}-ethanone | Prep LC-MS (III, I) + PrepTLC (DCM/MeOH 95:5) | 0.77 | 509.0 | B |
| 23 | 2-(3,5-Dimethyl-[1,2,4]triazol-1-yl)-1-{(R)-2-methyl-4-[4-(2-methyl-pyrimidin-5-yl)-2-trifluoromethyl-thiazol-5-yl]-piperazin-1-yl}-ethanone | Prep LC-MS (III, I) | 1.22 | 481.4 | C |
| 24 | 2-(3,5-Dimethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone | Prep LC-MS (III) | 1.06 | 535.4 | A |
| 25 | 2-(3,5-Dimethyl-[1,2,4]triazol-1-yl)-1-((R)-4-{4-[2-(2-methoxy-ethoxy)-pyrimidin-5-yl]-2-trifluoromethyl-thiazol-5-yl}-2-methyl-piperazin-1-yl)-ethanone | Prep LC-MS (III), PrepTLC (DCM/MeOH 95:5) | 0.92 | 541.4 | A |
| 26 | 1-((R)-4-{4-[2-(2-Dimethylamino-ethoxy)-pyrimidin-5-yl]-2-trifluoromethyl-thiazol-5-yl}-2-methyl-piperazin-1-yl)-2-(3,5-dimethyl-[1,2,4]triazol-1-yl)-ethanone | Prep LC-MS (I), PrepTLC (DCM/MeOH 95:5) | 1.04 | 554.5 | D |
| 27 | 2-(3,5-Dimethyl-[1,2,4]triazol-1-yl)-1-{(R)-4-[4-(2-isopropoxy-pyrimidin-5-yl)-2-trifluoromethyl-thiazol-5-yl]-2-methyl-piperazin-1-yl}-ethanone | Prep LC-MS (IV) | 1.05 | 525.4 | A |
| 28 | 2-(3,5-Dimethyl-[1,2,4]triazol-1-yl)-1-((R)-2-methyl-4-{4-[2-(2,2,2-trifluoro-ethoxy)-pyrimidin-5-yl]-2-trifluoromethyl-thiazol-5-yl}-piperazin-1-yl)-ethanone | CC (DCM/MeOH 97:3 to 8:2), Prep LC-MS (IV) | 1.07 | 565.4 | A |
| 29 | 1-{(R)-4-[4-(2,4-Diethoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone | CC (DCM/MeOH 97:3), Prep LC-MS (IV) | 1.03 | 555.5 | A |
| 30 | 2-(3,5-Dimethyl-[1,2,4]triazol-1-yl)-1-((R)-2-methyl-4-{4-[2-(oxetan-3-yloxy)-pyrimidin-5-yl]-2-trifluoromethyl-thiazol-5-yl}-piperazin-1-yl)-ethanone | CC (DCM/MeOH 97:3) | 1.25 | 539.4 | C |

| Example N° | Name | Purification | $t_R$ | [M + H]⁺ | LC-MS Method |
|---|---|---|---|---|---|
| 31 | 2-(3,5-Dimethyl-[1,2,4]triazol-1-yl)-1-{(R)-4-[4-(4-ethoxy-phenyl)-2-trifluoromethyl-thiazol-5-yl]-2-methyl-piperazin-1-yl}-ethanone | Prep LC-MS (VII) | 1.15 | 509.4 | A |
| 32 | 2-(3,5-Dimethyl-[1,2,4]triazol-1-yl)-1-{(R)-4-[4-(2-methoxy-pyrimidin-5-yl]-2-trifluoromethyl-thiazol-5-yl]-2-methyl-piperazin-1-yl}-ethanone | Prep LC (III) + PrepTLC (DCM/MeOH 95:5) | 0.91 | 497.4 | A |
| 33 | 1-{(R)-4-[4-(2-Cyclopropyl-pyrimidin-5-yl)-2-trifluoromethyl-thiazol-5-yl]-2-methyl-piperazin-1-yl}-2-(3,5-dimethyl-[1,2,4]triazol-1-yl)-ethanone | Prep LC-MS (III, I) | 0.99 | 507.4 | A |

EXAMPLE 34

2-(3,5-Dimethyl-[1,2,4]triazol-1-yl)-1-{(S)-4-[4-(2-ethoxy-pyrimidin-5-yl)-2-trifluoromethyl-thiazol-5-yl]-2-methyl-piperazin-1-yl}-ethanone

34.1. 5-{(S)-4-[2-(3,5-Dimethyl-[1,2,4]triazol-1-yl)-acetyl]-3-methyl-piperazin-1-yl}-2-trifluoromethyl-thiazole-4-carboxylic acid This compound was prepared using a method analogous to that of Example 1 (step 1.3 to step 1.6), (S)-1-N-Boc-2-methylpiperazine replacing (R)-1-N-Boc-2-methylpiperazine in step 1.3. LC-MS (B): $t_R$=0.61 min; [M+H]⁺: 432.9.

34.2. 2-(3,5-Dimethyl-[1,2,4]triazol-1-yl)-1-{(S)-4-[4-(2-ethoxy-pyrimidin-5-yl)-2-trifluoromethyl-thiazol-5-yl]-2-methyl-piperazin-1-yl}-ethanone This compound was prepared using a method analogous to that of Example 20, intermediate 34.1 replacing intermediate 1.6. The desired compound was purified by Prep LC-MS (IV). LC-MS (A): $t_R$=0.98 min; [M+H]⁺: 511.4.

EXAMPLE 35

2-(3,5-Dimethyl-[1,2,4]triazol-1-yl)-1-{4-[4-(2-ethoxy-pyrimidin-5-yl)-2-trifluoromethyl-thiazol-5-yl]-piperazin-1-yl}-ethanone

35.1. 4-(4-Methoxycarbonyl-2-trifluoromethyl-thiazol-5-yl)-piperazine-1-carboxylic acid tert-butyl ester This compound was prepared using a method analogous to that of Example 1 step 1.3, 1-Boc-piperazine replacing (R)-1-N-Boc-2-methylpiperazine. LC-MS (B): $t_R$=0.94 min; [M+H]⁺: 339.9.

35.2. 2-Ethoxy-5-(5-piperazin-1-yl-2-trifluoromethyl-thiazol-4-yl)-pyrimidine This compound was prepared using a method analogous to that of Example 17, step 17.6 to step 17.9, intermediate 35.1 replacing intermediate 1.3 in step 1.4. LC-MS (B): $t_R$=0.65 min; [M+H]⁺: 360.0.

35.3. 2-(3,5-Dimethyl-[1,2,4]triazol-1-yl)-1-{4-[4-(2-ethoxy-pyrimidin-5-yl)-2-trifluoromethyl-thiazol-5-yl]-piperazin-1-yl}-ethanone This compound was prepared using a method analogous to that of Example 1, step 1.5, intermediate 35.2 replacing intermediate 1.4. The desired compound was purified by Prep LC-MS (IV). LC-MS (A): $t_R$=0.96 min; [M+H]⁺: 497.4.

EXAMPLE 36

2-(3,5-Dimethyl-[1,2,4]triazol-1-yl)-1-{(R)-2-methyl-4-[4-(2-pyrrolidin-1-yl-pyrimidin-5-yl)-2-trifluoromethyl-thiazol-5-yl]-piperazin-1-yl}-ethanone This compound was prepared using a method analogous to that of Example 17 step 17.8, intermediate 1.7 replacing intermediate 17.7 and 2-pyrrolidinopyrimidine-5-boronic acid replacing 2-ethoxypyrimidine-5-boronic acid. The desired compound was purified by Prep LC-MS (I). LC-MS (A): $t_R$=1.02 min; [M+H]⁺: 536.5.

EXAMPLE 37

2-(3,5-Dimethyl-[1,2,4]triazol-1-yl)-1-((R)-2-methyl-4-{4-[2-(4-methyl-piperazin-1-yl)-pyrimidin-5-yl]-2-trifluoromethyl-thiazol-5-yl}-piperazin-1-yl)-ethanone This compound was prepared using a method analogous to that of Example 36, 2-(4-methylpiperazino)pyrimidine-5-boronic acid replacing 2-pyrrolidinopyrimidine-5-boronic acid. The desired compound was purified by Prep LC-MS (I). LC-MS (D): $t_R$=1.08 min; [M+H]⁺: 565.5.

EXAMPLE 38

1-{(R)-4-[4-(2-Cyclobutoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone

38.1. 5-Bromo-2-cyclobutoxy-pyrimidine

To a solution of cyclobutanol (0.2 mL) in THF (25 mL) was added at 0° C. NaH (122 mg, 60% in oil) and the mixture was stirred for 45 min under argon. Then, 5-bromo-2-chloropyrimidine (500 mg) was added and the mixture allowed to warm up to RT overnight. The reaction mixture was quenched by the addition of sat. NH$_4$Cl and extracted with DCM (2×). The combined org. layers were dried over Na$_2$SO$_4$ and concentrated to dryness. Purification by Prep LC-MS (II) afforded 0.38 g as white solid. LC-MS (B): $t_R$=0.82 min. $^1$H NMR (400 MHz, MeOD) δ: 1.67-1.78 (m, 1H), 1.84-1.93 (m, 1H), 2.13-2.24 (m, 2H), 2.44-2.53 (m, 2H), 5.14-5.22 (m, 1H), 8.59-8.69 (m, 2H)

38.2. (2-Cyclobutoxypyrimidin-5-yl)boronic acid

To a solution of intermediate 38.1 (350 mg) and triisopropyl borate (0.43 mL) in THF (1.1 mL) and toluene (4.4 mL) was added at −78° C. n-BuLi (1.83 mL, 1.6M) dropwise and the resulting suspension was stirred at −78° C. for 1 h. The reaction mixture was allowed to warm up to RT, acidified by addition of HCl (1M) to pH=1, diluted with H$_2$O and extracted with EA (3×). The combined org. layers were dried over Na$_2$SO$_4$ and concentrated to dryness. The residue was purified by Prep LC-MS (V) to afford 35 mg as white solid. LC-MS (B): $t_R$=0.56 min; [M+H]$^+$: 195.2.

38.3. 1-{(R)-4-[4-(2-Cyclobutoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone This compound was prepared using a method analogous to that of Example 36, intermediate 38.2 replacing 2-pyrrolidinopyrimidine-5-boronic acid. The desired compound was purified by Prep LC-MS (I). LC-MS (A): $t_R$=1.09 min; [M+H]$^+$: 537.4.

EXAMPLE 39

1-{(R)-4-[4-(3,4-Dihydro-2H-pyrano[2,3-b]pyridin-6-yl)-2-trifluoromethyl-thiazol-5-yl]-2-methyl-piperazin-1-yl}-2-(3,5-dimethyl-[1,2,4]triazol-1-yl)-ethanone A mixture of intermediate 1.7 (30 mg), 6-(4,4,5,5-tetramethyl-1,3,2-dioxaborolan-2-yl)-3,4-dihydro-2H-pyrano[2,3-b]pyridine (16.8 mg), Pd(PPh$_3$)$_4$ (3.8 mg), sat. aq. K$_2$CO$_3$ (0.3 mL) in dioxane (0.6 mL) at RT was vigorously stirred at 100° C. under argon for 16 h30. The solvent was evaporated off and the residue diluted with water and extracted with DCM (3×). The combined org. layers were dried over Na$_2$SO$_4$ and concentrated to dryness. Purification by Prep LC-MS (I) followed by Prep TLC (DCM/MeOH 97:3) afforded 5 mg as colorless resin.
LC-MS (A): $t_R$=0.93 min; [M+H]$^+$: 522.4.

EXAMPLE 40

1-{(R)-4-[4-(2,3-Dihydro-benzofuran-5-yl)-2-trifluoromethyl-thiazol-5-yl]-2-methyl-piperazin-1-yl}-2-(3,5-dimethyl-[1,2,4]triazol-1-yl)-ethanone This compound was prepared using a method analogous to that of Example 39, 2,3-dihydro-1-benzofuran-5-ylboronic acid replacing 6-(4,4,5,5-tetramethyl-1,3,2-dioxaborolan-2-yl)-3,4-dihydro-2H-pyrano[2,3-b]pyridine. The desired compound was purified by Prep LC-MS (I). LC-MS (A): $t_R$=1.08 min; [M+H]$^+$: 507.4.

EXAMPLE 41

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-2,2-dideuterium-ethanone A solution of Example 20 (30 mg) and DIPEA (5 μL) in CD$_3$OD (0.5 mL) was stirred at RT overnight. The reaction mixture was evaporated, diluted with DCM (1 mL) and H$_2$O (1 mL) and stirred for a few minutes. Then the phases were separated using a phase separator and the aq. layer was re-extracted with DCM. The combined org. layers were evaporated and dried at HV to give 24 mg as white solid. LC-MS (A): $t_R$=0.98 min; [M+H]$^+$: 513.4.

EXAMPLE 42

1-((R)-4-{4-[2-(2-Dimethylamino-ethyl)-pyrimidin-5-yl]-2-trifluoromethyl-thiazol-5-yl}-2-methyl-piperazin-1-yl)-2-(3,5-dimethyl-[1,2,4]triazol-1-yl)-ethanone 42.1. 5-Bromo-2-vinyl-pyrimidine To a solution of 5-bromo-2-iodopyrimidine (750 mg) and Pd(PPh$_3$)$_4$ (46 mg) in abs. THF (15 mL) under argon was added vinylmagnesium bromide (5.27 mL, as 1M THF solution) dropwise within 5 min at RT. The resulting solution was stirred at reflux for 2 h30 and the reaction mixture then allowed to cool to RT. The mixture was diluted with water and extracted with EA (3×). The combined org layers were washed with brine (2×), dried over MgSO$_4$, filtrated off and evaporated to dryness. Purification by CC (Biotage, SNAP 25 g cartridge, solvent A: Hep; solvent B: EA; gradient in % B: 0 to 5 over 1CV, 5 for 5CV, 5 to 10 over 3CV, 10 for 3CV) afforded 186 mg as yellow liquid. LC-MS (6): $t_R$=0.67 min. $^1$H NMR (400 MHz, CDCl$_3$): 5.80 (dd, J=10.5 Hz, 1 H), 6.65 (d, J=17.3 Hz, 1 H), 6.85 (dd, J$_1$=10.5 Hz, J$_2$=17.3 Hz 1 H), 8.76 (s, 2 H).

42.2. (4-vinylphenyl)boronic acid

To a solution of intermediate 42.1 (181 mg) in THF (1 mL) and toluene (4 mL) was added triisopropyl borate (0.28 mL) at −78° C. followed by dropwise addition over 5 min of n-BuLi (0.73 mL; 1.6M in hexanes) at −78° C. under argon. The suspension was stirred at −78° C. for 45 min and then allowed to warm up to RT. The reaction mixture was quenched by addition of 1M HCl (2.5 ml) to pH=1, diluted with H$_2$O and EA. The aq. layer was separated and extracted with EA (2×). The combined org. layers were dried over MgSO$_4$, filtrated off, evaporated and dried at HV to give 108 mg as orange solid, which was used without further purification. LC-MS (B): $t_R$=0.44 min; [M+H]$^+$: 151.2.

42.3. (R)-2-Methyl-4-[2-trifluoromethyl-4-(2-vinyl-pyrimidin-5-yl)-thiazol-5-yl]-piperazine-1-carboxylic acid tert-butyl ester This compound was prepared using a method analogous to that of Example 17, step 17.8, intermediate 42.2 replacing 2-ethoxypyrimidine-5-boronic acid. LC-MS (B): $t_R$=1.04 min; [M+H]$^+$: 456.2.

42.4. (R)-4-{4-[2-(2-Dimethylamino-ethyl)-pyrimidin-5-yl]-2-trifluoromethyl-thiazol-5-yl}-2-methyl-piperazine-1-carboxylic acid tert-butyl ester To a solution of intermediate 42.3 (23 mg) in MeOH (0.5 mL) was added dimethylamine (76 μL, as 2M solution in MeOH) at RT and the reaction mixture stirred at RT for 1 h. The mixture was evaporated to dryness, dried at HV to afford 30 mg as yellow resin. LC-MS (B): $t_R$=0.78 min; [M+H]$^+$: 501.3.

42.5. Dimethyl-(2-{5-[5-((R)-3-methyl-piperazin-1-34)-2-trifluoromethyl-thiazol-4-yl]-pyrimidin-2-yl}-ethyl)-amine, as hydrochloride salt This compound was prepared using a method analogous to that of Example 1, step 1.4, intermediate 42.4 replacing intermediate 1.3. LC-MS (B): $t_R$=0.49 min; [M+H]$^+$: 401.3.

42.6. 1-((R)-4-{4-[2-(2-Dimethylamino-ethyl)-pyrimidin-5-yl]-2-trifluoromethyl-thiazol-5-yl}-2-methyl-piperazin-1-yl)-2-(3,5-dimethyl-[1,2,4]triazol-1-yl)-ethanone This compound was prepared using a method analogous to that of Example 17 step 17.10, intermediate 42.5 replacing intermediate 17.9 and (3,5-dimethyl-[1,2,4]triazol-1-yl)-acetic acid replacing intermediate 17.5. LC-MS (D): $t_R$=1.03 min; [M+H]$^+$: 538.5.

EXAMPLE 43

2-(3,5-Dimethyl-[1,2,4]triazol-1-yl)-1-{(R)-4-[4-(2-ethyl-pyrimidin-5-yl)-2-trifluoromethyl-thiazol-5-yl]-2-methyl-piperazin-1-yl}-ethanone This compound was prepared using a method analogous to that of Example 20, 5-bromo-2-ethylpyrimidine replacing 5-bromo-2-ethoxypyrimidine. LC-MS (B): $t_R$=0.75 min; [M+H]$^+$: 494.5.

EXAMPLE 44

2-(3-Hydroxymethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone

44.1. 3-(tert-Butyl-dimethyl-silanyloxymethyl)-5-methyl-1H-[1,2,4]triazole

To a solution of (5-methyl-1H-1,2,4-triazol-3-yl)methanol (500 mg) in DMF (17.5 mL) was added at 0° C. Et$_3$N (1.08 mL), DMAP (54 mg) and tert-butyl(chloro)dimethylsilane (806 mg) and the reaction mixture was allowed to reach RT. After stirring for 16 h30, the reaction mixture was diluted with EA and washed with water (2×) and brine (1×). The aq. layers were re-extracted with EA (2×). The combined org. layers were dried over MgSO$_4$, filtrated off and evaporated to dryness. Purification by CC (Hep/EA 3:7) afforded 0.88 g as white solid. LC-MS (B): $t_R$=0.71 min; [M+H]$^+$: 228.2.

44.2A. [3-(tert-butyl-dimethyl-silanyloxymethyl)-5-methyl-[1,2,4]triazol-1-yl]-acetic acid benzyl ester and 42.2B. [5-(tert-butyl-dimethyl-silanyloxymethyl)-3-methyl-[1,2,4]triazol-1-yl]-acetic acid benzyl ester To a solution of intermediate 44.1 (860 mg) in DMF (15 mL) was added at 0° C. NaH (60% in oil, 182 mg) and the reaction mixture was stirred for 30 min at 0° C. After dropwise addition of benzyl bromoacetate (0.72 mL) at 0° C., the reaction mixture was allowed to reach RT overnight. The reaction was quenched by the addition of water and extracted with DCM (3×). The combined org. layers were washed with brine and water, dried over Na$_2$SO$_4$ and concentrated to dryness. The residue was dissolved in EA and washed with water (3×) and the org. layer dried over Na$_2$SO$_4$ and concentrated to dryness. Purification by CC (Hep/EA 7:3) gave as first eluting fraction 0.29 g of the regioisomer 42.2B [5-(tert-butyl-dimethyl-silanyloxymethyl)-3-methyl-[1,2,4]triazol-1-yl]-acetic acid benzyl ester. LC-MS (B): $t_R$=0.98 min; [M+H]$^+$: 376.06. Roesy signal at 5.11 ppm and 4.84 ppm seen between CH$_2$CO2Bn and CH$_2$OTBS. The second isolated fraction was purified again by CC (Biotage, SNAP 50 g cartridge, solvent A: Hep; solvent B: EA; gradient in % B: 0 to 30 over 20CV, 30 for 10CV) to afford 0.31 g of the other regioisomer 42.2A [3-(tert-butyl-dimethyl-silanyloxymethyl)-5-methyl-[1,2,4]triazol-1-yl]-acetic acid benzyl ester. LC-MS (B): $t_R$=0.96 min; [M+H]$^+$: 376.1. Roesy signal seen between CH$_2$CO2Bn at 4.88 ppm and CH$_3$ at 2.4 ppm.

44.3. [3-(tert-Butyl-dimethyl-silanyloxymethyl)-5-methyl-[1,2,4]triazol-1-yl]-acetic acid This compound was prepared using a method analogous to that of Example 17 step 17.5, intermediate 44.2A ([3-(tert-butyl-dimethyl-silanyloxymethyl)-5-methyl-[1,2,4]triazol-1-yl]-acetic acid benzyl ester) replacing intermediate 17.4. LC-MS (B): $t_R$=0.73 min; [M+H]$^+$: 286.1.

44.4. (R)-2-Methyl-4-[2-trifluoromethyl-4-(2-trifluoromethyl-pyrimidin-5-34)-thiazol-5-yl]-piperazine-1-carboxylic acid tert-butyl ester This compound was prepared using a method analogous to that of Example 17, step 17.8, 2-(trifluoromethyl)pyrimidine-5-yl-boronic acid replacing 2-ethoxypyrimidine-5-boronic acid. LC-MS (B): $t_R$=1.06 min; [M+H]$^+$: 441.8.

44.5. 5-[5-((R)-3-Methyl-piperazin-1-yl)-2-trifluoromethyl-thiazol-4-yl]-2-trifluoromethyl-pyrimidine, as hydrochloride salt This compound was prepared using a method analogous to that of Example 1, step 1.4, intermediate 44.4 replacing intermediate 1.3. LC-MS (B): $t_R$=0.7 min; [M+H]$^+$: 439.0.

44.6. 2-[3-(tert-Butyl-dimethyl-silanyloxymethyl)-5-methyl-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 17 step 17.10, intermediate 44.3 replacing intermediate 17.5 and intermediate 44.5 replacing intermediate 17.9. A Prep TLC (DCM/MeOH 97:3) was done instead of a Prep LC-MS. LC-MS (B): $t_R$=1.03 min; [M+H]$^+$: 664.9.

44.7. 2-(3-Hydroxymethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone To a solution of intermediate 44.6 (22 mg) in THF (1 mL) was added TBAF (1M in THF; 394) and the reaction mixture was stirred at RT for 2 h. The mixture was evaporated to dryness and the residue dissolved in DCM. The org. layer was washed with water and brine and the aq. layers were re-extracted with DCM (2x). The combined org. layers were dried over Na$_2$SO$_4$ and concentrated to dryness. Prep TLC (DCM/MeOH 95:5) gave 9 mg as yellowish solid. LC-MS (E): $t_R$=1.06 min; [M+H]$^+$: 551.2.

EXAMPLE 45

2-(5-Hydroxymethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone

45.1. [5-(tert-Butyl-dimethyl-silanyloxymethyl)-3-methyl-[1,2,4]triazol-1-yl]-acetic acid This compound was prepared using a method analogous to that of Example 17 step 17.5, intermediate 44.2B ([5-(tert-butyl-dimethyl-silanyloxymethyl)-3-methyl-[1,2,4]triazol-1-yl]-acetic acid benzyl ester) replacing intermediate 17.4. LC-MS (B): $t_R$=0.75 min; [M+H]$^+$: 286.1

45.2. 2-[5-(tert-Butyl-dimethyl-silanyloxymethyl)-3-methyl-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 44 step 44.6, intermediate 45.1 replacing intermediate 44.3. LC-MS (B): $t_R$=1.05 min; [M+H]$^+$: 665.0.

45.3. 2-(5-Hydroxymethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 44 step 44.7, intermediate 45.2 replacing intermediate 44.6. LC-MS (E): $t_R$=1.08 min; [M+H]$^+$: 551.2.

EXAMPLE 46 AND EXAMPLE 47

2-(3-Ethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone and 2-(5-Ethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone These compounds were prepared using a method analogous to that of Example 18 and Example 19, intermediate 44.5 replacing intermediate 17.9. A preparative chiral HPLC (II) was used to separate the regioisomers:

First eluting fraction (Example 46): 2-(3-Ethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone: 33 mg, white solid. LC-MS (E): $t_R$=1.14 min; [M+H]$^+$: 549.3. Roesy signal seen between triazol-CH3 2.47 ppm and CH$_2$CO at 4.96 ppm.

Second eluting fraction (Example 47): 2-(5-Ethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone. 32 mg, white solid. LC-MS (E): $t_R$=1.13 min; [M+H]$^+$: 549.3. Roesy signal seen between triazol-CH$_2$CH$_3$ 2.74 ppm and CH$_2$CO at 4.94 ppm.

EXAMPLE 48

2-[3-(1-Hydroxy-1-methyl-ethyl)-5-methyl-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone

48.1. [3-(1-Hydroxy-1-methyl-ethyl)-5-methyl-[1,2,4]triazol-1-yl]acetic acid benzyl ester This compound was prepared using a method analogous to that of Example 17 step 17.2, 2-(5-methyl-1H-1,2,4-triazol-1-yl)propan-2-ol replacing intermediate 17.1. LC-MS (B): $t_R$=0.63 min; [M+H]$^+$: 290.3.

48.2. [3-(1-Hydroxy-1-methyl-ethyl)-5-methyl-[1,2,4]triazol-1-yl]-acetic acid This compound was prepared using a method analogous to that of Example 17 step 17.5, intermediate 48.1 replacing intermediate 17.4. LC-MS (B): $t_R$=0.18 min; [M+H]$^+$: 200.6.

48.3. 2-[3-(1-Hydroxy-1-methyl-ethyl)-5-methyl-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 17 step 17.10, intermediate 48.2 replacing intermediate 17.5 and intermediate 44.5 replacing intermediate 17.9. LC-MS (E): $t_R$=1.1 min; [M+H]$^+$: 579.3.

EXAMPLE 49

2-(3,5-Dimethyl-[1,2,4]triazol-1-yl)-1-{(R)-2-methyl-4-[2-trifluoromethyl-4-(6-trifluoromethyl-pyridin-3-yl)-thiazol-5-yl]-piperazin-1-yl}-ethanone This compound was prepared using a method analogous to that of Example 36, 2-trifluoromethylpyridine-5-boronic acid replacing 2-pyrrolidinopyrimidine-5-boronic acid. The desired compound was purified by Prep LC-MS (IV). LC-MS (E): $t_R$=1.13 min; [M+H]$^+$: 534.3.

EXAMPLE 50

2-(3,5-Dimethyl-[1,2,4]triazol-1-yl)-1-{(S)-2-methyl-4-[2-trifluoromethyl-4-(2-trifluoromethyl-pyrimidin-5-yl)-thiazol-5-yl]-piperazin-1-yl}-ethanone 50.1. 1-[(S)-4-(4-Bromo-2-trifluoromethyl-thiazol-5-yl)-2-methyl-piperazin-1-yl]-2-(3,5-dimethyl-[1,2,4]triazol-1-yl)-ethanone This compound was prepared using a method analogous to that of Example 1 step 1.7, intermediate 34.1 replacing intermediate 1.6. LC-MS (B): $t_R$=0.76 min; [M+H]$^+$: 468.8.

50.2. 2-(3,5-Dimethyl-[1,2,4]triazol-1-yl)-1-{(S)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 1 step 1.8, 2-trifluoromethylpyrimidine-5-boronic acid replacing 4-methoxyphenylboronic acid and intermediate 50.1 replacing intermediate 1.7. The desired compound was purified by Prep LC-MS (I). LC-MS (E): $t_R$=1.1 min; [M+H]$^+$: 535.2

EXAMPLE 51

2-(3,5-Dimethyl-[1,2,4]triazol-1-yl)-1-{(R)-2-ethyl-4-[2-trifluoromethyl-4-(2-trifluoromethyl-pyrimidin-5-yl)-thiazol-5-yl]-piperazin-1-yl}-ethanone 51.1. (R)-2-Ethyl-4-(4-methoxycarbonyl-2-trifluoromethyl-thiazol-5-yl)-piperazine-1-carboxylic acid tert-butyl ester This compound was prepared using a method analogous to that of Example 1, step 1.3, (R)-1-Boc-2-ethyl-piperazine replacing (R)-1-N-Boc-2-methylpiperazine. LC-MS (B): $t_R$=1.0 min; [M+H]$^+$: 424.1. 51.2. (R)-5-(4-(tert-butoxycarbonyl)-3-ethylpiperazin-1-yl)-2-(trifluoromethyl)thiazole-4-carboxylic acid This compound was prepared using a method analogous to that of Example 17, step 17.6, intermediate 51.1 replacing intermediate 1.3. LC-MS (B): $t_R$=0.91 min; [M+H]$^+$: 410.0.

51.3. (R)-4-(4-Bromo-2-trifluoromethyl-thiazol-5-yl)-2-ethyl-piperazine-1-carboxylic acid tert-butyl ester To a suspension of lithium acetate (35 mg) and NBS (945 mg) in THF (3 mL) was added dropwise over 10 min a solution of intermediate 51.2 (1.25 g) in THF (5 mL). After 30 min at RT, the reaction mixture was evaporated to dryness. The residue was taken up in EA and water, the phases were separated and the aq. layer was extracted with EA (1×). The combined org. layers were washed with brine, dried over Na$_2$SO$_4$ and evaporated to dryness to give 1.25 g as orange oil. LC-MS (B): $t_R$=1.07 min; [M+H]$^+$: 384.9.

51.4. (R)-2-Ethyl-4-[2-trifluoromethyl-4-(2-trifluoromethyl-pyrimidin-5-yl)-thiazol-5-yl]-piperazine-1-carboxylic acid tert-butyl ester This compound was prepared using a method analogous to that of Example 17 step 17.8, intermediate 51.3 replacing intermediate 17.7 and 2-trifluoromethylpyrimidine-5-boronic acid replacing 2-ethoxypyrimidine-5-boronic acid. The crude was used after extraction without further purification. LC-MS (B): $t_R$=1.08 min; [M+H]$^+$: 512.1.

51.5. 5-[5-((R)-3-Ethyl-piperazin-1-yl)-2-trifluoromethyl-thiazol-4-yl]-2-trifluoromethylpyrimidine; as hydrochloride salt This compound was prepared using a method analogous to that of Example 1 step 1.4, intermediate 51.4 replacing intermediate 1.3. LC-MS (B): $t_R$=0.73 min; [M+H]$^+$: 412.0.

51.6. 2-(3,5-Dimethyl-[1,2,4]triazol-1-yl)-1-{(R)-2-ethyl-4-[2-trifluoromethyl-4-(2-trifluoromethyl-pyrimidin-5-yl)-thiazol-5-yl]-piperazin-1-yl}-ethanone To a suspension of (3,5-dimethyl-[1,2,4]triazol-1-yl)-acetic acid (30.5 mg) and intermediate 51.5 (80 mg) in DCM (2.25 mL) were added HATU (74.7 mg) and NEt$_3$ (62 µL) and the reaction mixture was stirred at RT for 3 h. The mixture was diluted with DCM, washed with 1M NaHSO$_4$, aq. sat. NaHCO$_3$, and brine, and the aq. layers were extracted with DCM (2×). The combined org. layers were dried over Na$_2$SO$_4$ and concentrated to dryness. The crude was purified by Prep LC-MS (VIII) to afford 38 mg as white solid. LC-MS (E): $t_R$=1.14 min; [M+H]$^+$: 549.3.

EXAMPLE 52

1-((R)-4-{4-[2-(1,1-Difluoro-ethyl)-pyrimidin-5-yl]-2-trifluoromethyl-thiazol-5-yl}-2-methyl-piperazin-1-yl)-2-(3,5-dimethyl-[1,2,4]triazol-1-yl)-ethanone 52.1. 5-Bromo-2-(1,1-difluoro-ethyl)-pyrimidine To a solution of 1-(5-bromopyrimidin-2-yl)ethanone (500 mg) in DCM (5 mL) was added at RT bis(2-methoxyethyl)aminosulfur trifluoride (50% in toluene, 3.67 mL) and the reaction mixture was heated to 40° C. for 2 h. The mixture was allowed to reach RT and was added dropwise to a mixture of 1M NaOH and ice under vigorous stirring. The org. layer was extracted with DCM (2×). The combined org. layers were washed with brine, dried over Na$_2$SO$_4$ and concentrated to dryness. Purification by CC (Biotage, SNAP 25 g cartridge, solvent A: Hep; solvent B: EA; gradient in % B: 0 for 1CV, 0 to 10 over 10CV, 10 for 5CV) gave 284 mg as bright-yellow liquid. LC-MS (B): $t_R$=0.7 min; [M+H]$^+$: 264.02.

52.2. (2-(1,1-difluoroethyl)pyrimidin-5-)boronic acid

This compound was prepared using a method analogous to that of Example 38 step 38.2, intermediate 52.1 replacing intermediate 38.1. The crude was used without Prep LC-MS purification. LC-MS (B): $t_R$=0.47 min; [M+H]$^+$: 189.23.

52.3. 1-((R)-4-{4-[2-(1,1-Difluoro-ethyl)-pyrimidin-5-yl]-2-trifluoromethyl-thiazol-5-yl}-2-methyl-piperazin-1-yl)-2-(3,5-dimethyl-1-[1,2,4]triazol-1-yl)-ethanone This compound was prepared using a method analogous to that of Example 36, intermediate 52.2 replacing 2-pyrrolidinopyrimidine-5-boronic acid. The desired compound was purified by Prep LC-MS (I) followed by Prep TLC (DCM/MeOH 97:3). LC-MS (E): $t_R$=1.03 min; $[M+H]^+$: 531.3.

II. Biological Assays

A) FLIPR assay: The bioactivity of compounds is tested in a fluorometric imaging plate reader (FLIPR: Molecular Devices) using engineered CHO-K1 cells expressing the human CXCR3A (GenBank: AY242128) coupled to a G protein (Galpha(16)). Cells are plated the day prior to bioassay in F12 medium supplemented with 10% FBS and G418 and hygromycin antibiotics to maintain recombinant selection. At the day of bioassay, cells are washed and dye loaded for one hour with Fluo-4-AM (Invitrogen) in Hanks Balanced Salt Solution (Invitrogen), buffered with 20 mM Hepes at pH 7.4 and sodium bicarbonate (0.015%), containing 5 mM probenecid. This buffer, but lacking the dye and containing probenecid at a concentration of 2.5 nM, is also used for washing steps (wash buffer); or lacking both dye and probenecid but supplemented with 0.1% BSA for compound dilution steps (dilution buffer). Cells are washed free of excess dye and 60 microliter of wash buffer is added. Stock solutions of test compounds are made up at a concentration of 10 mM in DMSO, and serially diluted in dilution buffer to concentrations required for inhibition dose response curves. After a 10 minute incubation period at 37° C., 10 microliters of each compound dilution are transferred from a compound plate to the plate containing the recombinant cells in the FLIPR instrument according to the manufacturer's instructions. Following basal readings, 10 microliter CXCL10 agonist at a concentration of 20 nM (from Peprotech) is added, again using the FLIPR instrument. Changes in fluorescence are monitored before and after addition of the test compounds. Emission peak values above base level after CXCL10 addition are exported after base line subtraction. The program XLfit is used to fit the data to a single site dose response curve and to calculate $IC_{50}$ values. The calculated $IC_{50}$ values may fluctuate depending on the daily assay performance. Fluctuations of this kind are known to those skilled in the art. In the case where $IC_{50}$ values have been determined several times for the same compound, mean values are given. Data are shown in Table 1.

TABLE 1

| Example No | FLIPR: $IC_{50}$ (nM) |
|---|---|
| 1 | 111 |
| 2 | 16 |
| 3 | 9.8 |
| 4 | 12 |
| 5 | 24 |
| 6 | 64 |
| 7 | 9.3 |
| 8 | 28 |
| 9 | 36 |
| 10 | 20 |
| 11 | 45 |
| 12 | 25 |
| 13 | 76 |
| 14 | 31 |
| 15 | 9.2 |
| 16 | 14 |
| 17 | 20 |
| 18 | 3.1 |
| 19 | 8.5 |
| 20 | 5.7 |
| 21 | 4.7 |
| 22 | 2.9 |
| 23 | 24 |
| 24 | 2.7 |
| 25 | 6.8 |
| 26 | 41 |
| 27 | 3.5 |
| 28 | 2.8 |
| 29 | 4.5 |
| 30 | 22 |
| 31 | 10 |
| 32 | 27 |
| 33 | 2.9 |
| 34 | 5.7 |
| 35 | 4.6 |
| 36 | 1.6 |
| 37 | 4.8 |
| 38 | 2.3 |
| 39 | 31 |
| 40 | 22 |
| 41 | 5.6 |
| 42 | 91 |
| 43 | 14 |
| 44 | 5.1 |
| 45 | 15 |
| 46 | 1.6 |
| 47 | 3.5 |
| 48 | 4.7 |
| 49 | 3.6 |
| 50 | 2.6 |
| 51 | 0.6 |
| 52 | 4.5 |

B) hERG Q-Patch assay: Compounds are evaluated for block of the hERG K channel using CHO cells stably expressing the hERG gene (accession number U04270, bSys, Witterswil. Switzerland) and the Patch robotic platform (Sophion, Ballerup, Denmark) in single-cell mode at room temperature. Cells are grown in culture flasks at 37° C. in 5% $CO_2$, in culture medium (Ham's F-12 Nutrient Mixture, Invitrogen 21765-029) supplemented with 9% (v/v) fetal calf serum, 0.9% Penicillin/Streptomycin (10,000 U/mL, Invitrogen 15140148), 100 μg/mL Hygromycin B (Invitrogen 10687010). When the cells are ~80% confluent (every 2-3 days), they are either split for further culture or used for electrophysiology. For further culture, cells are detached with 0.25% Trypsin EDTA solution (Invitrogen 25200-056) and a fraction of the cells (10-30%) is reseeded in culture medium. For electrophysiology, on the experimental day, cells are detached with 0.25% Trypsin EDTA solution and all cells are suspended in suspension medium (293 SFM II, Invitrogen 11686-029) supplemented with 20 mM HEPES and 0.04 mg/mL Trypsin inhibitor. Cells are kept in suspension medium at 32-35° C. in the QPatch robot until use, at which time aliquots are transferred to the extracellular solution (in mM: NaCl 150; KCl 4; $CaCl_2$ 1.2; $MgCl_2$ 1; HEPES 10; pH 7.4 with NaOH) containing 0.3% v/v DMSO and applied to the test plates. $K^+$ currents are measured with the patch-voltage-clamp technique in the whole-cell configuration with the internal solution (in nM: KCl, 140; NaCl, 10; $MgCl_2$, 1; HEPES, 10; EGTA, 5; pH=7.2 with KOH). Currents are low-pass filtered using the internal Bessel filter of the QPatch robot with a cut-off frequency of 2 kHz and are digitized at 10 kHz. $K^+$tail currents are produced from a holding voltage of −80 mV by a 500-ms depolarization to +20 mV followed by a 500-ms repolarization to −40 mV; tail current amplitudes are measured at the end of the repolarization to −40 mV. The pulse pattern is repeated every 10 sec during the experiment, baseline $K^+$ current is measured after 3 min in extracellular solution, test-solution containing compound is then applied, and $K^+$ current in presence of compound is measured 3 minutes after application to the cells. The respective test-solution is prepared by (1) dissolving the test-compound in pure DMSO, (2) diluting this DMSO solution in extracellular solution, and (3) adding further DMSO, such that the final test-solution has a concentration of either 300 nM or 3000 nM of the test-compound and contains 0.3% v/v DMSO. Compound effects are quantified as % block by dividing the current in presence of compound by the baseline current; two or three experiments are performed for each compound and the final value represents the mean of the results of each experiment.

| Example No | concentration [nM] | % block | concentration [nM] | % block |
|---|---|---|---|---|
| 1 | 300 | 4 | 3000 | 13 |
| 2 | 300 | 7 | 3000 | 38 |
| 3 | 300 | 19 | 3000 | 60 |
| 4 | 300 | 25 | 3000 | 54 |
| 5 | 300 | nd | 3000 | nd |
| 6 | 300 | 11 | 3000 | 51 |
| 7 | 300 | 34 | 3000 | 88 |
| 8 | 300 | 22 | 3000 | 61 |
| 9 | 300 | 12 | 3000 | 44 |
| 10 | 300 | 7 | 3000 | 20 |
| 11 | 300 | 10 | 3000 | 19 |
| 12 | 300 | 6 | 3000 | 27 |
| 13 | 300 | 9 | 3000 | 39 |
| 14 | 300 | 5 | 3000 | 14 |
| 15 | 300 | 1 | 3000 | 13 |
| 16 | 300 | 4 | 3000 | 14 |
| 17 | 300 | 13 | 3000 | 26 |
| 18 | 300 | 3 | 3000 | 13 |
| 19 | 300 | 4 | 3000 | 12 |
| 20 | 300 | 9 | 3000 | 20 |
| 21 | 300 | 1 | 3000 | 12 |
| 22 | 300 | 1 | 3000 | 7 |
| 23 | 300 | −1 | 3000 | −2 |
| 24 | 300 | 6 | 3000 | 18 |
| 25 | 300 | −1 | 3000 | 1 |
| 26 | 300 | −1 | 3000 | −8 |
| 27 | 300 | 2 | 3000 | 6 |
| 28 | 300 | 0 | 3000 | 6 |
| 29 | 300 | −2 | 3000 | 0 |
| 30 | 300 | 1 | 3000 | 6 |
| 31 | 300 | 6 | 3000 | 14 |
| 32 | 300 | −6 | 3000 | −5 |
| 33 | 300 | 4 | 3000 | 17 |
| 34 | 300 | 3 | 3000 | 4 |
| 35 | 300 | 2 | 3000 | 4 |
| 36 | 300 | 7 | 3000 | 15 |
| 37 | 300 | 2 | 3000 | 4 |
| 38 | 300 | 5 | 3000 | 11 |
| 39 | 300 | 3 | 3000 | 15 |
| 40 | 300 | 1 | 3000 | 25 |
| 41 | 300 | nd | 3000 | nd |
| 42 | 300 | −3 | 3000 | 0 |
| 43 | 300 | 4 | 3000 | 8 |
| 44 | 300 | −3 | 3000 | −6 |
| 45 | 300 | 0 | 3000 | 1 |
| 46 | 300 | 13 | 3000 | 29 |
| 47 | 300 | 5 | 3000 | 18 |
| 48 | 300 | 1 | 3000 | 2 |
| 49 | 300 | nd | 3000 | nd |
| 50 | 300 | 6 | 3000 | 15 |
| 51 | 300 | 6 | 3000 | 18 |
| 52 | 300 | 2 | 3000 | 6 | nd: not determined

C) Human Liver Microsome Assay:

Incubation with human liver microsomes was performed to assess metabolic stability at a single compound concentration of 1 μM. A 1 μL-aliquot of the compounds stock solutions in DMSO were added to 899 μL of 100 mM phosphate buffer (pH 7.4) containing the liver microsomes at a concentration of 0.5 mg/mL and the mixture was incubated at 37° C. in an Eppendorf thermomixer at 450 rpm. The reaction was initiated by addition of 100 μL of NADPH-regenerating system containing the glucose-6-phosphate dehydrogenase and at the pre-defined time points, 0, 1.5, 2.5, 5, 10, and 15 min, 100 μL of the incubation was transferred in 100 μL of ice-cold methanol to stop the reaction. Samples were centrifuged at 3220 g for 20 min at 4° C. and the supernatants were submitted to LC/MS-MS analysis.

Calculation of intrinsic clearance $CL_{int}$:

Natural logarithm of remaining amount of compound was plotted as function of time and the slope of the line determined.

Elimination rate constant (k)=−slope
Half-life $(t_{1/2})$=0.893/k
V=volume of incubation/amount of protein
Intrinsic clearance $(CL_{int})$=V×0.693/$t_{1/2}$

| Example No | $CL_{int}$ |
|---|---|
| 7 | 7 |
| 15 | 66 |
| 18 | 60 |
| 20 | 8 |
| 22 | 78 |
| 24 | 0 |
| 27 | 13 |
| 33 | 7 |
| 36 | 338 |
| 38 | 51 |
| 45 | 14 |
| 49 | 4 |
| 50 | 11 |
| 51 | 1 |
| 52 | 0 |

D) Determination of Pharmacokinetic Parameters:

Male Wistar rats (RccHan:WIST) were obtained from Harlan (Venray, The Netherlands) and used for pharmacokinetic experiments after an acclimatization period of at least 7 days. The body weight of the rats was about 250 g at the day of the experiment. Two days prior to dosing, rats were anesthetized for surgery via inhalation of isoflurane (4-5% for induction and 1.5-3% for maintenance) in oxygen. Buprenorphine was dosed as analgesic at 0.03 mg/kg sc half an hour before surgery. Under aseptic conditions, catheters were implanted into jugular vein for dosing and carotid artery to allow for multiple serial blood sampling. Animals foreseen for oral dosing did not undergo surgery, but blood samples were taken sublingually under light anesthesia with isoflurane. Compounds were administered intravenously via a 5-minute infusion at doses of 0.5 or 1 mg/kg body weight formulated as solutions in water prepared by pH adjustment or as an aqueous mixed micellar vehicle based on phospholipids and bile acids (mixed micelles). Oral administration at doses of 2 or 10 mg/kg was performed by gavage. Oral formulations were solutions in water prepared by pH adjustment or dispersions prepared by addition of a DMSO stock solution of the compounds to methylcellulose (0.5% w/v) in water. Blood samples were generally taken 0.5, 1, 2, 3, 4, 6, 8, and 24 hours after oral dosing and 2, 10, 20, 30 min and 1, 2, 3, 4, 6, 8, and 24 hours after end of infusion. Blood samples were centrifuged at 3000 g (10 minutes, 4° C.) and plasma was submitted to LC-MS/MS analysis.

Example 24 has a surprisingly high plasma concentration after oral administration if compared to reference compounds disclosed in WO 2010/126811. The reference compounds may be prepared according to the procedures disclosed in WO 2010/126811.

| Compound | Oral dose [mg/kg] | Formulation | AUC [ng*h]/mL |
|---|---|---|---|
| example 24: 2-(3,5-Dimethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone | 2 | Solution in purified water, pH modification for solubilization, pH 2.1 | 14000 |
| reference compound 1: 2-(3,5-Dimethyl-pyrazol-1-yl)-1-{4-[2-(2-methoxy-pyrimidin-5-yl)-4-trifluoromethyl-phenyl]piperazin-1-yl}-ethanone | 2 | Suspension in methylcellulose (0.5% w/v) in water | 273 |
| reference compound 2: 2-(3,5-Dimethyl-pyrazol-1-yl)-1-{4-[2-(2-methylsulfanyl-pyrimidin-5-yl)-4-trifluoromethyl-phenyl]-piperazin-1-yl}-ethanone | 2 | Suspension in methylcellulose (0.5% w/v) in water | 202 |

| Compound | Oral dose [mg/kg] | Formulation | AUC [ng*h]/mL |
|---|---|---|---|
| reference compound 3: 2-(3,5-Dimethyl-pyrazol-1-yl)-1-{4-[2-(2-methylamino-pyrimidin-5-yl)-4-trifluoromethyl-phenyl]-piperazin-1-yl}-ethanone | 2 | Solution in purified water, pH modification for solubilization, pH 3.03 | 271 |

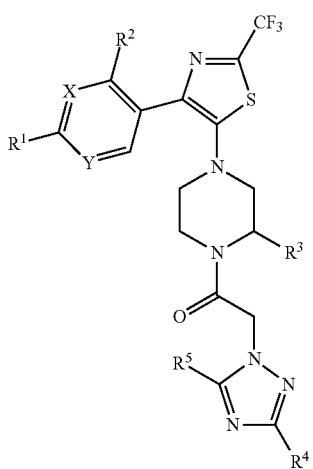

The invention claimed is:

1. A compound of Formula (I)

Formula (I)

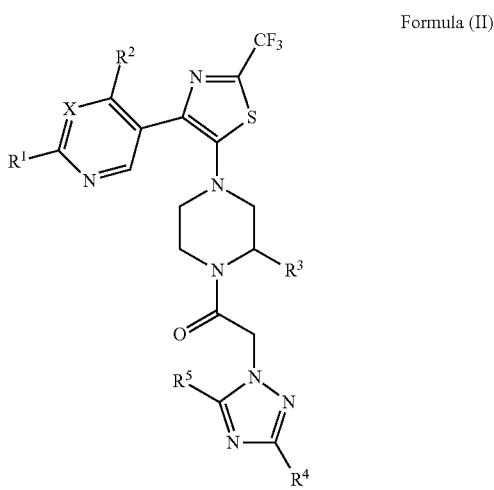

wherein
X represents N or CH;
Y represents N or $CR^6$;
$R^1$ represents $(C_{1-4})$alkyl; $(C_{3-6})$cycloalkyl; $(C_{1-4})$alkoxy; $(C_{3-6})$cycloalkoxy; $(C_{1-3})$fluoroalkyl; $(C_{1-3})$fluoroalkoxy; halogen; cyano; $(C_{1-2})$alkoxy-$(C_{2-3})$alkoxy; $(C_{1-3})$alkyl which is mono-substituted with —$NR^7R^8$; $(C_{2-3})$alkoxy which is mono-substituted with —$NR^7R^8$; heterocyclyl, wherein the heterocyclyl is a 4- to 6-membered mono-cyclic saturated ring comprising one or two heteroatoms independently selected from nitrogen or oxygen and wherein said heterocyclyl is unsubstituted or mono-substituted with $(C_{1-2})$alkyl; or heterocyclyloxy, wherein the heterocyclyl is a 4- to 6-membered mono-cyclic saturated ring comprising one oxygen atom;
$R^2$ represents hydrogen, $(C_{1-4})$alkoxy or fluoro;
$R^3$ represents hydrogen or $(C_{1-4})$alkyl;
$R^4$ represents $(C_{1-4})$alkyl, $(C_{1-4})$alkyl which is mono-substituted with hydroxy, or $(C_{1-2})$alkyl which is mono-substituted with —$NR^7R^8$;

$R^5$ represents $(C_{1-4})$alkyl or $(C_{1-4})$alkyl which is mono-substituted with hydroxy;
$R^6$ represents hydrogen, $(C_{1-4})$alkyl or fluoro; or $R^1$ and $R^6$ form, together with the carbon atoms to which they are attached, a 5- or 6-membered heterocyclic ring, wherein the moiety needed to complete said heterocyclic ring is selected from —$CH_2CH_2$—*, —$OCH_2O$—*,
—$OCH_2CH_2CH_2$—* or —$OCH_2CH_2O$—*, wherein the asterisks indicate the bond which is linked to the $R^6$ bearing carbon atom;
$R^7$ represents $(C_{1-2})$alkyl; and
$R^8$ represents $(C_{1-2})$alkyl;
or a salt of the compound.

2. The compound according to claim 1, wherein $R^1$ represents ethyl; n-propyl; cyclopropyl; ethoxy; iso-propoxy; cyclobutyloxy; trifluoromethyl; trifluoromethoxy; or 2,2,2-trifluoroethoxy;
or a salt of the compound.

3. The compound according to claim 1, which is also a compound of Formula (II).

Formula (II)

wherein

X represents N or CH;

R$^1$ represents (C$_{1-4}$)alkyl; (C$_{3-6}$)cycloalkyl; (C$_{1-4}$)alkoxy; (C$_{3-6}$)cycloalkoxy; (C$_{1-3}$)fluoroalkyl; (C$_{1-3}$)fluoroalkoxy; (C$_{1-2}$)alkoxy-(C$_{2-3}$)alkoxy; (C$_{1-3}$)alkyl which is mono-substituted with —NR$^7$R$^8$; (C$_{2-3}$)alkoxy which is mono-substituted with —NR$^7$R$^8$; heterocyclyl, wherein the heterocyclyl is a 4- to 6-membered mono-cyclic saturated ring comprising one or two heteroatoms independently selected from nitrogen and or oxygen and wherein said heterocyclyl is unsubstituted or mono-substituted with (C$_{1-2}$)alkyl; or heterocyclyloxy, wherein the heterocyclyl is a 4- to 6-membered mono-cyclic saturated ring comprising one oxygen atom;

R$^2$ represents hydrogen or (C$_{1-4}$)alkoxy;

R$^3$ represents hydrogen or methyl;

R$^4$ represents (C$_{1-4}$)alkyl, or (C$_{1-2}$)alkyl which is mono-substituted with —NR$^7$R$^8$;

R$^5$ represents (C$_{1-4}$)alkyl;

R$^7$ represents (C$_{1-2}$)alkyl; and

R$^8$ represents (C$_{1-2}$)alkyl;

or a salt of the compound.

4. The compound according to claim 3, wherein

X represents N or CH;

R$^1$ represents (C$_{1-4}$)alkyl; (C$_{3-6}$)cycloalkyl; (C$_{1-4}$)alkoxy; (C$_{3-6}$)cycloalkoxy; (C$_{1-2}$)fluoroalkyl; or (C$_{1-2}$)fluoroalkoxy;

R$^2$ represents hydrogen or ethoxy;

R$^3$ represents hydrogen or methyl;

R$^4$ represents methyl or ethyl; and

R$^5$ represents methyl or ethyl;

or a salt of the compound.

5. The compound according to claim 3, wherein

X represents N;

or a salt of the compound.

6. The compound according to claim 1, which is also a compound of Formula (III)

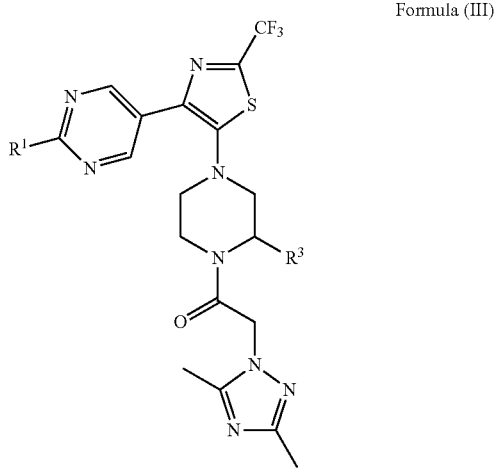

Formula (III)

wherein

R$^1$ represents (C$_{1-4}$)alkyl; (C$_{3-6}$)cycloalkyl; (C$_{1-4}$)alkoxy; (C$_{3-6}$)cycloalkoxy; (C$_{1-2}$)fluoroalkyl; or (C$_{1-2}$)fluoroalkoxy; and R$^3$ represents hydrogen or methyl;

or a salt of the compound.

7. The compound according to claim 6, wherein

R$^1$ represents ethyl; n-propyl; cyclopropyl; ethoxy; isopropoxy; cyclobutyloxy; trifluoromethyl; or 2,2,2-trifluoroethoxy;

or a salt of the compound.

8. The compound according to claim 6, wherein

R$^1$ represents (C$_{1-4}$)alkoxy; or (C$_{1-2}$)fluoroalkyl;

or a salt of the compound.

9. The compound according to claim 6, wherein

R$^3$ represents methyl;

or a salt of the compound.

10. The compound according to claim 1, wherein said compound is:

2-(3,5-Dimethyl-[1,2,4]triazol-1-yl)-1-{(R)-4-[4-(4-methoxy-phenyl)-2-trifluoromethyl-thiazol-5-yl]-2-methyl-piperazin-1-yl}ethanone;

2-(3,5-Dimethyl-[1,2,4]triazol-1-yl)-1-{(R)-4-[4-(4-isopropoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-2-methyl-4-[4-(4-trifluoromethoxy-phenyl)-2-trifluoromethyl-thiazol-5-yl]-piperazin-1-yl}-ethanone;

2-(3,5-Dimethyl-[1,2,4]triazol-1-yl)-1-((R)-2-methyl-4-{4-[4-(2,2,2-trifluoro-ethoxy)-phenyl]-2-trifluoromethyl-thiazol-5-yl}-piperazin-1-yl)-ethanone;

4-(5-{(R)-4-[2-(3,5-Dimethyl-[1,2,4]triazol-1-yl)-acetyl]-3-methyl-piperazin-1-yl}-2-trifluoromethyl-thiazol-4-yl)-benzonitrile;

2-(3,5-Dimethyl-[1,2,4]triazol-1-yl)-1-{(R)-4-[4-(4-fluoro-phenyl)-2-trifluoromethyl-thiazol-5-yl]-2-methyl-piperazin-1-yl}-ethanone;

1-{(R)-4-[4-(4-Chloro-phenyl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-[(R)-2-methyl-4-(4-p-tolyl-2-trifluoromethyl-thiazol-5-yl)-piperazin-1-yl]ethanone;

2-(3,5-Dimethyl-[1,2,4]triazol-1-yl)-1-{(R)-4-[4-(4-ethyl-phenyl)-2-trifluoronnethyl-thiazol-5-yl]-2-methyl-piperazin-1-yl}-ethanone;

2-(3,5-Dimethyl-[1,2,4]triazol-1-yl)-1-{(R)-4-[4-(3-fluoro-4-methoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(2-fluoro-4-methoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(4-methoxy-3-methyl-phenyl)-2-trifluoromethyl-thiazol-5-yl]-2-methyl-piperazin-1-yl}-ethanone;

1-[(R)-4-(4-Benzo[1,3]dioxol-5-yl-2-trifluoromethyl-thiazol-5-yl)-2-methyl-piperazin-1-yl]-2-(3,5-dimethyl-[1,2,4]triazol-1-yl)-ethanone;

1-{(R)-4-[4-(2,3-Dihydro-benzo[1,4]dioxin-6-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-4-[4-(6-ethoxy-pyridin-3-yl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(6-methoxy-pyridin-3-yl)-2-trifluoromethyl-thiazol-5-yl]-2-methyl-piperazin-1-yl}-ethanone;

2-(3-Dimethylaminomethyl-5-methyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone;

1-{(R)-4-[4-(2-Ethoxy-pyrimidin-5-yl)-2-trifluoromethyl-thiazol-5-yl]-2-methyl-piperazin-1-yl}-2-(3-ethyl-5-methyl-[1,2,4]triazol-1-yl)-ethanone;

1-{(R)-4-[4-(2-Ethoxy-pyrimidin-5-yl)-2-trifluoromethyl-thiazol-5-yl]-2-methyl-piperazin-1-yl}-2-(5-ethyl-3-methyl-[1,2,4]triazol-1-yl)-ethanone;

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone;

1-[(R)-4-(4-Chroman-6-yl-2-trifluoromethyl-thiazol-5-yl)-2-methyl-piperazin-1-yl]-2-(3,5-dimethyl-[1,2,4]triazol-1-yl)-ethanone;

2-(3,5-Dimethyl-[1,2,4]triazol-1-yl)-1-{(R)-2-methyl-4-[4-(2-propyl-pyrimidin-5-yl)-2-trifluoromethyl-thiazol-5-yl]-piperazin-1-yl}-ethanone;

2-(3,5-Dimethyl-[1,2,4]triazol-1-yl)-1-{(R)-2-methyl-4-[4-(2-methyl-pyrimidin-5-yl)-2-trifluoromethyl-thiazol-5-yl]-piperazin-1-yl}-ethanone;

2-(3,5-Dimethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}ethanone;

2-(3,5-Dimethyl-[1,2,4]triazol-1-yl)-1-((R)-4-{4-[2-(2-methoxy-ethoxy)-pyrimidin-5-yl]-2-trifluoromethyl-thiazol-5-yl}-2-methyl-piperazin-1-yl)-ethanone;

1-((R)-4-{4-[2-(2-Dimethylamino-ethoxy)-pyrimidin-5-yl]-2-trifluoromethyl-thiazol-5-yl}-2-methyl-piperazin-1-yl)-2-(3,5-dimethyl-[1,2,4]triazol-1-yl)-ethanone;

2-(3,5-Dimethyl-[1,2,4]triazol-1-yl)-1-{(R)-4-[4-(2-isopropoxy-pyrimidin-5-yl)-2-trifluoromethyl-thiazol-5-yl]-2-methyl-piperazin-1-yl}-ethanone;

2-(3,5-Dimethyl-[1,2,4]triazol-1-yl)-1-((R)-2-methyl-4-{4-[2-(2,2,2-trifluoro-ethoxy)-pyrimidin-5-yl]-2-trifluoromethyl-thiazol-5-yl}piperazin-1-yl)-ethanone;

1-{(R)-4-[4-(2,4-Diethoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-((R)-2-methyl-4-{4[2-(oxetan-3-yloxy)-pyrimidin-5-yl]-2-trifluoromethyl-thiazol-5-yl}piperazin-1-yl)-ethanone;

2-(3,5-Dimethyl-[1,2,4]triazol-1-yl)-1-{(R)-4-[4-(4-ethoxy-phenyl)-2-trifluoromethyl-thiazol-5-yl]-2-methyl-piperazin-1-yl}-ethanone;

2-(3,5-Dimethyl-[1,2,4]triazol-1-yl)-1-{(R)-4-[4-(2-methoxy-pyrimidin-5-yl)-2-trifluoromethyl-thiazol-5-yl]-2-methyl-piperazin-1-yl}-ethanone;

1-{(R)-4-[4-(2-Cyclopropyl-pyrimidin-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(S)-4-[4-(2-ethoxy-pyrimidin-5-yl)-2-trifluoromethyl-thiazol-5-yl]-2-methyl-piperazin-1-yl}-ethanone;

2-(3,5-Dimethyl-[1,2,4]triazol-1-yl)-1-{4-[4-(2-ethoxy-pyrimidin-5-yl)-2-trifluoromethyl-thiazol-5-yl]-piperazin-1-yl}-ethanone;

2-(3,5-Dimethyl-[1,2,4]triazol-1-yl)-1-{(R)-2-methyl-4-[4-(2-pyrrolidin-1-yl-pyrimidin-5-yl)-2-trifluoromethyl-thiazol-5-yl]-piperazin-1-yl}-ethanone;

2-(3,5-Dimethyl-[1,2,4]triazol-1-yl)-1-((R)-2-methyl-4-{4-[2-(4-methyl-piperazin-1-yl)-pyrimidin-5-yl]-2-trifluoromethyl-thiazol-5-yl}-piperazin-1-yl)-ethanone;

1-{(R)-4-[4-(2-Cyclobutoxy-pyrimidin-5-yl)-2-trifluoromethyl-thiazol-5-yl]-2-methyl-piperazin-1-yl}-2-(3,5-dimethyl-[1,2,4]triazol-1-yl)-ethanone;

1-{(R)-4-[4-(3,4-Dihydro-2H-pyrano[2,3-b]pyridin-6-yl)-2-trifluoromethyl-thiazol-5-yl ]-2-methyl-piperazin-1-yl}-2-(3,5-dimethyl-[1,2,4]triazol-1-yl)-ethanone;

1-{(R)-4-[4-(2,3-Dihydro-benzofuran-5-yl)-2-trifluoromethyl-thiazol-5-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-2,2-dideuterium-ethanone;

1-((R)-4-{4-[2-(2-Dimethylamino-ethyl)-pyrimidin-5-yl]-2-trifluoromethyl-thiazol-5-yl}-2-methyl-piperazin-1-yl)-2-(3,5-dimethyl-[1,2,4]triazol-1-yl)-ethanone; or 2-(3,5-Dimethyl-[1,2,4]triazol-1-yl)-1-{(R)-4-[4-(2-ethyl-pyrimidin-5-yl)-2-trifluoromethyl-thiazol-5-yl]-2-methyl-piperazin-1-yl}-ethanone;

or a salt of the compound.

11. The compound according to claim 1, wherein the compound is:

2-(3-Hydroxymethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(5-Hydroxymethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(3-Ethyl-5-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(5-Ethyl-3-methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-[3-(1-Hydroxy-1-methyl-ethyl)-5-methyl-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone;

2-(3,5-Dimethyl-[1,2,4]triazol-1-yl)-1-{(R)-2-methyl-4-[2-trifluoromethyl-4-(6-trifluoromethyl-pyridin-3-yl)-thiazol-5-yl]-piperazin-1-yl}-ethanone;

2-(3,5-Dimethyl-[1,2,4]triazol-1-yl)-1-{(S)-2-methyl-4-[2-trifluoromethyl-4-(2-trifluoromethyl-pyrimidin-5-yl)-thiazol-5-yl]-piperazin-1-yl}-ethanone;

2-(3,5-Dimethyl-[1,2,4]triazol-1-yl)-1-{(R)-2-ethyl-4-[2-trifluoromethyl-4-(2-trifluoromethyl-pyrimidin-5-yl) thiazol-5-yl]-piperazin-1-yl}-ethanone; or 1-((R)-4-{4-[2-(1,1-Difluoro-ethyl)-pyrimidin-5-yl]-2-trifluoronnethyl-thiazol-5-yl}-2-methyl-piperazin-1-yl)-2-(3,5-dimethyl-[1,2,4]triazol-1-yl)-ethanone;

or a salt of the compound.

12. The pharmaceutical composition comprising, as active principle, a compound according to claim 1, or a pharmaceutically acceptable salt thereof, and at least one therapeutically inert excipient.

13. The compound according to claim 1, or a pharmaceutically acceptable salt thereof, wherein the compound or salt thereof is formulated as a medicament.

14. The compound according to claim 1, wherein
X represents N or CH;
Y represents N or CR$^6$;
R$^1$ represents (C$_{1-4}$)alkyl; (C$_{3-6}$)cycloalkyl; (C$_{1-4}$)alkoxy; (C$_{3-6}$)cycloalkoxy; (C$_{1-3}$)fluoroalkyl; (C$_{1-3}$)fluoroalkoxy; halogen; cyano; (C$_{1-2}$)alkoxy-(C$_{2-3}$)alkoxy; (C$_{1-3}$)alkyl which is mono-substituted with —NR$^7$R$^8$; (C$_{2-3}$)alkoxy which is mono-substituted with —NR⁷R⁸; heterocyclyl, wherein the heterocyclyl is a 4- to 6-membered mono-cyclic saturated ring containing one or two heteroatoms independently selected from nitrogen or oxygen and wherein said heterocyclyl is unsubstituted or mono-substituted with $(C_{1-2})$alkyl; or heterocyclyloxy, wherein the heterocyclyl is a 4- to 6-membered mono-cyclic saturated ring comprising one oxygen atom;

$R^2$ represents hydrogen, $(C_{1-4})$alkoxy or fluoro;

$R^3$ represents hydrogen or methyl;

$R^4$ represents $(C_{1-4})$alkyl, or $(C_{1-2})$alkyl which is mono-substituted with —NR⁷R⁸;

$R^5$ represents $(C_{1-4})$alkyl;

$R^6$ represents hydrogen, $(C_{1-4})$alkyl or fluoro; or $R^1$ and $R^6$ form, together with the carbon atoms to which they are attached, a 5- or 6-membered heterocyclic ring, wherein the moiety needed to complete said heterocyclic ring is selected from —OCH₂CH₂—*, —OCH₂O—*, —OCH₂CH₂CH₂—* or —OCH₂CH₂O—*, wherein the asterisks indicate the bond which is linked to the $R^6$ bearing carbon atom;

$R^7$ represents $(C_{1-2})$alkyl; and $R^8$ represents $(C_{1-2})$alkyl;

or a salt of the compound.

15. A method of treating a disease comprising administering to a subject in need thereof the compound according to claim 1, wherein the disease is rheumatoid arthritis, inflammatory bowel disease, Crohn's disease, or ulcerative colitis.

16. A method of treating a disease comprising administering to a subject in need thereof the pharmaceutical composition according to claim 12, wherein the disease is rheumatoid arthritis, inflammatory bowel disease, Crohn's disease, or ulcerative colitis.

* * * * *